US011001849B2

(12) United States Patent
Pennell et al.

(10) Patent No.: US 11,001,849 B2
(45) Date of Patent: May 11, 2021

(54) METHODS OF INCREASING CROP YIELD UNDER ABIOTIC STRESS

(71) Applicant: CERES, INC., Thousand Oaks, CA (US)

(72) Inventors: Roger I. Pennell, Malibu, CA (US); Wuyi Wang, Newbury Park, CA (US); Chuan-Yin Wu, Newbury Park, CA (US); Dwarkesh Parihar, Hyderabad (IN); Paresh Verma, Hyderabad (IN); Vijay R. Kumar, Hyderabad (IN); Shridhar J. Rao, Hyderabad (IN)

(73) Assignee: CERES, INC., Thousand Oaks, CA (US)

(*) Notice: Subject to any disclaimer, the term of this patent is extended or adjusted under 35 U.S.C. 154(b) by 0 days.

(21) Appl. No.: 16/576,004

(22) Filed: Sep. 19, 2019

(65) Prior Publication Data
US 2020/0095595 A1 Mar. 26, 2020

Related U.S. Application Data

(62) Division of application No. 15/326,437, filed as application No. PCT/US2015/040614 on Jul. 15, 2015, now Pat. No. 10,480,000.

(60) Provisional application No. 62/024,791, filed on Jul. 15, 2014.

(51) Int. Cl.
C12N 15/82 (2006.01)
(52) U.S. Cl.
CPC ..... *C12N 15/8222* (2013.01); *C12N 15/8201* (2013.01); *C12N 15/8271* (2013.01); *C12N 15/8273* (2013.01)
(58) Field of Classification Search
None
See application file for complete search history.

(56) References Cited

U.S. PATENT DOCUMENTS

| 2006/0195934 | A1* | 8/2006 | Apuya | C12N 15/8216 800/278 |
| 2011/0167514 | A1 | 7/2011 | Brover et al. | |
| 2013/0014292 | A1* | 1/2013 | Pennell | C12N 15/8261 800/290 |
| 2013/0044919 | A1 | 2/2013 | Purcell et al. | |
| 2020/0040349 | A1 | 2/2020 | Pennell et al. | |

FOREIGN PATENT DOCUMENTS

| WO | WO 2009/127441 | 10/2009 | |
| WO | WO 2010/068418 A2 | 6/2010 | |
| WO | WO 2011/021190 A1 | 2/2011 | |
| WO | WO-2011021190 A1 * | 2/2011 | ......... C12N 15/8261 |
| WO | WO 2012/058223 A1 | 5/2012 | |

OTHER PUBLICATIONS

Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
Miller (Curr Protein Pept. Sci., 10:244-269, 2009).*
Doerks et al., (TIG, 14:248-250, 1998).*
Smith et al. (Nature Biotechnology, 15:1222-1223, 1997).*
Bork et al. (TIG, 12:425-427, 1996).*
Bhaskaran et al., "Accelerated reactive oxygen scavenging system and membrane integrity of two *Panicum* species varying in salt tolerance," *Cell Biochem Biophys*, 67(3):885-892, 2013.
Hu et al., (Journal of Plant Physiology, 165:1717-1725, 2008).
International Search Report and Written Opinion for PCT/US2015/040614, dated Jan. 14, 2016.
Kuettner, et al., "The active principle of garlic at atomic resolution," *J Biol Chem*, 277(48):46402-46407, 2002.
Nishimura et al. (Plant Cell Physiol., 41(5):583-590, 2000).
Reichmann et al. (Bio. Chem. 379(6):633-646-1998).
Rhodes et al., "Sequence motifs for calmodulin recognition," Faseb J, 11(5):331-340, 1997.
Watanabe et al., "Mechanism of substrate recognition and PLP-induced conformational changes in LL-Diaminopimelate aminotransferase from *Arabidopsis thaliana*," *J Mol Biol*, 384:1314-1329, 2008.
Yang et al. (PNAS, 98:11438-11443, 2001).
Yang et al. (Plant Molecular Biology, 58:585-596, 2005).
Zhao et al. (Planta, 227:1389-1399, 2008).
European Supplemental Search Report regarding European Application No. 15821980, dated Nov. 24, 2017.
Dkhili et al., "Salt Effects on Seedling Growth of Switchgrass and Big Bluestem," Proceedings of the Twelfth North American Prairie Conference, pp. 13-16, 1990.
Lemus et al., "Nutrient Uptake by 'Alamo' Switchgrass Used as an Energy Crop," Bioenerg. Res. 2:37-50, 2009.
Mehterov et al., "Oxidative stress provokes distinct transcriptional responses in the stress-tolerant atr7 and stress-sensitive loh2 *Arabidopsis thaliana* mutants as revealed by multi-parallel quantitative real-time PCR analysis of ROS marker and antioxidant genes," Plant Physiology and Biochemistry 59:20-29, 2012.
GI:224109704.
USPTO: Non-Final Office Action regarding U.S. Appl. No. 16/575,980, dated Aug. 11, 2020.
Response to Non-Final Office Action regarding U.S. Appl. No. 16/575,980, dated Sep. 21, 2020.
Supplemental Response to Non-Final Office Action regarding U.S. Appl. No. 16/575,980, dated Sep. 28, 2020.
USPTO: Notice of Allowance and Fee(s) Due regarding U.S. Appl. No. 16/575,980, dated Oct. 7, 2020.

* cited by examiner

*Primary Examiner* — Vinod Kumar
(74) *Attorney, Agent, or Firm* — Dentons US LLP

(57) ABSTRACT

Methods and materials for increasing abiotic stress tolerance in plants are disclosed. For example, nucleic acids encoding abiotic stress tolerance-increasing polypeptides are disclosed as well as methods for using such nucleic acids to transform plant cells. Also disclosed are plants having increased tolerance to abiotic stress and methods of increasing plant yield under abiotic stress conditions.

15 Claims, 45 Drawing Sheets

Specification includes a Sequence Listing.

| SEQ_ID | | | | | | |
|---|---|---|---|---|---|---|
| SEQ_ID_NO_2 | - - - - - - | - - - - - - | P P E I | F P - - | - - - - - - | 82 |
| SEQ_ID_NO_6 | - - - - - - | - - - - - - | P P E V | F P - - | - - - - - - | 87 |
| SEQ_ID_NO_8 | - - - - - - | - - - - - - | P P E V | F P - - | - - - - - - | 78 |
| SEQ_ID_NO_13 | - - - - - - | - - - - - - | A P D L | F F - - | - - - - - - | 73 |
| SEQ_ID_NO_15 | - - - - - - | - - - - - - | A P D L | F F - - | - - - - - - | 64 |
| SEQ_ID_NO_20 | - - - - - - | - - - - - - | A P C Q | G F S S D S | T V I - - - S - A | 62 |
| SEQ_ID_NO_22 | E Q G N V V | S P I L | G V - - - - | - - - - - - | - - - - - - | 101 |
| SEQ_ID_NO_24 | - - - - - - | D F S R | E M N S I N M P I I | T S H P Q F G S A S | N N G N G F C N S I | 86 |
| SEQ_ID_NO_25 | - - - - - - | D F R L | F P S S M D C A T T | S - - - - - - - T D | V H G - - - N - A | 76 |

| SEQ_ID | | | | | | |
|---|---|---|---|---|---|---|
| SEQ_ID_NO_2 | - - P - - - | A - A A | A C R V C G M E R C | L G C E G A A A - I | - - - - - - | 105 |
| SEQ_ID_NO_6 | - - P P P P T A A | C C Q L C G M E R C | L G C E F F A A - A | - - - - - - | 118 |
| SEQ_ID_NO_8 | - - A - - - | A R A E | V C G V C G M D Q C | L G C E F F A G - - | - G E G C - | 106 |
| SEQ_ID_NO_13 | - - P - - - | A R K E | A C T A C G V D G C | L G C E F F G A - X | - S G V V - | 99 |
| SEQ_ID_NO_15 | - - P - - - | A G K E | A C T A C G V D G C | L G C E F F G A - E | - A G - - - | 91 |
| SEQ_ID_NO_20 | G M P - - - | R L D S D | T C Q V C R I E G C | L G C N Y F F A P N | - A G R - - | 99 |
| SEQ_ID_NO_22 | - - P - - - | A E Q E | P C P F C R I K G C | L G C D F G T - T | Q R I E K N H Q Q | 129 |
| SEQ_ID_NO_24 | L P P - - - | S S D L D | T C G V C K I K G C | L G C N F F P P - N | S N A A - - | 117 |
| SEQ_ID_NO_25 | F L P - - - | I S D P E | P C Q F C K I K G C | L G C N F F Q E - D | Q E D K - - | 107 |

| SEQ_ID | | | | | | |
|---|---|---|---|---|---|---|
| SEQ_ID_NO_2 | - - - - - - | - - A - | L D G A E S N A A A | A P - G A A G Q R R | R R K K K N K Y R G | 135 |
| SEQ_ID_NO_6 | - - - - - - | L L P A T T A | L D G A G K A V A A | A T S A A P G Q R R | R R K K K N K Y R G | 155 |
| SEQ_ID_NO_8 | - - - - - - | S F D G A | E K V A A A A A A A | A A G A A A G Q R R | R R K K K N K Y R G | 141 |
| SEQ_ID_NO_13 | - - - - - - | - - - - - | R A V A A S D A P R | A P A A G G P Q R R | R R N K K N Q Y R G | 129 |
| SEQ_ID_NO_15 | - - - - - - | - - - - - | - A V A A S D A P R | A A T A G G P Q R R | R R N K K S Q Y R G | 120 |
| SEQ_ID_NO_20 | E E E T | S S S N - | R R R E S S P V A K | K A E G G G K I R K | R K N K K N G Y R G | 138 |
| SEQ_ID_NO_22 | - - - - - - | - - - - - | - - - - - - K - - - | N S T T - - T T A V | T K K K K N Y R G | 157 |
| SEQ_ID_NO_24 | - - - - - - | - - - - - | A V V A A D D N K K | - - D D K K G K | R K R V K K N Y R G | 134 |
| SEQ_ID_NO_25 | - - - - - - | - - - - - | - - - - - - - - - - | - - - - - - - S V A T T | T K K K K N Y R G | 122 |

Figure 1C

| SEQ_ID | | | | | Pos |
|---|---|---|---|---|---|
| SEQ_ID_NO_2 | VRQRPWGKWA | AEIRDPRRAV | RKWLGTFDTA | EEAAKAYDRA | 175 |
| SEQ_ID_NO_6 | VRQRPWGKWA | AEIRDPRRAV | RKWLGTFDTA | EEAARAYDQA | 195 |
| SEQ_ID_NO_8 | VRQRPWGKWA | AEIRDPRRAV | RKWLGTFDTA | EEAARAYDRA | 181 |
| SEQ_ID_NO_13 | VRQRPWGKWA | AEIRDPRRAV | RVWLGTFDTA | EDAARAYDRA | 169 |
| SEQ_ID_NO_15 | VRQRPWGKWA | AEIRDPRRAV | RVWLGTFDTA | EDAARAYDRA | 160 |
| SEQ_ID_NO_20 | VRQRPWGKWA | AEIRDPKRAT | RVWLGTFETA | EDAARAYDRA | 178 |
| SEQ_ID_NO_22 | VRQRPWGKFA | AEIRDPRKAA | RVWLGTFNTA | EEAARAYDKA | 197 |
| SEQ_ID_NO_24 | VRQRPWGKWA | AEIRDPRKAA | RVWLGTFNTA | EEAARAYDKA | 174 |
| SEQ_ID_NO_25 | VRQRPWGKWA | AEIRDPRRAA | RVWLGTFDTA | EAARAYDKA | 162 |

| SEQ_ID | | | | | Pos |
|---|---|---|---|---|---|
| SEQ_ID_NO_2 | AVEFRGPRAK | LNFPFPEQAA | G---RDEATS | NGDASAAARS | 212 |
| SEQ_ID_NO_6 | AIEFRGPRAK | LNFPFPEQLA | TGTGHDEA-- | --SAAATTKS | 231 |
| SEQ_ID_NO_8 | AVEFRGPRAK | LNFPFPEQLS | A---HDDS-- | NGDASAAAKS | 216 |
| SEQ_ID_NO_13 | AVEFRGPRAK | LNFSFPEQQQ | Q---QLGG-- | --SGNAAAKS | 202 |
| SEQ_ID_NO_15 | AVKFRGPRAK | LNFSFPEQHL | R---DDSG-- | ----NAAAKS | 191 |
| SEQ_ID_NO_20 | AIGFRGPRAK | LNFPFVDYTS | S---VSS--- | ----PVAADD | 208 |
| SEQ_ID_NO_22 | AIEFRGPRAK | LNFSFADYTE | L---QEQQ-- | ----SASSSS | 228 |
| SEQ_ID_NO_24 | AIDFRGPRAK | LNFPFPDSGI | A---SFEE-- | ----SKEKQE | 205 |
| SEQ_ID_NO_25 | AIDFRGPRAK | LNFPFPDNTL | L---TQNT-- | ----VETEQ | 192 |

| SEQ_ID | | | | | Pos |
|---|---|---|---|---|---|
| SEQ_ID_NO_2 | SDNT--LSPS | LCSGDAE-ER | GQPAEWPRG- | ----GGQE | 242 |
| SEQ_ID_NO_6 | SDNTLSLSPS | LCSDERER-- | GQPEWLPSA- | --GLGGQE | 266 |
| SEQ_ID_NO_8 | ---DT--LSPS | PRSADAD-EQ | VEHTRWPQGG | GGGGGGGE | 251 |
| SEQ_ID_NO_13 | DACS-PSPS | PRSADE---- | ---------- | ----DE | 218 |
| SEQ_ID_NO_15 | DACS-PSPS | PRSAEE---- | ---------- | ----EE | 207 |
| SEQ_ID_NO_20 | IGAN-ASAS | --ASV----- | ---------- | ----SA | 221 |
| SEQ_ID_NO_22 | PQQL-PEPQ | LQQGNN---- | ---------- | ----TE | 244 |
| SEQ_ID_NO_24 | KQQE-I-SE | KRSEFE---- | ---------- | ----TE | 220 |
| SEQ_ID_NO_25 | PLQE---NQ | GNSEFL---- | ---------- | ----AQ | 206 |

Figure 1D

| SEQ_ID | | | | | | | | |
|---|---|---|---|---|---|---|---|---|
| SEQ_ID_NO_2 | TGE- | ---- | ---- | QLW | EG- | ---- | LQDLMRL | 257 |
| SEQ_ID_NO_6 | TGE- | ---- | ---- | QLW | EG- | ---- | LQDLMKL | 281 |
| SEQ_ID_NO_8 | TGD- | ---- | ---- | QLW | EG- | ---- | LQDLMQL | 266 |
| SEQ_ID_NO_13 | TGD- | ---- | ---- | LLW | DG- | ---- | LVDLMKL | 233 |
| SEQ_ID_NO_15 | TGD- | ---- | ---- | LLW | DG- | ---- | LVDLMKL | 222 |
| SEQ_ID_NO_20 | TDS | VEAEQWN | GGGGDCNMEW | MN- | ---- | MMMMMDF | 250 |
| SEQ_ID_NO_22 | FGN- | ---- | ---- | EIW | DQ- | ---- | LMGDNEI | 259 |
| SEQ_ID_NO_24 | TGK- | -DN- | ---- | EFL | DNI | VDEELQE | WMAM-IMDF | 246 |
| SEQ_ID_NO_25 | TGD- | ---- | ---- | INE | NG- | ---- | FWEMIGN | 221 |

| SEQ_ID | | | | | | | | |
|---|---|---|---|---|---|---|---|---|
| SEQ_ID_NO_2 | DEAEL | WFPP | TSN- | ---- | ---- | ---- | -AWN | 272 |
| SEQ_ID_NO_6 | DEGEL | WFPP | TSS- | ---- | ---- | ---- | -AWN | 296 |
| SEQ_ID_NO_8 | DEGGL | SWFPQ | SSD- | ---- | ---- | ---- | -SWN | 282 |
| SEQ_ID_NO_13 | DESDL | CLLLP | VDNT- | DKFH- | IEGKRRSGS- | GVPLCY | 266 |
| SEQ_ID_NO_15 | DESDL | CLLLP | VDNTL | DKFH- | APGQRRSGS- | GVPLCY | 256 |
| SEQ_ID_NO_20 | GNGDS | ---- | ---- | ---- | SDSGNT- | IADMFQ | 267 |
| SEQ_ID_NO_22 | QDWLT | -M--- | MN- | FN- | GDSSDSTG- | GNVHSV | 283 |
| SEQ_ID_NO_24 | GNGGS | ---- | ---- | ---- | SNSSGTA | SAAATIGF | 266 |
| SEQ_ID_NO_25 | DQWMT | -M--- | VG- | FTG | GDSSDSATT- | GNAHSF | 247 |

Figure 2A

| SEQ_ID | | | | | | |
|---|---|---|---|---|---|---|
| SEQ_ID_NO_337 | MASFTATAAV | | SGRWGGDHT | QPPLSS | | 33 |
| SEQ_ID_NO_338 | MQTLTASSSV | | SS--IQRH- | RPH-PA--GR | ---SQSSDLS | 33 |
| SEQ_ID_NO_342 | MSSFTATAAV | | SRRWGGNHT | QPPLSSPQN- | RSSSVTFSAR | 36 |
| SEQ_ID_NO_347 | MASAAAAANL | | G--SSSSLK | RP- | --SIPMTSR | 20 |
| SEQ_ID_NO_352 | MATTTSHATN | | TW--KTKLS | MPS-SKEFGF | ASNSISLLKN | 37 |
| SEQ_ID_NO_362 | MQGLAPPTSV | | SI----HRR- | PPA-GSRAAR | GPSSVRFAPR | 34 |
| SEQ_ID_NO_364 | MQSLAPPTSV | | SI----HRQH | LPASGSSRAR | ASNSVRFSPR | 36 |
| SEQ_ID_NO_365 | MQGLAPPTSV | | SI----HRH- | LPA-RS-RAR | ASNSVRFSPR | 33 |
| SEQ_ID_NO_366 | MQTLTTPSSV | | SI----QRH- | RPR-PT-GTR | APNLVRFSAR | 33 |
| | | | | | | |
| SEQ_ID_NO_337 | Y--CISSLPMA | GRVTRKLNVS | SALHTPPALH | FPKQSSN--- | | 68 |
| SEQ_ID_NO_338 | A--VSSAPRA | PAPSRF--- | ---VR-GAD | AAP----A- | | 56 |
| SEQ_ID_NO_342 | V--QRKLN-- | ------VS | SALHTPPALH | FPKQPTN--- | | 61 |
| SEQ_ID_NO_347 | ---------- | -GKKPNTH | CSLQTPSTLH | FPKQSTT--- | | 44 |
| SEQ_ID_NO_352 | QHNRQSLN-- | -------N | SSLQAPPILH | FPKQSSNYQT | | 67 |
| SEQ_ID_NO_362 | A--VSSVPRA | APAA-R--- | PAAFKP--AE | LPAPRKH--- | | 64 |
| SEQ_ID_NO_364 | A--VSSVPRA | TAPAER--- | APFHKPGAAD | LPAQSKKP-- | | 70 |
| SEQ_ID_NO_365 | A--VSSVPPA | E---C---- | APFHKP-VAD | LPAPSRK--- | | 61 |
| SEQ_ID_NO_366 | A--LSSGAAA | RAP------ | --AHLSPFVD | APQA------ | | 56 |
| | | | | | | |
| SEQ_ID_NO_337 | ---S-P---- | AI--VVKP- | | KAK-ESNNKQ | | 85 |
| SEQ_ID_NO_338 | ---K-P---- | LI--VPK- | PPA- | --V-ERQEKK | | 74 |
| SEQ_ID_NO_342 | ---S-P---- | AI--AVNP- | | KAK-EPDTKQ | | 78 |
| SEQ_ID_NO_347 | ---YTPSST- | TI--TPTTKHPK | RDTPSPV--A | PSP-KQQQKQ | | 78 |
| SEQ_ID_NO_352 | PKN-N---- | AI--S-HPK- | QEN---N | NSS-SSSTSK | | 90 |
| SEQ_ID_NO_362 | ---A-T---- | AI--APA- | PAS--P | PRT-AGRKKE | | 85 |
| SEQ_ID_NO_364 | ---A------ | AI--VPR- | HAA--A | PRK-AGGKKQ | | 91 |
| SEQ_ID_NO_365 | ---P-A---- | AI--VPG- | HAA--A | PRKAEGGKKQ | | 83 |
| SEQ_ID_NO_366 | ---K-S---- | AI--FPK- | APAAGS | ARR-VDEKKK | | 79 |

Figure 2B

| SEQ_ID_NO_337 | MNLFQRAAAA | ALDAAEGFLV | SH- -EKLHPL | PKTADPSVQI | 123 |
| --- | --- | --- | --- | --- | --- |
| SEQ_ID_NO_338 | LNFFQRAAAT | ALDAFEEGFV | ANVLERPHGL | SRTVDPAVQI | 114 |
| SEQ_ID_NO_342 | MNLFQRAAAS | ALDAAEGLLV | SH- -ERQHPL | PKTADPSVQI | 116 |
| SEQ_ID_NO_347 | WNFLQSAAAM | ALDAVETALV | SH- -ERQHPL | PKTADPGVQI | 116 |
| SEQ_ID_NO_352 | WNLVQKAAAM | ALDAVESALT | KIH- -LEHPL | PKTADPRVQI | 128 |
| SEQ_ID_NO_362 | LNFFQRAAAA | ALDAFEEGFV | AGVLERPHGL | PRTADPAVQI | 125 |
| SEQ_ID_NO_364 | LNLFQRAAAA | ALDAFEEGFV | ANVLERPHGL | PSTADPAVQI | 131 |
| SEQ_ID_NO_365 | LNFFQRAAAA | ALDAFEEGFV | ANVLERPHGL | PSTADPAVQI | 123 |
| SEQ_ID_NO_366 | LNFFQRAAAV | ALDAFEEGFV | ANVLEKPHGL | SRTVDPAVQI | 119 |

| SEQ_ID_NO_337 | AGNFAPVNEQ | PVRRNLPVVG | KI PDSI KGVY | FTQTNRFVQE | 163 |
| --- | --- | --- | --- | --- | --- |
| SEQ_ID_NO_338 | AGNFAPVGET | PPVQALPVTG | RI PPFI NGVY | FTETERLQQE | 154 |
| SEQ_ID_NO_342 | AGNFAPVNEQ | PVRRNLPVVG | KI PDSI KGVY | FTQTNRFI QE | 156 |
| SEQ_ID_NO_347 | AGNFAPVPEQ | PVVQDLPVTG | KI PDCI QGAY | FTETNRLVQE | 156 |
| SEQ_ID_NO_352 | SGNFAPVPEN | PVCQSLPVTG | KI PKCVQGVY | FTETNRLPLE | 168 |
| SEQ_ID_NO_362 | AGNFAPVGER | PPARELPVSG | RI PPFI NGVY | FTETARLVQE | 165 |
| SEQ_ID_NO_364 | AGNFAPVGER | PPVRELPVSG | RI PPFI NGVY | FTETARLRQE | 171 |
| SEQ_ID_NO_365 | AGNFAPVGER | PPVHELPVSG | RI PPFI DGVY | FTETARLTQE | 163 |
| SEQ_ID_NO_366 | AGNFAPVGET | PPVQSLPVSG | RI PPFI NGVY | FTDTERLRQE | 159 |

| SEQ_ID_NO_337 | PVTGHHFFDG | DGMVHAVKFE | DGSA- SYACR | FTQTNRFVQE | 202 |
| --- | --- | --- | --- | --- | --- |
| SEQ_ID_NO_338 | PVAGHHLFDG | DGMVHALRI R | NGVAETYASR | FTETERLQQE | 194 |
| SEQ_ID_NO_342 | PVTGHHFFDG | DGMVHAVKFE | DGTA- SYACR | FTQTNRFI QE | 195 |
| SEQ_ID_NO_347 | PVAGHHFFDG | DGMVHAVQFK | KGSV- SYSSR | FTETNRLVQE | 195 |
| SEQ_ID_NO_352 | PTAGHHFFDG | DGMVHAVQFK | NGSA- SYACR | FTETNRLVQE | 207 |
| SEQ_ID_NO_362 | PVAGHHLFDG | DGMVHALRI R | NGVAESYACR | FTETARLRQE | 205 |
| SEQ_ID_NO_364 | PVAGHHLFDG | DGMVHALRI R | NGVAESYACR | FTETARLTQE | 211 |
| SEQ_ID_NO_365 | PVAGHHLFDG | DGMVHALRI R | NGAAESYACR | FTETARLRQE | 203 |
| SEQ_ID_NO_366 | PVAGHHLFDG | DGMVHALRI R | NGVAETYASR | FTDTERLRQE | 199 |

Figure 2C

| | | | | | |
|---|---|---|---|---|---|
| SEQ_ID_NO_337 | RQL GRPVFPK | AI GELHGHTG | I ARLMLFYAR | AAAGI VGPAH | 242 |
| SEQ_ID_NO_338 | RAL GRPMFPK | AI GELHGHSG | I ARLALFYAR | AACGLIDPSR | 234 |
| SEQ_ID_NO_342 | RRL GRPVFPK | AI GELHGHTG | I ARLMLFYAR | AAAGLVDPAH | 235 |
| SEQ_ID_NO_347 | RGL GRPLFPK | AI GELHGHSG | I ARLLFYAR | GAFGI VDPSH | 235 |
| SEQ_ID_NO_352 | KAL GRPVFPK | AI GELHGHSG | I ARLMLFYAR | GLFGLVDHSK | 247 |
| SEQ_ID_NO_362 | RAI GRPVFPK | AI GELHGHSG | I ARLALFYAR | AACGLVDPSH | 245 |
| SEQ_ID_NO_364 | RAI GRPVFPK | AI GELHGHSG | I ARLALFYAR | AACGLVDPSA | 251 |
| SEQ_ID_NO_365 | RAI GRPVFPK | AI GELHGHSG | I ARLALFYAR | AACGLVDPSA | 243 |
| SEQ_ID_NO_366 | RAL GRPMFPK | AI GELHGHSG | I ARLALFYAR | SACGLVDPSR | 239 |

| | | | | | |
|---|---|---|---|---|---|
| SEQ_ID_NO_337 | GT GVANAGLV | YFNGRLLAMS | EDDLPYQVRI | TPNGDLKTVG | 282 |
| SEQ_ID_NO_338 | GT GVANAGLV | YFNGHLLAMS | EDDIPYHVRV | TDDGDLQTVG | 274 |
| SEQ_ID_NO_342 | GT GVANAGLV | YFNNRLLAMS | EDDLPYQVRI | TPSGDLKTVG | 275 |
| SEQ_ID_NO_347 | GT GVANAGLV | YFDGHLLAMS | EDDLPYHVRV | LPSGDLKTVG | 275 |
| SEQ_ID_NO_352 | GT GVANAGLV | YFNNRLLAMS | EDDLPYHVKV | TPTGDLKTEG | 287 |
| SEQ_ID_NO_362 | GT GVANAGLV | YFNGHLLAMS | EDDLPYHVRV | TDGGDLETVG | 285 |
| SEQ_ID_NO_364 | GT GVANAGLV | YFNGHLLAMS | EDDLPYHVRV | ADDGDLETVG | 291 |
| SEQ_ID_NO_365 | GT GVANAGLV | YFNGRLLAMS | EDDLPYHVRV | ADDGDLETVG | 283 |
| SEQ_ID_NO_366 | GT GVANAGLV | YFNGHLLAMS | EDDIPYHVRV | TEAGDLQTVG | 279 |

| | | | | | |
|---|---|---|---|---|---|
| SEQ_ID_NO_337 | RFNFDGQLES | TMI AHPKVDP | ESGELFALSY | DVVSKPYLKY | 322 |
| SEQ_ID_NO_338 | RYDFDGQLEC | PMI AHPKLDP | ATGELHALSY | DVI KKPYLKY | 314 |
| SEQ_ID_NO_342 | RYDFNGQLES | TMI AHPKVDP | ESGELFALSY | DVVSKPFLKY | 315 |
| SEQ_ID_NO_347 | RYDFDGQLKT | TMI AHPKVDP | VSGELFALSY | DVVQKPYLKY | 315 |
| SEQ_ID_NO_352 | RFDFDGQLKS | TMI AHPKVDP | VSGELFALSY | DVI QKPYLKY | 327 |
| SEQ_ID_NO_362 | RYDFDGQLGC | AMI AHPKLDP | ATGELHALSY | DVI KKPYLKY | 325 |
| SEQ_ID_NO_364 | RYDFDGQLGC | AMI AHPKLDP | VTGELHALSY | DVI KKPYLKY | 331 |
| SEQ_ID_NO_365 | RYDFDGQLGC | AMI AHPKLDP | ATGELHALSY | DVI KRPYLKY | 323 |
| SEQ_ID_NO_366 | RYDFDGQLEC | PMI AHPKLDP | ATGQLHALSY | DVI KKPYLKY | 319 |

Figure 2D

| SEQ_ID | Sequence | End |
|---|---|---|
| SEQ_ID_NO_337 | FRFSPDGTKS PDVEI QLDQP TMMHDFAI TE NFVVVPDQQV | 362 |
| SEQ_ID_NO_338 | FYFAADGTKS ADVEI PLDQP TMI HDFAI TE NYVVVPDHQV | 354 |
| SEQ_ID_NO_342 | FRFSPEGI KS PDVEI NLDQP TMMHDFAI TE NFVVI PDQQV | 355 |
| SEQ_ID_NO_347 | FRFSPDGKKS PNVEI PLDQP TMMHDFAI TE NFVVI PDQQV | 355 |
| SEQ_ID_NO_352 | FRFSKNGEKS NDVEI PVEDP TMI HDFAI TE NFVVI PDQQV | 367 |
| SEQ_ID_NO_362 | FYFRPDGTKS DDVEI PLDQP TMI HDFAI TE NFVVVPDHQV | 365 |
| SEQ_ID_NO_364 | FYFRPDGTKS DDVEI PLDQP TMI HDFAI TE NFVVVPDHQV | 371 |
| SEQ_ID_NO_365 | FYFRPDGTKS DDVEI PLEQP TMI HDFAI TE NLVVVPDHQV | 363 |
| SEQ_ID_NO_366 | FYFAADGTKS ADVEI PLDQP TMI HDFAI TE NFVVVPDHQV | 359 |

| SEQ_ID | Sequence | End |
|---|---|---|
| SEQ_ID_NO_337 | VFKLPEMI RG GSPVVYDKNK VARFGI LDKY AEDSSNI KWI | 402 |
| SEQ_ID_NO_338 | VFKLQEMLRG GSPVVLDKEK TSRFGVLDKY AADASEMVVW | 394 |
| SEQ_ID_NO_342 | VFKLPEMI RG GSPVVYDKEK VARFGVLDKY AGDSSAI RWI | 395 |
| SEQ_ID_NO_347 | VFKLPEMI RG GSPVI YDKNK MARFGVLDKN ATDASNI RWI | 395 |
| SEQ_ID_NO_352 | VFKMSEMI RG GSPVVYDKNK VSRFGI LDKY AKDGSDLKWV | 407 |
| SEQ_ID_NO_362 | VFKLQEMLRG GSPVVLDKEK TSRFGVLPKH AKDASEMAWV | 405 |
| SEQ_ID_NO_364 | VFKLQEMLRG GSPVVLDKEK TSRFGVLPKH ASDASEMVVW | 411 |
| SEQ_ID_NO_365 | VFKLQEMLRG GSPVVLDKEK TSRFGVLPKH AADASEMAWV | 403 |
| SEQ_ID_NO_366 | VFKLQEMLRG GSPVVLDKEK TSRFGVLPKC AADASEMVW | 399 |

| SEQ_ID | Sequence | End |
|---|---|---|
| SEQ_ID_NO_337 | DAPDCFCFHL WNAWEEPETD EVVVI GSCMT PPDSI FNESD | 442 |
| SEQ_ID_NO_338 | DVPDCFCFHL WNAWEEETD EVVVI GSCMT PADSI FNESD | 434 |
| SEQ_ID_NO_342 | EAQECFCFHL WNAWEEPETE EI VVI GSCMT PPDSI FNEAD | 435 |
| SEQ_ID_NO_347 | ETPDCFCFHL WNAWEEPETD EI VVI GSCMT PPDSI FNECD | 435 |
| SEQ_ID_NO_352 | EVPDCFCFHL WNAWEEAETD EVVVI GSCMT PPDSI FNECD | 447 |
| SEQ_ID_NO_362 | DVPDCFCFHL WNAWEDEETG EVVVI GSCMT PADSI FNESD | 445 |
| SEQ_ID_NO_364 | DVPDCFCFHL WNAWEDEATG EVVVI GSCMT PADSI FNESD | 451 |
| SEQ_ID_NO_365 | DVPDCFCFHL WNAWEDEATG EVVVI GSCMT PADSI FNESD | 443 |
| SEQ_ID_NO_366 | DVPDCFCFHL WNAWEEDTD EVVVI GSCMT PADSI FNESD | 439 |

Figure 2E

| SEQ_ID_NO | | | | | | |
|---|---|---|---|---|---|---|
| SEQ_ID_NO_337 | ENLKGVLSEI | RLNLKTGEST | RRPIISNEDQ | QVNLEAGMVN | 482 |
| SEQ_ID_NO_338 | ECLESVLTEI | RLNTRTGEST | RRPILALLSE | QVNLEVGMVN | 473 |
| SEQ_ID_NO_342 | ENLESVLSEI | RLNLRTGEST | RRPIISDGEE | QVNLEAGMVN | 475 |
| SEQ_ID_NO_347 | ESLKSVLSEI | RLNLKTGKST | RRQILSEAD  | QVNLEAGMVN | 474 |
| SEQ_ID_NO_352 | EGLKSVLSEI | RLNLKTGKST | RKSIIENPDE | QVNLEAGMVN | 487 |
| SEQ_ID_NO_362 | EHLESVLTEI | RLDTRTGRSS | RRAILPPSQ  | QVNLEVGMVN | 484 |
| SEQ_ID_NO_364 | ERLESVLTEI | RLDTRTGRST | RRAVLPPSQ  | QVNLEVGMVN | 490 |
| SEQ_ID_NO_365 | ERLESVLTEI | RLDARTGRST | RRAVLPPSQ  | QVNLEVGMVN | 482 |
| SEQ_ID_NO_366 | ECLESVLTEI | RLNTRTGEST | RRPILAPSQ  | QVNLEVGMVN | 478 |

| SEQ_ID_NO | | | | | | |
|---|---|---|---|---|---|---|
| SEQ_ID_NO_337 | RNVLGRKTKF | AYLALAEPWP | KVSGFAKVDL | TTGEVKKHLY | 522 |
| SEQ_ID_NO_338 | SNLLGRKTRY | AYLAVAEPWP | KVSGFAKVDL | ATGELTKFEY | 513 |
| SEQ_ID_NO_342 | RNMLGRKTRF | AYLALAEPWP | KVSGFAKVDL | FTGEVKKYLY | 515 |
| SEQ_ID_NO_347 | RNLLGRKSRF | AYLAIAEPWP | KVSGFAKVDL | STGEVHKYIY | 514 |
| SEQ_ID_NO_352 | RNKLGRKTEY | AYLALAEPWP | KVSGFAKVNL | FTGEVEKFIY | 527 |
| SEQ_ID_NO_362 | RNLLGRKTRY | AYLAVAEPWP | KVSGFAKVDL | ATGELTKFEY | 524 |
| SEQ_ID_NO_364 | RNLLGRKTRY | AYLAVAEPWP | KVSGFAKVDL | ETGELTKFEY | 530 |
| SEQ_ID_NO_365 | RNLLGRETRY | AYLAVAEPWP | KVSGFAKVDL | STGELTKFEY | 522 |
| SEQ_ID_NO_366 | STLLGRKTRY | AYLAVAEPWP | KVSGFAKVDL | ATGELTKFDY | 518 |

| SEQ_ID_NO | | | | | | |
|---|---|---|---|---|---|---|
| SEQ_ID_NO_337 | GDNRYGGEPL | FLPGEG---- | -GEEDEGYIL | CFVHDEKTWK | 557 |
| SEQ_ID_NO_338 | GEGRFGGEPC | FVPMDPAT-- | SRGEDDGYIL | TFVHDEAAGT | 551 |
| SEQ_ID_NO_342 | GGDRYGGEPL | FLPGDEN--- | -RAEDDGYIL | CFVHDEETWK | 551 |
| SEQ_ID_NO_347 | GDQKFGGEPL | FLPRDPNS-- | -EREDDGYIL | AFVHDEKEWK | 551 |
| SEQ_ID_NO_352 | GDNKYGGEPL | FLPRDPNS-- | -KEEDDGYIL | TFVHDEKEWK | 564 |
| SEQ_ID_NO_362 | GEGRFGGEPC | FVPMDPAAAH | PRGEDDGYVL | TFVHDERAGT | 564 |
| SEQ_ID_NO_364 | GEGRFGGEPC | FVPMDPSAAH | PRGEDDGYVL | TFVHDERAGT | 570 |
| SEQ_ID_NO_365 | GEGRFGGEPC | FVPMDPAAAH | PRGEDDGYVL | TFVHDERAGT | 562 |
| SEQ_ID_NO_366 | GEGRFGGEPC | FVPMDPAAAS | PRGEDDGYIL | TFVHDERAGT | 558 |

Figure 2F

| SEQ_ID | | | | | |
|---|---|---|---|---|---|
| SEQ_ID_NO_337 | SELQIVNAVS | LEVEATVKLP | SRVPYGFHGT | FIGADDLAKQ | 597 |
| SEQ_ID_NO_338 | SELLVVNAAD | MRLEATIQLP | SRVPYGFHGT | FITGKELESQ | 591 |
| SEQ_ID_NO_342 | SELQIVNAVS | LEVEATVKLP | SRVPYGFHGT | FIGANDLATQ | 591 |
| SEQ_ID_NO_347 | SELQIVNAMN | LKLEATVKLP | SRVPYGFHGT | FIGAKDLEKQ | 591 |
| SEQ_ID_NO_352 | SELQIVNAMS | LKLEATVQLP | SRVPYGFHGT | FINANDLANQ | 604 |
| SEQ_ID_NO_362 | SELLVVNAVD | MRLEATVQLP | SRVPFGFHGT | FITASELEAQ | 604 |
| SEQ_ID_NO_364 | SELLVVNAAD | MRLEATVQLP | SRVPFGFHGT | FITGKELEAQ | 610 |
| SEQ_ID_NO_365 | SELLVVNAAD | MRLEATVQLP | SRVPFGFHGT | FITGQELEAQ | 602 |
| SEQ_ID_NO_366 | SELLVVNAAD | MRLEATIQLP | SRVPYGFHGT | FVKASELESQ | 598 |

| SEQ_ID | | |
|---|---|---|
| SEQ_ID_NO_337 | VV | 599 |
| SEQ_ID_NO_338 | -A | 592 |
| SEQ_ID_NO_342 | -V | 592 |
| SEQ_ID_NO_347 | -A | 592 |
| SEQ_ID_NO_352 | -A | 605 |
| SEQ_ID_NO_362 | -A | 605 |
| SEQ_ID_NO_364 | -A | 611 |
| SEQ_ID_NO_365 | AA | 604 |
| SEQ_ID_NO_366 | -A | 599 |

Figure 3A

| | | | | | |
|---|---|---|---|---|---|
| SEQ_ID_NO_61 | MSE------ | EKRKQHFVLV | HGACHGAWCW | YKVKPLLEAL | 33 |
| SEQ_ID_NO_82 | MEVD----- | RKQGRHFVLV | HGACHGAWSW | YKVKPRLEAA | 34 |
| SEQ_ID_NO_71 | MEEV----- | GMEEKHFVLV | HGVNHGAWCW | YKLKARLVAG | 35 |
| SEQ_ID_NO_88 | MVE------ | TKNQKHFVLV | HGACHGAWCW | QKFKTLLESA | 33 |
| SEQ_ID_NO_86 | MK------- | --EGKHFVLV | HGACHGAWCW | YKLKPLLEAA | 30 |
| SEQ_ID_NO_98 | MEAN----- | KKQGKHFVLV | HGAGHGAWCW | YKLKPLLEAA | 34 |
| SEQ_ID_NO_89 | MHSAA---- | AKQQKHFVLV | HGGCLGAWLW | YKLKPLLESA | 36 |
| SEQ_ID_NO_108 | ME------- | --VMKHFVTV | HGVGHGAWYY | YKLKPRIEAA | 30 |
| SEQ_ID_NO_81 | MNYGEGRGDG | SCNKKHDLV | HGACHGAWSW | HKVTTQLRSA | 40 |
| SEQ_ID_NO_96 | M-------- | QSKHYMVV | HGMSHGAWCW | YKLKPLLESA | 29 |
| SEQ_ID_NO_77 | MS------- | PTKHFVAV | HGVGHGAWYY | YKLKPRIEAA | 30 |

| | | | | | |
|---|---|---|---|---|---|
| SEQ_ID_NO_61 | GHRVTALDLA | ASGI DTTRSI | TDISTCEQYS | EPLMQLMTSL | 73 |
| SEQ_ID_NO_82 | GHRVTALDMA | ASGI NR-KQI | QEVHSMHEYS | QPLLEMMATL | 73 |
| SEQ_ID_NO_71 | GHRVTAVDLA | ASGI NM-KRI | EDVHTFHAYS | EPLMEVLASL | 74 |
| SEQ_ID_NO_88 | SNRVTVLDLA | ASGANM-KAI | QDVETLDEYT | EPLLEFLASL | 72 |
| SEQ_ID_NO_86 | GHKVTALDLA | ASGTDL-RKI | EELRTLYDYT | LPLMELMESL | 69 |
| SEQ_ID_NO_98 | GHKVTALDLA | ASGI DL-RKI | EQLHTLHDYT | LPLLELMESL | 73 |
| SEQ_ID_NO_89 | GHKVTAVDLS | AAGI NP-RRL | DEI HTFRDYS | EPLMEVMASI | 75 |
| SEQ_ID_NO_108 | GHRCTAVNLA | ASGI NE-KKL | EEVRSSI DYA | APLLEVLDSV | 69 |
| SEQ_ID_NO_81 | GYQVTVPDLA | ASGVDE-RRF | QDLRSFIHYS | QPLLDI LACL | 79 |
| SEQ_ID_NO_96 | GHRTALDMG | ASGVNM-RPV | EELRSFRDYN | APLSFMSSL | 68 |
| SEQ_ID_NO_77 | GFKFTAIDLA | AAGVNP-KKL | EEVNSLEEYC | GPLFDVLAAV | 69 |

Figure 3B

| SEQ_ID_NO_61 | PNDEKVVLVG | HSFGGLSLAL | AMDKFPDKIS | VSVFVTAFMP | 113 |
|---|---|---|---|---|---|
| SEQ_ID_NO_82 | PPNEKVILVG | HSLGGLNLAV | AMEKFPEKVS | VAVFLTAFMP | 113 |
| SEQ_ID_NO_71 | PAEEKVILVG | HSLGGVTLAL | AGDKFPHKIS | VAVFVTAFMP | 114 |
| SEQ_ID_NO_88 | QPKEKVILVG | HSLGGLSLAL | AMEKFPEKIA | VAVFLSAFMP | 112 |
| SEQ_ID_NO_86 | SADEKVILVG | HSLGGMNLGL | AMEKYPQKIY | AAVFLAAFMP | 109 |
| SEQ_ID_NO_98 | PQEEKAILVG | HSLGGMNLAL | AMEKYPKKIY | AAVFLAAFMP | 113 |
| SEQ_ID_NO_89 | PPDEKVVLLG | HSFGGMSLGL | AMETYPEKIS | VAVFMSAMMP | 115 |
| SEQ_ID_NO_108 | PENEKVILVG | HSGGGMTAAV | GMEKFPNKIS | LAVFLNAIMP | 109 |
| SEQ_ID_NO_81 | PPGERVILVG | HSLGGLNIAL | AMDRFPEKIA | AAVFVTALMP | 119 |
| SEQ_ID_NO_96 | PEDDKVVLVG | HSLGGINIAF | AMEEFPEKVS | AAVFVAALVP | 108 |
| SEQ_ID_NO_77 | PEGEKVILVG | HSGGGLSAAV | GMEKFPKKIS | VAVFLNAIMP | 109 |
| SEQ_ID_NO_61 | DTKHSPSFVE | EKFASSMT-- | PEGWMGSELE | TYGSDDNSL-GL | 150 |
| SEQ_ID_NO_82 | DTLHRPSYVL | DQYVERTP-- | NDAWLDTQFS | PYGSSEKPQN | 151 |
| SEQ_ID_NO_71 | DTTHRPSFVL | EQYSEKMGKE | DDSWLDTQFS | QCDASNPSHI | 154 |
| SEQ_ID_NO_88 | DTTHKPSFVL | DQYNERTP-- | ADSWLDTQFL | PYSSSQSHLT | 150 |
| SEQ_ID_NO_86 | DSVHNSSFVL | EQYNERTP-- | AENWLDTQFL | PYGSPEEPLT | 147 |
| SEQ_ID_NO_98 | DSLHLSSYYM | DQYNERTP-- | AENWLDTQFL | PYGTPEEPLT | 151 |
| SEQ_ID_NO_89 | DPNHSLTYPF | EKYNEKCP-- | ADMMLDSQFS | TYGNPENPGM | 153 |
| SEQ_ID_NO_108 | DTENRPSYVL | EEYTAKTP-- | PEAWKDCQFS | AYGDP--PIT | 145 |
| SEQ_ID_NO_81 | DSVNPPSYVM | DKLKKEKT-- | MLFWSDTQFG | LVGDEDKGPV | 157 |
| SEQ_ID_NO_96 | DTVNKPSFFL | DELFKKLG-A | ANGWLDCQFS | TFGSPDEPVT | 147 |
| SEQ_ID_NO_77 | DTKNRPSYVM | EEYTARTP-- | IEAWKDTQFS | AYGEP--PIT | 145 |

Figure 3C

| SEQ_ID_NO_61 | SVFFSTDFMK | HRLYQLSPVE | DLELGLLLKR | PSSLFINELS | 190 |
| --- | --- | --- | --- | --- | --- |
| SEQ_ID_NO_82 | SMFFGPEFIS | TKLYQLSPIE | DLELVLALAR | PASLFLEDLA | 191 |
| SEQ_ID_NO_71 | SMLFGREFLT | IKIYQLCPPE | DLELAKMLVR | PGSMFIDNLS | 194 |
| SEQ_ID_NO_88 | TMSFGPKFLS | SKLYQLSPPE | DLEQAKTMVR | PGSLFLYDLS | 190 |
| SEQ_ID_NO_86 | SMFFGPKFLA | HKLYQLCSPE | DLALASSLVR | PSSLFMEDLS | 187 |
| SEQ_ID_NO_98 | SMTFGPKFLA | DKLYRLSPPE | DVALGLSLVR | TSSLFLEDLS | 191 |
| SEQ_ID_NO_89 | SMILGPQFMA | LKMFQNCSVE | DLELAKMLTR | PGSLFFQDLA | 193 |
| SEQ_ID_NO_108 | SLVCGPEFIS | STLYHLSPIE | DHALGKILVR | PGSLFIEDLL | 185 |
| SEQ_ID_NO_81 | SLLFGPKFLS | -KLYTRSPPE | DLTLARTLMR | PSSFFLEDLG | 196 |
| SEQ_ID_NO_96 | VISFGPKFLS | -LLYDSSPIE | DYELAKMLTR | PLPNYVTDLG | 186 |
| SEQ_ID_NO_77 | ALLCGPEFIS | TSLYHLSPVE | DHTLGKLLVR | PGALFVEDLL | 185 |

| SEQ_ID_NO_61 | K-MENFSEKG | YGSVPRAYIV | CKEDNISED | HQRVMIHNY- | 228 |
| --- | --- | --- | --- | --- | --- |
| SEQ_ID_NO_82 | E-LKKFSNEG | YGSVTSVFIR | CDKDEAIRKE | FQQWMIENSG | 230 |
| SEQ_ID_NO_71 | K-ESKFSDEG | YGSVKRVYLV | CEEDIGLPKQ | FQHWMIQNY- | 232 |
| SEQ_ID_NO_88 | K-ANSFSTTG | YGSVKRVYVI | CDEDLAIPEE | FQRWMIENS- | 228 |
| SEQ_ID_NO_86 | K-AKYFTDER | FGSVKRVYIV | CTEDKGIPEE | FQRWQIDNI- | 225 |
| SEQ_ID_NO_98 | K-AKYLTDEG | YGSVKRVYVV | CTEDKGISKE | FQQWQIDNI- | 229 |
| SEQ_ID_NO_89 | K-AKKFSTER | YGSVKRAYIF | CNEDKSFPVE | FQKWFVESV- | 231 |
| SEQ_ID_NO_108 | K-AEKFTEEG | FGSVPRVYVI | AAEDKTIPPE | FQRWMIENN- | 223 |
| SEQ_ID_NO_81 | S-MPPFSESG | YGSVEKIYVV | CAQDEILTEG | FQRWMIENN- | 234 |
| SEQ_ID_NO_96 | K-AEKLSDGK | YGSVRRVYVI | CKEDKAIPDE | LVGQMIEWN- | 224 |
| SEQ_ID_NO_77 | KGAVKFTDEG | FGSVPRVYVV | ATEDKTIPPE | FQRVMIENN- | 224 |

Figure 3D

| SEQ_ID_NO_61 | PANLVIEMEE | TDHMPMFCKP | QVLSDHLLAI | ADNFS | 263 |
|---|---|---|---|---|---|
| SEQ_ID_NO_82 | GVKEVMNIKD | ADHMAMFSKP | EELCACLLEV | AHKYG | 265 |
| SEQ_ID_NO_71 | PVNEVMEIKG | GDHMAMLSDP | QKLCDCLSQI | SLKYA | 267 |
| SEQ_ID_NO_88 | AVEEVMEIEG | ADHMVMFSKP | QELFHCLSEI | ANKHA | 263 |
| SEQ_ID_NO_86 | GVTEAIEIKG | ADHMAMLCEP | QKLCASLLEI | AHKYN | 260 |
| SEQ_ID_NO_98 | GVTEAKEIKG | ADHMAMLCMP | KKLCDTLVEI | ADKYN | 264 |
| SEQ_ID_NO_89 | GADKVKEIKE | ADHMGMLSQP | REVCKCLLDI | SD--S | 264 |
| SEQ_ID_NO_108 | PVKEVKEIKG | ADHMPMFSKP | DELSQCLLDI | AKKHA | 258 |
| SEQ_ID_NO_81 | PVKEVRELED | ADHMPMFSTP | KQLFQCLSDV | ADACA | 269 |
| SEQ_ID_NO_96 | GLKEVIELQG | ADHMPMLSNP | QQLCDCLVQI | AVENP | 259 |
| SEQ_ID_NO_77 | PVAEVKEIEG | ADHLPQFSKP | DELTQVLVDI | AKNHG | 259 |

Figure 4A

| SEQ_ID_NO_111 | MGKRGKWFSA | VKKVFSSSDP | DGKEAKAQKA | DKSKSKRRWP | 40 |
|---|---|---|---|---|---|
| SEQ_ID_NO_113 | MGKKGKWFSA | VKKVFSSSDP | DGKEAKAEKA | DKSKSKRRWP | 40 |
| SEQ_ID_NO_115 | MGKKGKWFSA | VKKVFGSSDP | DGKQAKAEKA | DKSKSRRRWP | 40 |
| SEQ_ID_NO_116 | MGKKGNWFSA | VKKVFSSSDP | DGREAKIEKA | DKSRSRRKWP | 40 |
| SEQ_ID_NO_117 | MGKKGKWFSA | VRRVFSSSDP | EAKEAKAEKA | DKPKSRKKWP | 40 |
| SEQ_ID_NO_118 | MGKKGNWFSA | VKKALSPE-- | PKEKKDK--- | TTPKSKKKW- | 34 |
| SEQ_ID_NO_120 | MGKRGSWFSA | LKKALGSSK- | SKKSQH---- | KSKSKKKW-- | 27 |
| SEQ_ID_NO_122 | MGKKGGWLSL | VKKALSPE-- | --------- | QTPKPKKKW- | 33 |
| SEQ_ID_NO_123 | MGKKGSWFSA | VKKVFSSDS- | PKQKKE---- | KKDKKQK--- | 27 |
| SEQ_ID_NO_124 | MGK--SWFSA | VKKALSPE-- | PKQKKE---- | QKPHKSKKW- | 31 |

| SEQ_ID_NO_111 | FGKSKI-HSEP | SISTVPGTAP | AVAPLP---- | PPA---TQPH | 73 |
|---|---|---|---|---|---|
| SEQ_ID_NO_113 | FGKTKK-HSEP | SISTVAGTAP | VAPLP----- | PPPL--TQPH | 73 |
| SEQ_ID_NO_115 | FGKSRI-HSDP | SASTVSGTAP | VAPLP----S | PPPL--TQPH | 75 |
| SEQ_ID_NO_116 | FGKSKI-KSDP | WTSTVAVPTS | TAPPPQPPPP | PPPTHPIQPQ | 78 |
| SEQ_ID_NO_117 | FGKSKI-HSDL | PTSTVSGITL | VAPQP---LP | PPPTQPPQPQ | 76 |
| SEQ_ID_NO_118 | FGKHK-NLDP | VSSSTENA-- | --MPLP---A | PA-------- | 58 |
| SEQ_ID_NO_120 | SEKEK-NRDL | GVSSHEET-- | VAPSL----S | PPR------- | 56 |
| SEQ_ID_NO_122 | FGKSKI-NLSP | VSVPEETE-- | EIAAV----L | -------TPP | 50 |
| SEQ_ID_NO_123 | SDKSKI-KAL- | --SSDKDA-- | ---------- | P--------- | 47 |
| SEQ_ID_NO_124 | FGKSKI-KLDV | -TNSGAAYS- | ---------- | ---------- | 48 |

| SEQ_ID_NO_111 | SLEIKDVNPV | ETDSEQNKHA | YSVALASAVA | AEAAAVAAQA | 113 |
|---|---|---|---|---|---|
| SEQ_ID_NO_113 | SLEIKDVNPL | ETDSEQNKHA | YSVALASAVA | AEAAAVAAQA | 113 |
| SEQ_ID_NO_115 | SQEIKDVKPV | ETDSEQNKHA | YSVALASAVA | AEAAAVAAQA | 115 |
| SEQ_ID_NO_116 | PEEIKDVKAV | EAESEQNKHA | YSVALASAVA | AEAAAVAAQA | 118 |
| SEQ_ID_NO_117 | SEEIKDVKTI | EAENEQNKHA | YSVALATAVA | AEAAAVAAQA | 116 |
| SEQ_ID_NO_118 | -PPIEDVKLT | EAENEQSKHA | YSVALATAVA | AEAAAVAAHA | 97 |
| SEQ_ID_NO_120 | PPTAEDVKLT | EAENEQSKHA | YSVALATAVA | AEAAAVAAQA | 96 |
| SEQ_ID_NO_122 | -VITEDAKLK | EAEKEQSKHA | YSVALATAVA | AEAAAVAAQA | 89 |
| SEQ_ID_NO_123 | --PIEDAKLI | EIEEQQSRHA | ASLAFATAVA | AEAAAVAAQA | 85 |
| SEQ_ID_NO_124 | PRTVKDAKLK | ---------- | YSVALATAIA | AEAAAVAAQA | 88 |

Figure 4B

| SEQ_ID_NO | | | | | | |
|---|---|---|---|---|---|---|
| SEQ_ID_NO_111 | AAEVVRLTAV | TTAAPKMPVS | SREELAATKI | QTAFRGYLAR | 153 |
| SEQ_ID_NO_113 | AAEVVRLTAV | TTAAPKMPVS | SMEELAATKI | QTAFRGYLAR | 153 |
| SEQ_ID_NO_115 | AAEVVRLTAV | TTAAPKMPVT | SREELAAIKI | QTAFRGYLAR | 155 |
| SEQ_ID_NO_116 | AAEVVRLTTA | TTAVPKSPVS | SKDELAAIKI | QTAFRGYLAR | 158 |
| SEQ_ID_NO_117 | AAEVVRLTTV | TTSTPKAAVC | SKEELAAVKI | QTAFRGYLAR | 156 |
| SEQ_ID_NO_118 | AAEVVRLTTV | TF----RFSGK | SKEEI AAI KI | QTAFRGYLAR | 133 |
| SEQ_ID_NO_120 | AAEVVRLTSQ | A----HYSGK | SKEEI AAI RI | QTAFRGYLAR | 132 |
| SEQ_ID_NO_122 | AAEVVRLTSM | P----RHLGK | SKEEI AAI RI | QTAFRGYLAR | 125 |
| SEQ_ID_NO_123 | AAEVVRLTSM | P----HYTGR | TKEEI AAI KV | QTAFRGYMAR | 121 |
| SEQ_ID_NO_124 | AAEVVRLSAL | S----RFPGK | SMEEI AAI KI | QTAFRGYMAR | 124 |

| SEQ_ID_NO | | | | | | |
|---|---|---|---|---|---|---|
| SEQ_ID_NO_111 | RALRALRGLV | RLKSLVDGNA | VKRQTAHTLQ | CTQAMTRVQT | 193 |
| SEQ_ID_NO_113 | RALRALRGLV | RLKSLVDGNA | VKRQTAHTLQ | CTQTMTRVQT | 193 |
| SEQ_ID_NO_115 | RALRALRGLV | RLKSLVDGHA | VKRQTAHTLH | CTQTMTRVQA | 195 |
| SEQ_ID_NO_116 | RALRALRGLV | RLKSLVDGNA | VKRQTAHTLH | CTQTMTRVQT | 198 |
| SEQ_ID_NO_117 | RALRALRGLV | RLKSLVDGNS | VKRQTSHTLH | CTQTMTRVQT | 196 |
| SEQ_ID_NO_118 | RALRALRGLV | RLKSLI QGQS | VKRQATTTLR | CMQTLARVQS | 173 |
| SEQ_ID_NO_120 | RALRALRGLV | RLKSLI QGQS | VKRQATATLR | AMQTLARVQS | 172 |
| SEQ_ID_NO_122 | RALRALRGLV | RLKSLI RGQS | VKRQATTTLR | CMQTLARLQS | 165 |
| SEQ_ID_NO_123 | RALRALRGLV | RLKTLVQGQS | VKRQAASTLR | SMQTLARLQS | 161 |
| SEQ_ID_NO_124 | RALRALRGLV | RLKSLVQGKC | VRRQATSTLQ | SMQTLARVQY | 164 |

| SEQ_ID_NO | | | | | | |
|---|---|---|---|---|---|---|
| SEQ_ID_NO_111 | QI YSRRVKLE | EEKQALQRQL | QLKHQRELEK | MK---I DEDWD | 231 |
| SEQ_ID_NO_113 | QI YSRRVKLE | EEKQALQRQL | QLKHQRELEK | MK---I DEDWD | 231 |
| SEQ_ID_NO_115 | QI YSRRVKLE | EEKQALQRQL | QLKHQRELEK | MK---I DEDWD | 233 |
| SEQ_ID_NO_116 | QI YSRRVKME | EEKQALQRQL | QLKHQRELEK | MK---I DEDWD | 236 |
| SEQ_ID_NO_117 | QI YSRRVKLE | EEKQALQRQL | QLKHQRELEK | MK---I DEDWD | 234 |
| SEQ_ID_NO_118 | QI RARRI RMS | EENLALQRQL | QLKRDKELEK | LRASMGDDWD | 213 |
| SEQ_ID_NO_120 | QI RARRI RMS | EENEALQRQL | QQKHDKELEK | LRTSI GEQWD | 212 |
| SEQ_ID_NO_122 | EI SARRI RMS | EENQALQRQL | QQKCQKELEK | LRAPMREDWN | 205 |
| SEQ_ID_NO_123 | QI RERRI RMS | EENQALQRQL | HQKHEKELEK | LRAAVGEEWD | 201 |
| SEQ_ID_NO_124 | QI RERRLRLS | EDKQALTRQL | QQKHNKDFDK | T----GENWN | 200 |

| | | | | | | |
|---|---|---|---|---|---|---|
| SEQ_ID_NO_111 | TEKLEVPERA | PLAH- | SVVKK | RLSFPVVEKP | SVVPTEKPRE | 476 |
| SEQ_ID_NO_113 | TEKLEVPERA | PLVH- | SVVKK | RLSFPVVDKP | SVVPTDKPKE | 476 |
| SEQ_ID_NO_115 | TEKLELSERA | PLAH- | SVVNK | RLSFPVLDKP | SRPPADKPKE | 476 |
| SEQ_ID_NO_116 | TDRFEVPERV | PLVH- | SSIKK | RLSFPVADKP | NGEHADKLME | 478 |
| SEQ_ID_NO_117 | TDKFEVPERV | SLVH- | SSIKK | RLSFPAADKP | NIAPADKPME | 476 |
| SEQ_ID_NO_118 | LEKNGTPEKA | S--G- | SSAKK | RLSFPASP-- | ------A--- | 457 |
| SEQ_ID_NO_120 | IDNNGTPDKA | SV--- | GYVKK | RLSFSAS--- | ------PA-- | 455 |
| SEQ_ID_NO_122 | ---SGTPDRR | V--A- | GSAKK | RLLFPASP-- | ------A--- | 443 |
| SEQ_ID_NO_123 | ---HSPEKK- | GGGGS | VSARK | RLSFSPSS-- | ------AA-- | 431 |
| SEQ_ID_NO_124 | ---------- | S--E- | KTAKK | RLSFSGSP-- | ------K--- | 407 |

| | | | | | | |
|---|---|---|---|---|---|---|
| SEQ_ID_NO_111 | RVRRHSDPPK | VDPATL | KDA | ---------- | ---PAA | 498 |
| SEQ_ID_NO_113 | RVRRHSDPPK | VDPATL | KDV | ---------- | ---PAA | 498 |
| SEQ_ID_NO_115 | RVRRHSDPPK | VDPATL | KDA | ---------- | ---PVA | 498 |
| SEQ_ID_NO_116 | RGRRHSDPPK | VDPASL | KDV | ---------- | ---PVS | 500 |
| SEQ_ID_NO_117 | RARRHSEPPK | VDPASL | --- | ---------- | ------ | 492 |
| SEQ_ID_NO_118 | GPRRHSGPPR | VETSSI | KAI | SP-------- | ---AHRG | 482 |
| SEQ_ID_NO_120 | GARRHSGPPR | VDASAV | KDI | QMHREEKMSN | G-ASSK | 489 |
| SEQ_ID_NO_122 | SSRRHSEPPK | VDISEA- | RKN | QHA----PSN | GRQVAW | 474 |
| SEQ_ID_NO_123 | NSRRHSDPPK | VEM--- | --- | ---------- | ------ | 444 |
| SEQ_ID_NO_124 | TVRRFSGPPK | LESNVTK | KDT | ---------- | ---NLA | 430 |

Figure 5A

| SEQ_ID_NO | Sequence | Pos |
|---|---|---|
| SEQ_ID_NO_27 | MSITHSL---------------------LSS SSSAFLA-PS | 22 |
| SEQ_ID_NO_29 | MSLMNNL---------TTP--------MSS SSSTFLA-PT | 23 |
| SEQ_ID_NO_31 | MSPTQLL---------STS--------MSS SSSAFLAAPL | 23 |
| SEQ_ID_NO_33 | MSSTHQL---------STS---------SS SSSTFLA-PS | 23 |
| SEQ_ID_NO_34 | MYSLMSS---------VSS---------SS SSSSFLG-QT | 21 |
| SEQ_ID_NO_35 | MAASPAA---------PS--------AAA TVSSFVS-PS | 21 |
| SEQ_ID_NO_37 | MAAAPASSAA------GA--------AIT ASSSFVS-SS | 28 |
| SEQ_ID_NO_39 | MAAAPAG---AMAAAP--------AIT ASSSFLA-SP | 21 |
| SEQ_ID_NO_41 | MAAAPAG---------AP---------AIT ASSSFVS-SS | 21 |
| SEQ_ID_NO_42 | MSIPSAR---------LCITVPA TRNLSSSVSF STATSLL-PK | 32 |
| | | |
| SEQ_ID_NO_27 | SFNC-R---QVSLP- V-SICKCVAT PE-AETAYKT | 54 |
| SEQ_ID_NO_29 | SFNSSR---G-SVSVP- I--NIVKCVAT PQEQQNAYKT | 58 |
| SEQ_ID_NO_31 | AFKA-R---TQNVSIA-SKT- P-SICTCAAA PQEQKTVYKT | 57 |
| SEQ_ID_NO_33 | NFNL-R---NQNACLPMAKR- V-NTCKCVAT PQE-KLEYKT | 57 |
| SEQ_ID_NO_34 | HFDS-R---TRNACLP-TKD- S-WCKCVAT PSTETIAHTT | 55 |
| SEQ_ID_NO_35 | SFSSVKASKP-NPDRLRP-ARRA AAVNVRCVSS PPATETSFKT | 60 |
| SEQ_ID_NO_37 | PCSL-RVSKT-SPRRP-TGRV S-HKIS CVSS PAAAETSYKT | 65 |
| SEQ_ID_NO_39 | PFAL-KASTT-SHRRP-AGRV S-VNIRCVSS PPAVDTSYKT | 58 |
| SEQ_ID_NO_41 | PFCL-KASMT-SQRRP-AGRV S-IVIRCVSS PPAVDTSFKT | 58 |
| SEQ_ID_NO_42 | ---VSVTRGAS- V-SLIRCIAE PA-EKTTYTT | 58 |
| | | |
| SEQ_ID_NO_27 | GVNRNPNMGK LQAGYLFPEI ARRRSAHLLK YPDAKVISLG | 94 |
| SEQ_ID_NO_29 | KVSRNANIAK LQAGYLFPEV ARRAAHLLK YPNAQVISLG | 98 |
| SEQ_ID_NO_31 | QVSRNANIAK LQAGYLFPEV ARRRNAHMLK YPDAKVISLG | 97 |
| SEQ_ID_NO_33 | KVSRNSNMSK LQAGYLFPEI ARRRSAHLLK YPDAQVISLG | 97 |
| SEQ_ID_NO_34 | KVSRNANMAK LQAGYLFPEI ARRAAHMLK YPDAQVISLG | 95 |
| SEQ_ID_NO_35 | KVPRNANMAK LQAGYLFPEI ARRAAHLLK FPDAKIISLG | 100 |
| SEQ_ID_NO_37 | SVPRNANMAK LQAGYLFPEI ARRAAHLLK FPDAKIISLG | 105 |
| SEQ_ID_NO_39 | NVPRNANMAK LQAGYLFPEI ARRAAHLLK YPDAKIISLG | 98 |
| SEQ_ID_NO_41 | NVPRNANMAK LQAGYLFPEI ARRAAHLLK YPDAKIISLG | 98 |
| SEQ_ID_NO_42 | SVNRNANIAK LQAGYLFPEI ARRRNAHIQR YPDAKVISLG | 98 |

Figure 5B

| SEQ_ID_NO_27 | GDTTEPI PE | VI TDAMSKRS | HALSTI EGYS | GYGAEQGEKP | 134 |
|---|---|---|---|---|---|
| SEQ_ID_NO_29 | GDTTEPI PD | VI TSAMAKRS | HALSTLEGYS | GYGAEQGEKA | 138 |
| SEQ_ID_NO_31 | GDTTEPI PE | VI TSAI AKRA | EALSTLEGYS | GYGPEQGEKP | 137 |
| SEQ_ID_NO_33 | GDTTEPI PE | VI TSAMAKKA | HELSTI EGYS | GYGAEQGEKP | 137 |
| SEQ_ID_NO_34 | GDTTEPI PE | VI TSGMAKKA | HALSTVDGYS | GYGAEQGAKP | 135 |
| SEQ_ID_NO_35 | GDTTEPI PD | VI TNAMAKRA | HALSTI DGYS | GYGAEQGEKQ | 140 |
| SEQ_ID_NO_37 | GDTTEPI PD | VI TNAMAERA | LALSTI DGYS | GYGAEQGEKK | 145 |
| SEQ_ID_NO_39 | GDTTEPI PN | VI TNAMAERA | HALSTI DGYS | GYGAEQGEKK | 138 |
| SEQ_ID_NO_41 | GDTTEPI PN | VI TNAMAERA | HALSTI DGYS | GYGAEQGEKK | 138 |
| SEQ_ID_NO_42 | GDTTEPI PT | VI TGAMEARA | RALSTLEGYS | GYGAEQGEKP | 138 |

| SEQ_ID_NO_27 | LRRALASTFY | SDLGI EEDDI | FVSDGAKCDI | SRLQI VFGSN | 174 |
|---|---|---|---|---|---|
| SEQ_ID_NO_29 | LRAALASTFY | RNLGI EDDDI | FVSDGAKCDI | SRLQVVFGSN | 178 |
| SEQ_ID_NO_31 | LRI TAI ASTFY | SGLGI EEDDI | FVSDGAKCDI | SRLQMVFGAN | 177 |
| SEQ_ID_NO_33 | LRAAI AKTFY | GGLGI GDDDV | FVSDGAKCDI | SRLQVMFGSN | 177 |
| SEQ_ID_NO_34 | LRAAI ASTFY | GDLGI SDI | FVSDGAKSDI | SRLQVMFGSN | 175 |
| SEQ_ID_NO_35 | LRSAI AATYY | ADLGI EETDI | FVSDGAKCDI | SRLQVLFGSN | 180 |
| SEQ_ID_NO_37 | LRAAI AATYY | VDLGI EDSDI | FVSDGAKCDI | SRLQVLFGSN | 185 |
| SEQ_ID_NO_39 | LRAAI AATYY | ADLGI EDSDI | FVSDGAKCDI | SRLQVLFGSN | 178 |
| SEQ_ID_NO_41 | LRAAI AATYY | ADLGI EDSDI | FVSDGAKCDI | SRLQVLFGSN | 178 |
| SEQ_ID_NO_42 | LRAGLGAAFY | ADLGI DETEI | FVSDGAKCDI | TRLQLVFGPN | 178 |

| SEQ_ID_NO_27 | VKMAVQDPSY | PAYVDSSVI M | GQTGLFQKNV | EKFANI EYMR | 214 |
|---|---|---|---|---|---|
| SEQ_ID_NO_29 | VTMAVQDPSY | PAYVDSSVI M | GQTGQFQKDV | EKYGNI EYMR | 218 |
| SEQ_ID_NO_31 | VTMAVQDPSY | PAYVDSSVI M | GQTGQFQKDV | EKYGKI EYMR | 217 |
| SEQ_ID_NO_33 | VTI AVQDPSY | PAYVDSSVI M | GQTGQFNTDV | QKYGNI EYMK | 217 |
| SEQ_ID_NO_34 | VTMAVQDPSY | PAYVDLSVI L | GQTGQFQKDV | EKYGNI EYMK | 215 |
| SEQ_ID_NO_35 | VKI AVQDPSY | PAYVDSSVI M | GQTGLYQEDV | QKYGNI EYMR | 220 |
| SEQ_ID_NO_37 | VTI AVQDPSY | PAYVDSSVI M | SQTGLYQQDV | QKYGNI QYMR | 225 |
| SEQ_ID_NO_39 | VTI AVQDPSY | PAYVDSSVI M | GQTDLYQQDV | QKYGNI EYMR | 218 |
| SEQ_ID_NO_41 | VTI AVQDPSY | PAYVDSSVI M | GQTDLYQQDV | QKYGNI EYMR | 218 |
| SEQ_ID_NO_42 | VTMAAQDPSY | PAYVDTSVMM | GQTGLFQSDS | QQYSKI QYMK | 218 |

Figure 5C

| SEQ_ID | | | | | | |
|---|---|---|---|---|---|---|
| SEQ_ID_NO_27 | CNPENGFFPD | LSSISRPDI- | FFCSPNNPTG | AVATREQLTQ | 254 |
| SEQ_ID_NO_29 | CTPENGFFPD | LSKVARTDI- | FFCSPNNPTG | AAATREQLTR | 258 |
| SEQ_ID_NO_31 | CTPENGFFPD | LSKVSRTDI- | FFCSPNNPTG | SAATREQLTQ | 257 |
| SEQ_ID_NO_33 | CTPENGFFPD | LSTVGRTDI- | FFCSPNNPTG | AAATREQLTQ | 257 |
| SEQ_ID_NO_34 | CNPENGFFPD | LSTVSRTDI- | FFCSPYNPTG | NAATREQLTR | 255 |
| SEQ_ID_NO_35 | CTPENGFFPD | LSSVPRTDI- | FFCSPNNPTG | AAASRDQLTR | 260 |
| SEQ_ID_NO_37 | CNPENGFFPD | LSTVPRTDI- | FFCSPNNPTG | AAASRDQLTK | 265 |
| SEQ_ID_NO_39 | CSPENGFFPD | LSTIPRTDI- | FFCSPNNPTG | AAASRDQLTR | 258 |
| SEQ_ID_NO_41 | CGPENGFFPD | LSTVPRTDI- | FFCSPNNPTG | AAASRDQLTK | 258 |
| SEQ_ID_NO_42 | CTPENDFFPD | LSSTPRTDI- | FFCSPNNPTG | ASASRKQLEE | 258 |

| SEQ_ID | | | | | | |
|---|---|---|---|---|---|---|
| SEQ_ID_NO_27 | LVQFAKDNGS | VIHDSAYAM- | YISGDNPRSI | FEIPGAKEVA | 294 |
| SEQ_ID_NO_29 | LVKFAKDNGS | I-VYDSAYAM | YMSDDNPRSI | FEIPGAKEVA | 298 |
| SEQ_ID_NO_31 | LVQFAKDNGS | I-VYDSAYAM | YMSDDNPRSI | FEIPGAEEVA | 297 |
| SEQ_ID_NO_33 | LVEFAKKNGS | I-VYDSAYAM | YMSDDNPRSI | FEIPGAKEVA | 297 |
| SEQ_ID_NO_34 | LVQFAKDNGS | LVYDSGYAM- | YISDDSPRSI | FEIPGAKEVA | 295 |
| SEQ_ID_NO_35 | LVKFAKDNGS | I-VYDSAYAM | YISDDSPKSI | FEIPGAKEVA | 300 |
| SEQ_ID_NO_37 | LVKFAKDNGS | I-VYDSAYAM | YISDDSPKSI | FEIPGAREVA | 305 |
| SEQ_ID_NO_39 | LVKFAKDNGS | I-VYDSAYAM | YISDDSPKSI | FEIPGAKEVA | 298 |
| SEQ_ID_NO_41 | LVKFAKKNGS | I-VYDSAYAM | YISDDSPKSI | FEIPGAKEVA | 298 |
| SEQ_ID_NO_42 | LVAFAKKNGS | I-VYDSAYAI | YTSDDSPKSI | YEIPGAKECA | 298 |

| SEQ_ID | | | | | | |
|---|---|---|---|---|---|---|
| SEQ_ID_NO_27 | IETSSFSKYA | GFTGVRLGWT | VVPKQLLFSD | GFPVAKDFNR | 334 |
| SEQ_ID_NO_29 | IETASFSKYA | GFTGVRLGWT | VIPKQLLFSD | GFPVAKDFNR | 338 |
| SEQ_ID_NO_31 | LETSSFSKYA | GFTGVRLGWT | VVPKQLLYSD | GFPVKDFNR | 337 |
| SEQ_ID_NO_33 | METASFSKYA | GFTGVRLGWT | VIPKKLLYSD | GFPVAKDFNR | 337 |
| SEQ_ID_NO_34 | IEVSSFSKYA | GFTGVRLGWT | VVPKELLYSD | GFPVAKDFNR | 335 |
| SEQ_ID_NO_35 | IETASFSKYA | GFTGVRLGWT | VVPKELLFSD | GHPVAKDFNR | 340 |
| SEQ_ID_NO_37 | LETASFSKYA | GFTGVRLGWT | VVPKELLFSD | GHPVAKDFNR | 345 |
| SEQ_ID_NO_39 | IETASFSKYA | GFTGVRXGWT | VVPKELLFSD | GHPVAKDFNR | 338 |
| SEQ_ID_NO_41 | IETASFSKYA | GFTGVRLGWT | VVPKELLFSD | GHPVAKDFNR | 338 |
| SEQ_ID_NO_42 | IETASFSKYA | GFTGVRLGWT | VVPKALKFAD | GHPVHTDFNR | 338 |

Figure 5D

| SEQ_ID_NO_27 | IVCTCFNGAS | NISQAGGLAC | LSPEGLKAMR | DVIGFYKENT | 374 |
|---|---|---|---|---|---|
| SEQ_ID_NO_29 | IVCTCFNGAS | NIAQAGGLAC | LSSEGLKAMQ | EVIGFYKENT | 378 |
| SEQ_ID_NO_31 | VVCTSFNGAS | NICQAGGRAC | LSPEGLKAMS | EVIGFYKENS | 377 |
| SEQ_ID_NO_33 | LCTCFNGAS | NISQAGIALAC | LTPEGLEAMH | KVIGFYKENT | 377 |
| SEQ_ID_NO_34 | ECTTFNAAS | NISQASGLAC | LSPEGLEAMH | KLVGFYKENT | 375 |
| SEQ_ID_NO_35 | IVCTCFNGAS | NISQAGGLGC | LSPEGLKAMS | DVVGFYKENT | 380 |
| SEQ_ID_NO_37 | IVCTCFNGAS | NIAQAGGLAC | LSPEGLKAMH | DVVGFYKENT | 385 |
| SEQ_ID_NO_39 | IVCTCFNGAS | NISQAGGLAC | LSPEGLKAMQ | DVVGFYKENT | 378 |
| SEQ_ID_NO_41 | IVCTCFNGAS | NIAQAGGLAC | LSPDGLKAMQ | DVVGFYKENT | 378 |
| SEQ_ID_NO_42 | VMTTCFNGAS | NVAQAGGLAC | VSSEGLKAMH | ETVKFYKENT | 378 |

| SEQ_ID_NO_27 | NIMETFDSL | GFKVYGGKDA | PYVWHFPGR | SSWDVFAEIL | 414 |
|---|---|---|---|---|---|
| SEQ_ID_NO_29 | KIVETFNSL | GFKVYGGKNA | PYVWHFPGR | SSWDVFSEIL | 418 |
| SEQ_ID_NO_31 | NIMDTFNSL | GFNVYGGKNA | PYVWHFPGQ | SSWDVFAEIL | 417 |
| SEQ_ID_NO_33 | NILDTFTSL | GYDVYGGKNA | PYVWHFPNQ | SSWDVFAEIL | 417 |
| SEQ_ID_NO_34 | NIMETFTSL | GFSVYGGKNA | PYVWHFPGQ | SSWDVFAEIL | 415 |
| SEQ_ID_NO_35 | KIVDTFTSL | GFNVYGAKNA | PYVWHFPGR | NSWDVFAEIL | 420 |
| SEQ_ID_NO_37 | EIVDTFTSL | GFNVYGAKNA | PYVWHFPGR | NSWDVFAEIL | 425 |
| SEQ_ID_NO_39 | EIVDTFTSL | GFNVYGAKNA | PYVWHFPGR | NSWDVFAEIL | 418 |
| SEQ_ID_NO_41 | EIXVETXTSL | GFNVYGAKNA | PYVWHFPGR | NSWDVFAEIL | 418 |
| SEQ_ID_NO_42 | KILVETFESL | GFKTFGGKNA | PYVWQFPGK | SSWDVFSEIL | 418 |

| SEQ_ID_NO_27 | EKTHVVTTPG | SGFGPGGEGF | IRVSAFGHRE | NVLEACRRFK | 454 |
|---|---|---|---|---|---|
| SEQ_ID_NO_29 | EKTHIVTTPG | SGFGPGGEGF | IRVSAFGHRE | NVLEACRRFK | 458 |
| SEQ_ID_NO_31 | EKTHVVTTPG | SGFGPGGEGF | VRVSAFGHRE | NVLEACRRFK | 457 |
| SEQ_ID_NO_33 | EKTHVVTTPG | SGFGPGGEGF | RVCAFSHRG | NILEACRRFK | 457 |
| SEQ_ID_NO_34 | EKTHVVTTPG | SGFGPAGDGF | VRVSAFGHRE | NVLEACKRFK | 455 |
| SEQ_ID_NO_35 | EKAHVVTTPG | SGFGPGGEGF | VRVSAFGHRE | NIIEAARRLK | 460 |
| SEQ_ID_NO_37 | EKANVVTTPG | SGFGPGGEGF | VRVSAFGHRD | NIIEAARRLK | 465 |
| SEQ_ID_NO_39 | EKANVVTTPG | SGFGPGGEGF | VRVSAFGHRE | NIIEAARRLK | 458 |
| SEQ_ID_NO_41 | EKANVVTTPG | TGFGPGGEGF | VRVSAFGHRE | NIIEAARRXK | 458 |
| SEQ_ID_NO_42 | EQTHIVTTPG | SGFGPGGEGF | RASAFGHRE | NILEASRRLK | 458 |

Figure 5E

| SEQ_ID_NO_27 | QLY | --- | K | 458 |
|---|---|---|---|---|
| SEQ_ID_NO_29 | QLY | --- | N | 462 |
| SEQ_ID_NO_31 | QLY | --- | N | 461 |
| SEQ_ID_NO_33 | QLY | --- | K | 461 |
| SEQ_ID_NO_34 | RLY | --- | K | 459 |
| SEQ_ID_NO_35 | QLY | --- | K | 464 |
| SEQ_ID_NO_37 | QLY | --- | K | 469 |
| SEQ_ID_NO_39 | QLY | --- | K | 462 |
| SEQ_ID_NO_41 | QLY | --- | K | 462 |
| SEQ_ID_NO_42 | EYF | GS | KK | 465 |

Figure 6B

| SEQ ID | Col1 | Col2 | Col3 | Col4 | Score |
|---|---|---|---|---|---|
| SEQ_ID_NO_209 | RQFEVCTQDG | SVDRHGNPAI | RANTGKWLTA | ILILVNQGLA | 45 |
| SEQ_ID_NO_211 | KEQEVCTRDG | SVDRHGDPAI | RGRTGTWFAG | ILILVNQGLA | 59 |
| SEQ_ID_NO_212 | NPLSECTEDG | SVDRHGHPAV | RARTGNWVTA | ILILVNQGLA | 43 |
| SEQ_ID_NO_213 | KELEVCTLDG | SIDSHGHPAV | RERTGTWFAG | ILILVNQGLA | 43 |
| SEQ_ID_NO_214 | KRISDITEDG | SMDRRGNPAV | KAKTGNWRSS | ILLLVNYGLV | 48 |
| SEQ_ID_NO_216 | KWVSPTTEDG | SMDRRGNPAA | KAASGRWRSA | ILLLANYGLV | 48 |
| SEQ_ID_NO_218 | -AAELYTQDG | TIDLKGNPAL | KKDTGNWRAC | PYILANECCE | 43 |
| SEQ_ID_NO_219 | APDSEYPQDG | TVDLRGNPVL | KANTGGWKAC | PYILGNECCE | 46 |
| SEQ_ID_NO_220 | ASEDEYTGDG | SVDFWGRPSV | KENTGNWRAC | PFILGNECCE | 66 |
| SEQ_ID_NO_221 | DGIGLYTRDG | SVDIDGKPVL | KENTGKWRAC | PFILGTECCE | 57 |
| SEQ_ID_NO_222 | ENSGLYTGDG | SVDIKGNPVL | KSETGNWRAC | PFILGNECCE | 54 |
| SEQ_ID_NO_223 | EESKLYTGDG | SVDFKGRPVL | KKNTGNWKAC | PFILGNECCE | 58 |
| SEQ_ID_NO_225 | DKCCEYTLDG | SVDIKGRPAV | KGKSGGWLAG | ILILVNQGLA | 62 |
| SEQ_ID_NO_227 | TEKKVTGGNG | SYTEQSDTSY | KKIKGGWKTA | ILLLANQALA | 56 |
| SEQ_ID_NO_229 | KWSPATEDG | SMDRRGNPAV | KTTTGRWRSA | ILLLANYGLA | 48 |
| SEQ_ID_NO_230 | EKLCEYTLDG | SVDIKGRPAV | KGKSGGWLAG | ILILVNQGLA | 67 |
| SEQ_ID_NO_231 | RHTEVCTQDG | SVDRHGNPAI | RAKTGKWLTA | ILILVNQGLA | 45 |

Figure 6C

| SEQ_ID_NO | | | | | | |
|---|---|---|---|---|---|---|
| SEQ_ID_NO_209 | TLAFFGVGVN | LVL- | FLTRVM | GQDNAEAANN | VSKWTGTVYI | 84 |
| SEQ_ID_NO_211 | TLAFFGVGVN | LVL- | FLTRVL | GQDNAEAANN | VSKWTGTVYI | 98 |
| SEQ_ID_NO_212 | TLAFFGVGVN | LVL- | FLTRVL | GQDNATAANN | VSKWTGTVYI | 82 |
| SEQ_ID_NO_213 | TLAFFGVGVN | LVL- | FLTRVM | GQDNADAANN | VSKWTGTVYI | 82 |
| SEQ_ID_NO_214 | TCAFFGVGVN | LVV- | FLRRVL | HQDNAEAANS | ISKWTGTVYI | 87 |
| SEQ_ID_NO_216 | TCAFFGVGVN | LVV- | FLRRVL | HQDNAEAANN | ISKWTGTVYI | 87 |
| SEQ_ID_NO_218 | RLAYYGMSTN | LVN- | FMKDRM | GMANAAAANN | VTNWGGTCYI | 82 |
| SEQ_ID_NO_219 | RLAYYGI ATN | LVT- | YLSHEL | HQNPSTAANN | VTNWSGTCYI | 85 |
| SEQ_ID_NO_220 | RLAYYGI NTN | LVT- | YLTKRL | HQGNAAAAKS | VTTWAGTCYL | 105 |
| SEQ_ID_NO_221 | RLAYYGI ATN | LVT- | YLTSKL | HEGNASAARN | VTTWSGTCYL | 96 |
| SEQ_ID_NO_222 | RLAYYGI AAN | LVT- | YLTKKL | HEGNVSAARN | VTTWQGTCYI | 93 |
| SEQ_ID_NO_223 | RLAYYGI ATN | LVKP | ILAKL | HEGNVSAARN | VTTWQGTCYL | 98 |
| SEQ_ID_NO_225 | TLAFFGVNVN | LVL- | FLTRVL | GQSNEDAANN | VSKWTGVYM | 101 |
| SEQ_ID_NO_227 | TLAFFGVNVN | LVL- | FLTRVL | RQDSAEAANN | VSKWTGTVYI | 95 |
| SEQ_ID_NO_229 | TCAFFGVGVN | LVV- | FLRRVL | HQGNAEAANS | ISKWTGTVYI | 87 |
| SEQ_ID_NO_230 | TMAFFGVNVN | LVL- | FLTRLV | QQSNGDAANN | VSKWTGVYM | 106 |
| SEQ_ID_NO_231 | TLAFFGVGVN | LVL- | FLTRVM | GQDNAEAANN | VSKWTGTVYI | 84 |

Figure 6D

| SEQ ID | | | | | | |
|---|---|---|---|---|---|---|
| SEQ_ID_NO_209 | FSLLGAFLSD | SYWGRYKTCA | IFQASFVAGL | MMLSLSTGAL | 124 |
| SEQ_ID_NO_211 | FSLLGAFLSD | SYWGRYKTCA | IFQAIFVTGL | VLLSLSSYLF | 138 |
| SEQ_ID_NO_212 | FSLLGAFLSD | SYWGRYKTCA | IFQVIFVIGL | VLLSLSSYIF | 122 |
| SEQ_ID_NO_213 | FSLLGAFLSD | SYWGRYITCA | IFQVIFVVGL | VALSLTSYIF | 122 |
| SEQ_ID_NO_214 | FSLIGAFMSD | SYWGRYITCA | IFQMIYVTGL | VILSLASWFL | 127 |
| SEQ_ID_NO_216 | FSLIGAFLSD | SYWGRYVTCA | LFQIIYVTGL | VILSLASWFL | 127 |
| SEQ_ID_NO_218 | TPLIGAFLAD | AYLGRFWTIA | SFMIIYIFGL | GLLTMATSVH | 122 |
| SEQ_ID_NO_219 | TTLGAFLAD | AYLGRFWTIV | VFSIIYFLGM | VLLTLSAALP | 125 |
| SEQ_ID_NO_220 | TPLFGAVLAD | AYWGRYWTIA | AFSTIYFIGM | ATLTLSASVS | 145 |
| SEQ_ID_NO_221 | APLIGAVLAD | AYWGRYWTIA | VFSIIYFIGM | GTLTLSASVA | 136 |
| SEQ_ID_NO_222 | TPLIGAVLAD | SYWGRYWTIA | TFSTIYFIGM | CTLTLSASVP | 133 |
| SEQ_ID_NO_223 | APLIGAVLAD | SYWGRYWTIA | LFSMIYFIGM | GTLTLSASIP | 138 |
| SEQ_ID_NO_225 | FSLIGAFLSD | SYWGRYKTCA | IFQAIFVLGL | ALLSVSSHLY | 141 |
| SEQ_ID_NO_227 | FSLIGAFLSD | SYWGRYLTCA | IFQEFVVGL | GMLSLSSWRF | 135 |
| SEQ_ID_NO_229 | FSLIGAFLSD | SYWGRYVTCA | VFQIIYVMGL | VVLSLASWLL | 127 |
| SEQ_ID_NO_230 | FSLIGAFLSD | SYWGRYKTCA | IFQAIFVLGL | GLLSLSSRLY | 146 |
| SEQ_ID_NO_231 | FSLLGAFLSD | SYWGRYKTCA | IFQASFVAGL | VMLSLSTGAL | 124 |

Figure 6E

| SEQ_ID | Col1 | Col2 | Col3 | Col4 | Pos |
|---|---|---|---|---|---|
| SEQ_ID_NO_209 | LLEPSGCGVE | DSPCKPHSTF | KTVLFYLSVY | LIALGYGGYQ | 164 |
| SEQ_ID_NO_211 | LLKPRGCGDE | HSPCGSHSTY | QNVFFYFSIY | LVALGNGGYQ | 178 |
| SEQ_ID_NO_212 | LLKPNGCGDK | EFPCGSHSTF | EISFFYLSIY | LIALGNGGYQ | 162 |
| SEQ_ID_NO_213 | LLKPNGCGSK | ELPCGTHSSY | ETTLFYVSIY | LVALGNGGYQ | 162 |
| SEQ_ID_NO_214 | LVKPTGCGAA | GEHCDAPSSA | GVALFYLSTY | MIAFGNGGYQ | 167 |
| SEQ_ID_NO_216 | LVKPSGCGGV | DARCDEPSAP | GVALFYLSTY | MIAFGNGGYQ | 167 |
| SEQ_ID_NO_218 | GLVPACASK- | -GVCDPFTPG | QSAAVFIALY | LIALGTGGIK | 159 |
| SEQ_ID_NO_219 | SLKPPSGEG- | -VV--ALSST | QLAVFYLALY | LIALGTGGIK | 160 |
| SEQ_ID_NO_220 | SLKPPSCLG- | -SDCPTANLA | QYGVFFLGLY | LIALGTGGIK | 183 |
| SEQ_ID_NO_221 | AFKPSPCVG- | -SVCPAATPA | QYAVFFCGLY | LIALGTGGIK | 174 |
| SEQ_ID_NO_222 | AFKPPQCVG- | -SVCPSASPA | QYAIFFFGLY | LIALGTGGIK | 171 |
| SEQ_ID_NO_223 | ALKPAECLG- | -AVCPPATPA | QYAVFFIGLY | LIALGTGGIK | 176 |
| SEQ_ID_NO_225 | LIRPDGCGME | HAPCGPHSGK | ELGIFYIALY | MIAFGNGGYQ | 181 |
| SEQ_ID_NO_227 | LIKPVGCGNE | ETTCLEPSSV | GVGIFYLSIY | LVAFGYGGHQ | 175 |
| SEQ_ID_NO_229 | LVKPSGCGGV | KAHCDGPSAP | GVALFYLSTY | MIAFGNGGYQ | 167 |
| SEQ_ID_NO_230 | LIRPVGCGTE | HTPCASHSGT | EMGIFYIALY | MIAFGNGGYQ | 186 |
| SEQ_ID_NO_231 | LLEPSGCGVE | ESPCKPHSTV | KTVIFYLSVY | LIALGYGGYQ | 164 |

Figure 6F

| SEQ_ID | Col1 | Col2 | Col3 | Col4 | Length |
|---|---|---|---|---|---|
| SEQ_ID_NO_209 | PNIATFGADQ | FDAEDSVEGH | SKIAFFSYFY | LALNLGSLFS | 204 |
| SEQ_ID_NO_211 | PNIATFGADQ | FDEEDPKEGH | SKIAFFSYFY | LALNLGSLFS | 218 |
| SEQ_ID_NO_212 | PNIATFGADQ | FDEDNPKESH | SKVAFFSYFY | LALNLGSLFS | 202 |
| SEQ_ID_NO_213 | PTIATFGADQ | FDESDPSEQH | SKIAFFSYFY | LALNIGSLFS | 202 |
| SEQ_ID_NO_214 | PSIATFGSDQ | FDETDPREAR | SKVAFFSYFY | LALNVGSLFS | 207 |
| SEQ_ID_NO_216 | PSIATFGSDQ | FDETDPKEAR | SKVAFFSYFY | LALNVGSLFS | 207 |
| SEQ_ID_NO_218 | PCVSSFGADQ | FDEHDDVERK | SKSSFFNWFY | FSINIGALVA | 199 |
| SEQ_ID_NO_219 | PCVSSFGADQ | FDENDVKEKK | RKSSFFNWFY | FTINIGALIA | 200 |
| SEQ_ID_NO_220 | PCVSSFGADQ | FDDTDPKEKK | KKGSFFNWFY | FSINVGALVS | 223 |
| SEQ_ID_NO_221 | PCVSSFGADQ | FDDTDPVERV | QKGSFFNWFY | FSINIGALIS | 214 |
| SEQ_ID_NO_222 | PCVSSFGADQ | FDDTDPKERV | KKGSFFNWFY | FSINIGALIS | 211 |
| SEQ_ID_NO_223 | PCVSSFGADQ | FDDTDSRERV | SKVSFFSYFY | LALNLGSLFS | 216 |
| SEQ_ID_NO_225 | PNIATLGADQ | FDEDDPAEAH | AREAFFSYFY | LALNLGSLFS | 221 |
| SEQ_ID_NO_227 | PTLATFGADQ | FDEKNEKQKN | SKVAFFSYFY | FALNVGSLFS | 215 |
| SEQ_ID_NO_229 | PSIATFGSDQ | FDETDPEEAR | SKVSFFSYFY | LALNVGSLLS | 207 |
| SEQ_ID_NO_230 | PNIATFGADQ | FDEEDPAEAH | SKVSFFSYFY | MALNLGSLFS | 226 |
| SEQ_ID_NO_231 | PNIATFGSDQ | FDADDSVEGH | SKIAFFSYFY | LALNLGSLLS | 204 |

Figure 6G

| SEQ ID | Col1 | Col2 | Col3 | Col4 | Pos |
|---|---|---|---|---|---|
| SEQ_ID_NO_209 | NTVLGYFEDQ | GEWPLGFWAS | AGSAFAGLVL | FLIGTPKYRH | 244 |
| SEQ_ID_NO_211 | NTILGYFEDR | GMWALGFWAS | AGSALLALVL | FLIGTPRYRH | 258 |
| SEQ_ID_NO_212 | NTILGYFEDG | GRWVLGFWAS | SASALLALIL | FLFGLPRYRH | 242 |
| SEQ_ID_NO_213 | NTILDYFEDD | GLWTLGFCVS | AGSAALALVL | FLCGTSKYRY | 242 |
| SEQ_ID_NO_214 | NTVLVYYEDE | GRWWMGFWVS | AAAAAMALVL | FLLGTPNYRH | 247 |
| SEQ_ID_NO_216 | NTVLVYYEDS | GRWWMGFWVS | AAAAALALVL | FLLGTPNYRH | 247 |
| SEQ_ID_NO_218 | SSVLYYVQTH | VGWSWGFGIP | AVVMAIAVGS | FFVGTPLYRH | 239 |
| SEQ_ID_NO_219 | SSALVYIQEN | VGWGWGFGIP | AVAMGIAIVS | FLIGSPLYRH | 240 |
| SEQ_ID_NO_220 | SSVLVWQDN | VGWGWGFGIP | TLFMGLAIGS | FFSGTPLYRH | 263 |
| SEQ_ID_NO_221 | SSFLVMQDN | AGWGLGFGIP | TLFMGVAILS | FFSGTPLYRF | 254 |
| SEQ_ID_NO_222 | SSLIVMQEN | AGWGLGFGIP | AVFMGIAIAS | FFFGTPLYRF | 251 |
| SEQ_ID_NO_223 | SSFIVMQEN | AGWGLGFGIP | ALFMGLAIGS | FFLGTPLYRF | 256 |
| SEQ_ID_NO_225 | NTFLSYLEDK | GSWALGFWAS | TAAAATALLL | FLSGTLRYRY | 261 |
| SEQ_ID_NO_227 | NTILVYYEDS | GMWTMGFLVS | LASAVALVS | YLAGVRKYRY | 255 |
| SEQ_ID_NO_229 | NTVLVYYEDS | GRWWMGFWVS | AAAAALALVL | FLLGTPGYRH | 247 |
| SEQ_ID_NO_230 | NTFLSYLQDH | GKWVLGFWAS | TAAAATALLL | FLSGTPQYRH | 266 |
| SEQ_ID_NO_231 | NTVLGYFEDQ | GAWPLGFWAS | AGSAFAGLVL | FLAGTPKYRH | 244 |

Figure 6H

| SEQ ID | Sequence | End |
|---|---|---|
| SEQ_ID_NO_209 | FTPRESPWSR FCQVLVAATR KAKID-V--HH EELNLYDS- | 280 |
| SEQ_ID_NO_211 | FTPKGNPLSR CCQVMAATR KWKVQRM-PN QGDDQFESD- | 296 |
| SEQ_ID_NO_212 | FKPSGNPLSR FCRVVVAATR KWKVE-M--PP EGEDLYEVD- | 279 |
| SEQ_ID_NO_213 | FKPVGNPLPR FCQVFVAALR KWKVQ-M--FD GEDKLHEVE- | 279 |
| SEQ_ID_NO_214 | FKPTGNPLTR LAQVFVAAFR KWRAE-V--PR SE-LLHEVD- | 283 |
| SEQ_ID_NO_216 | FKPSGNPLTR VAQVFVAALR KWHAE-V--PR EE-FLHEVE- | 283 |
| SEQ_ID_NO_218 | QRPGGSPLTR LAQVLVAATR KLGV-----PV DGSALYETA- | 274 |
| SEQ_ID_NO_219 | QKPGGSPITR LAQVLVAATR KLSMK-V--QP NGKHLYEAD- | 277 |
| SEQ_ID_NO_220 | QKPGGSPVTR MCQVVVASLR KLRKT-V--PL DHSHLYEVQ- | 300 |
| SEQ_ID_NO_221 | QKPGGSPLMR MCQVFVASFR KWNLD-V--PQ DSSLLFELP- | 291 |
| SEQ_ID_NO_222 | QKPGGSPLTR MCQVLVAVFH KWNLS-V--PD DSTLLYETP- | 288 |
| SEQ_ID_NO_223 | QKPGGSPLTR MCQVVAASFR KRNLT-V--PE DSSLLYETP- | 293 |
| SEQ_ID_NO_225 | FQPGGNPIGR LCQVAIAASR KWKAG-ASTT GVVSLYEGD- | 299 |
| SEQ_ID_NO_227 | VKGYGNPVLR VVQVFVATVR KWKVG-----PA KEHQLYEVD- | 291 |
| SEQ_ID_NO_229 | FKPSGNPLTR VAQVFVAALR KWRAE-V--PR GE-LLHEVVE | 284 |
| SEQ_ID_NO_230 | AQPCGNPMAS LCQVASAACR NWKSG-GVSP DVEILYEGD- | 304 |
| SEQ_ID_NO_231 | FKPRESPWSR FCQVLVASTR KAKID-V--NY DDMNLYDS- | 280 |

Figure 6I

| SEQ_ID | Sequence | End |
|---|---|---|
| SEQ_ID_NO_209 | ----ETQYTG DKKI LHTKGF RFLDRAAI VT PDDEAEKVES | 316 |
| SEQ_ID_NO_211 | VPKDGSKNG DRKI LHTQGF RFLDRAAI I T SKDYT----E | 331 |
| SEQ_ID_NO_212 | G-DDDCSGNC RRKML HTQGF KFLDKAAVLT AKERE----Q | 313 |
| SEQ_ID_NO_213 | D---CLSNG GRKMYHTQGF RFLDKAAFI T PKDLK----Q | 311 |
| SEQ_ID_NO_214 | G-DESQI AG I RKI LHSDQL RFLDKAATVT EEDYCT----P | 318 |
| SEQ_ID_NO_216 | G-EDPKVSG I RKI LHSDEL RFLDRAATVT EEEYGA----P | 318 |
| SEQ_ID_NO_218 | D-RESGI EG SRKLEHTEQF RFLDKAAVET QADKT----A | 308 |
| SEQ_ID_NO_219 | D-KESGI EG SRKLEHTEEF RFLDKAAI PR GDEEL----Q | 311 |
| SEQ_ID_NO_220 | D-RNSAI QG SRKLEHTDEF KCLDKSAI I T DDDVR----K | 334 |
| SEQ_ID_NO_221 | D-KTSAI EG SRKLEHSDEL RCLDKAAVVS DLDVQ----Q | 325 |
| SEQ_ID_NO_222 | D-KSSAI EG SRKLL HTDEL RCLDKAAVVS DNELT----T | 322 |
| SEQ_ID_NO_223 | D-KSSAI EG SRKLQHSDEL RCLDRAAVI S DDERK----R | 327 |
| SEQ_ID_NO_225 | E-K-ADAAG GRKLL HTQGF SFLDRAAHAD TDSK----L | 331 |
| SEQ_ID_NO_227 | G-PESAI KG SRKI HHSNDF RFMDKAATI T EKDAV---- | 324 |
| SEQ_ID_NO_229 | AG-EDPKVSG I RKI LHSDGL RFLDKAATI T EEEE---- | 317 |
| SEQ_ID_NO_230 | D-K--TDSG SRKLL HTKGF RFLDRAALTT EDTNSK---L | 337 |
| SEQ_ID_NO_231 | ----ETQRTG DKKI LHTKGF RFLDRAAI VT PDDEAEKVES | 316 |

Figure 6J

| SEQ_ID | Sequence | | | | # |
|---|---|---|---|---|---|
| SEQ_ID_NO_209 | - - - GSKYDPW | RLCSVTQVEE | VKCVLRLLPI | WLCTI LYSVV | 353 |
| SEQ_ID_NO_211 | - - - NRLHDPW | RVCTVNQVEE | FKCI LRLLPI | WLCTI LYSVV | 368 |
| SEQ_ID_NO_212 | - EDKESRSPW | RI CTVTQVEE | VKCI LRLLPI | WLCTI LYSVV | 352 |
| SEQ_ID_NO_213 | - MEENKCSPW | FLSTVTQVEE | VKCI LRLLPI | WLCTI LFSVV | 350 |
| SEQ_ID_NO_214 | - - - ENMQDPW | RLCTVTQVEE | VKCI LKMLPI | WLCTI VYSVV | 355 |
| SEQ_ID_NO_216 | - - - EKMKDPW | RLCTVTQVEE | VKCI LKMLPI | WLCTI VYSVV | 355 |
| SEQ_ID_NO_218 | - - - - TGPSPW | RLCTVTQVEE | LKSVVRLLPI | WASGI VFATV | 344 |
| SEQ_ID_NO_219 | - - - GTRPSGW | RLTSVTQVEE | VKI VMRLLPI | WASGI VFATV | 348 |
| SEQ_ID_NO_220 | - - - GGFSNPW | RLCTVTQVEE | MKI LLRMFPI | WATGI VFAAV | 371 |
| SEQ_ID_NO_221 | - - - GDLTNPW | RLCTVTQVEE | LKI LI RMFPI | WATGI VFSAV | 362 |
| SEQ_ID_NO_222 | - - - GDYSNAW | RLCTVTQVEE | LKI LI RMFPI | WATGI VFSAV | 359 |
| SEQ_ID_NO_223 | - - - GDYSNLW | RLCTVTQVEE | LKI LI RMFPV | WATGI VFSAV | 364 |
| SEQ_ID_NO_225 | - - - GARDPW | KLCTVTQVEE | VKSI LRLLPI | WLCTI LYSVV | 367 |
| SEQ_ID_NO_227 | - - - NLKNHW | RLCTVTQVEE | AKCVLRMLPV | WLCTI LYSVV | 360 |
| SEQ_ID_NO_229 | - - - - EEGPW | RLCTVTQVEE | VKCI LRMLPI | WLCTI VYSVV | 352 |
| SEQ_ID_NO_230 | ATCSKTRDQW | RLCTVTQVEQ | VKSI LRI LPI | WVCTI LYSVV | 377 |
| SEQ_ID_NO_231 | - - - GSAYDPW | RLCSVTQVEE | VKCVLRLLPI | WLCTI LYSVV | 353 |

Figure 6K

| SEQ_ID | | | | | | | End |
|---|---|---|---|---|---|---|---|
| SEQ_ID_NO_209 | FTQMASLFVV | QGAAMK--- | TN | IK- | NFRIPA | SSMSSFDILS | 389 |
| SEQ_ID_NO_211 | FTQMASLFVE | QGADMK--- | TT | IS- | KFHIPP | ASMSSFDILS | 404 |
| SEQ_ID_NO_212 | FTQMASLFVE | QGAAMK--- | TT | LL- | GFHIPP | ASMSSFDIVS | 388 |
| SEQ_ID_NO_213 | FSQMASLFVE | QGAAME--- | TK | IS- | TFHIPP | ASMSVFDILS | 386 |
| SEQ_ID_NO_214 | FTQMASLFVE | QGTTMN--- | TN | IG- | SFHVPA | ASMSVFDILS | 391 |
| SEQ_ID_NO_216 | FTQMASLFVE | QGATMN--- | TN | IG- | SFHFPA | ASMSLFDILS | 391 |
| SEQ_ID_NO_218 | YGQMSTMFVL | QGNTLD--- | AS | MGPK- | FKIPS | ASLSIFDTLS | 381 |
| SEQ_ID_NO_219 | YSQMSTMFVQ | QGALMN--- | VS | MG-K- | ANIPS | ASLSIFDTIS | 384 |
| SEQ_ID_NO_220 | YSQISTMFVE | QGMTLD--- | TS | IG- | SRFHIPP | ASLSVFDVVS | 408 |
| SEQ_ID_NO_221 | YAQMSTMFVE | QGMVLD--- | TT | IG- | SFTIPP | ASLSTFDVLS | 398 |
| SEQ_ID_NO_222 | YAQMSTMFVE | QGMVMD--- | TA | VG- | SFKIPA | ASLSTFDTIS | 395 |
| SEQ_ID_NO_223 | YAQMSTMFVE | QGTMMD--- | TS | VG- | SFKIPA | ASLSTFDVIS | 400 |
| SEQ_ID_NO_225 | FTQMASLFVV | QGAAMRRTTP | FS- | GFSVPP | SSMSAFDILA | 405 |
| SEQ_ID_NO_227 | FTQMASLFVE | QGDVMN- | NK | IG- | NFHLPA | ASMSVFDICS | 396 |
| SEQ_ID_NO_229 | FTQMASLFVE | QGATMD--- | TN | IG- | SFHFPA | ASMSLFDVLS | 388 |
| SEQ_ID_NO_230 | FTQMASLFVV | QGAAMRRTTP | LG- | SFSIPA | SSMSAFDILT | 415 |
| SEQ_ID_NO_231 | FTQMASLFVV | QGAAMK--- | TN | IK- | DFRIPA | SSMSTFDILS | 389 |

Figure 6L

| SEQ_ID_NO | | | | | |
|---|---|---|---|---|---|
| SEQ_ID_NO_209 | VAFFI FAYRR | FLDPLFARLN | KTERNKGLTE | LQRMGI GLVI | 429 |
| SEQ_ID_NO_211 | VAAFI FI YRR | VLDPLVARI R | KL - DPKGLTE | LQRMGI GLVI | 442 |
| SEQ_ID_NO_212 | VAAFI FI YRR | VLDPLVARLK | GT - KARGLTE | LQRMGI GLI I | 427 |
| SEQ_ID_NO_213 | VVSFI FI YRR | I LDPLVARFT | KF - KSKGI TE | LQRMGI GLVL | 424 |
| SEQ_ID_NO_214 | VLAFI AI YRR | VLVPVMSRLS | G- - NPQGLTE | LQRMGVGLVV | 429 |
| SEQ_ID_NO_216 | VLAFI AI YRR | VLVPVMARLS | G- - NPQGLTE | LQRMGVGLVI | 429 |
| SEQ_ID_NO_218 | VI AWWPVYDR | I LVPAVRSVT | G- - RPRGFTQ | LQRMGI GLVV | 419 |
| SEQ_ID_NO_219 | VI VCVVI YDR | FLVPVVRKRT | G- - HVRGFTQ | LQRMGI GLFI | 422 |
| SEQ_ID_NO_220 | VMMWPVYDR | VI VPI VSKYT | KL - RERGFTE | LQRMGI GLFI | 446 |
| SEQ_ID_NO_221 | VI VWWPVYDR | LLVPLARKFT | G- - KERGFSE | LQRMGI GLFI | 436 |
| SEQ_ID_NO_222 | VI FWWPVYDK | LLVPI ARRFT | G- - I ERGFSE | LQRMGI GLFL | 433 |
| SEQ_ID_NO_223 | VATTI FLYRR | FI VPI ARKFT | G- - KERGFSE | LQRMGI GLFI | 438 |
| SEQ_ID_NO_225 | VLLCTGI YRQ | AI CPFLARLT | G- - RPAGPTE | LQRMGLGLVV | 443 |
| SEQ_ID_NO_227 | VLAFI AI YRR | I LVPLAGRFS | G- - NPRGLTE | LQRMGVGLI I | 434 |
| SEQ_ID_NO_229 | VTTTI FLYRR | VLVPVMARLS | G- - NPQGLTE | LQRMGVGLVI | 426 |
| SEQ_ID_NO_230 | VAFFI FLYRR | AI CPLLARLT | G- - RPTGPTE | LQRMGLGLVL | 453 |
| SEQ_ID_NO_231 | VAFFI FAYRR | FLDPLFARLN | KTEPNKGLTE | LQRMGI GLVI | 429 |

Figure 6M

| SEQ_ID | Sequence | | | End |
|---|---|---|---|---|
| SEQ_ID_NO_209 | AI MAMI SAGI | VEI HRL KNKE | PE- - SAT- S- | - LS- SSST | 461 |
| SEQ_ID_NO_211 | AI I AMVSAGI | VELFRLKYAR | KD- - - - - - - | - - - SASS | 473 |
| SEQ_ID_NO_212 | AI I AMVAAGI | VEWFRLKYAK | KD- - - CP- R- | - CE- SESS | 458 |
| SEQ_ID_NO_213 | AI I AMVSAGL | VEI FRLKYAI | KEEKNCS- H- | - CE- GTSS | 458 |
| SEQ_ID_NO_214 | GMAAMVVAGV | VEVERLKRVG | A- - - - - - - - | - PD- QPSS | 456 |
| SEQ_ID_NO_216 | GMAAMVVAGA | VEVERLRRVA | A- - - - - - - - | - PD- QPSS | 456 |
| SEQ_ID_NO_218 | SMFAMLAAGV | LELVRLRTI A | QR- - GLY- G- | - EH- DVVP | 451 |
| SEQ_ID_NO_219 | SVLAMVAAI | VEI ERLKLAR | RD- - GVA- GN | PQDEAL PVES | 459 |
| SEQ_ID_NO_220 | SI LAMVAAAL | VEI RRLNI VK | TY- - DLVYD- | - KG- TPVP | 479 |
| SEQ_ID_NO_221 | SI LSMTAAAI | VEI RRLQI AK | SL- - GLV- D- | - QN- VAVP | 468 |
| SEQ_ID_NO_222 | SMLCMSAAAI | VEI RRLQLAR | DL- - GLV- D- | - EA- VSVP | 465 |
| SEQ_ID_NO_223 | SVLCMSAAAI | VEI KRLQLAK | EL- - DLV- D- | - KA- VPVP | 470 |
| SEQ_ID_NO_225 | GALAMATAGT | VEHFRKARAT | A- - - - - - - - | - A- MSSD | 469 |
| SEQ_ID_NO_227 | GMLAI LAAGA | TEFERLKHI T | P- - - - - - - - | - GE- KASS | 461 |
| SEQ_ID_NO_229 | GMAAMVVAGV | VEVERLKRVA | A- - - - - - - - | - PD- QPSS | 453 |
| SEQ_ID_NO_230 | GAMAMANAGT | VEHFRKASAT | T- - - - - - - - | - A- NGSE | 479 |
| SEQ_ID_NO_231 | AI TAMI SAGI | VEI YRLKHKE | T- - - - - - - - | - AS- NSSS | 456 |

Figure 6N

| SEQ ID | | | | | | End |
|---|---|---|---|---|---|---|
| SEQ_ID_NO_209 | LSIFWQVPQY | MLIGASEVFM | YVGQLEFFNS | QAPTGLKSFA | | 501 |
| SEQ_ID_NO_211 | LSILWQIPQY | VLIGASEVFM | YVGQLEFFNG | QAPDGLKSFG | | 513 |
| SEQ_ID_NO_212 | LSIFWQIPQY | VLIGASEVFM | YVGQLEFFND | QAPDGLKSFG | | 498 |
| SEQ_ID_NO_213 | LSIFWQVPQY | VLIGASEVFM | YVGQLEFFNS | QAPDGLKSFG | | 498 |
| SEQ_ID_NO_214 | LSVLWQVPQY | ALIGASEVFM | YVGQLEFFNG | QAPDGVKSFG | | 496 |
| SEQ_ID_NO_216 | LSVLWQVPQY | ALIGASEVFM | YVGQLEFFNG | QAPDGVKSFG | | 496 |
| SEQ_ID_NO_218 | ISIFWQVPQY | FIIGAAEVFT | FVGQLEFFYD | QAPDAMRS[MC] | | 491 |
| SEQ_ID_NO_219 | LTIFV̄QIPQY | FLIGAAEVFT | FVGQLEFFYD | QAPDAMRSL[M] | | 499 |
| SEQ_ID_NO_220 | MSIFWQIPQY | FLVGASEVFT | FIGQLEFFYD | QSPDAMRSLC | | 519 |
| SEQ_ID_NO_221 | MSILWQIPQY | FLVGASEIFT | FIGQLEFFYD | QSPDAMRSLC | | 508 |
| SEQ_ID_NO_222 | LSIFWQIPQY | FILGAAEVFT | FVGQLEFFYD | QSPDAMRSLC | | 505 |
| SEQ_ID_NO_223 | LTIFL̄QIPQY | FLLGAAEVFT | FVGQLEFFYD | QSPDAMRSLC | | 510 |
| SEQ_ID_NO_225 | LHIM̄WQVPQY | ALIGVSEVMM | YVGQLEFFNG | QMPDGLKSFG | | 509 |
| SEQ_ID_NO_227 | LSIFWQIPQY | VLVGASEVFM | YVGQLEFFNG | QAPDGIKSFG | | 501 |
| SEQ_ID_NO_229 | LSVLWQVPQY | ALIGASEVFM | YVGQLEFFNG | QAPDGVKSFG | | 493 |
| SEQ_ID_NO_230 | LHILWQVPQY | ALIGVSEVMM | YVGQLEFFNG | EMPDGF̄KSFG | | 519 |
| SEQ_ID_NO_231 | LSIFWQVPQY | MMIGASEVFM | YVGQLEFFNS | QAPTGLKSFA | | 496 |

Figure 60

| SEQ_ID | | | | | | |
|---|---|---|---|---|---|---|
| SEQ_ID_NO_209 | SALCMASI SL | GNYVSSLLVS | IVMKI STTD- | DVHGW PENL | 540 |
| SEQ_ID_NO_211 | SALCMTSI SL | GNYVSSLLVT | VVMKI STRD- | EMPGW PGNL | 552 |
| SEQ_ID_NO_212 | SALCMTSI SL | GNYVSSLLVT | IVMKFSTRD- | QMPGW PSNL | 537 |
| SEQ_ID_NO_213 | SALCMTSI SL | GNYVSSLLVA | IVMKI STRNE | GMLGW PGNL | 538 |
| SEQ_ID_NO_214 | SSLCMASI SL | GNYVSI MLVS | VVTSLTAGD- | RRPGW PGNL | 535 |
| SEQ_ID_NO_216 | SALCMASI SL | GNYVSI MLVS | VVTSLTAGE- | RRPGW PGNL | 535 |
| SEQ_ID_NO_218 | SALSLTTVAL | GNYLSTLLVT | VVAKLTTRG- | GKQGW PDNL | 530 |
| SEQ_ID_NO_219 | SALSLTTAL | GNYLSSVLVT | VTEVTTKG- | GKPGW PNNL | 538 |
| SEQ_ID_NO_220 | SALSLLTTAL | GNYLSSLI VT | VMFATTKG- | GNIGW PDNL | 558 |
| SEQ_ID_NO_221 | SALSLLTTAL | GNYLSSFI LT | MVTTI TTRG- | GKPGW PDNL | 547 |
| SEQ_ID_NO_222 | SALSLLTTSL | GNYLSSFI LT | VVTSI TTRG- | GKPGW PNNL | 544 |
| SEQ_ID_NO_223 | SALSLLTTSL | GNYFSDVI VS | VVLYFTTRG- | GNPGW PDNL | 549 |
| SEQ_ID_NO_225 | SALCMMSMSL | GNYVSSLLVY | AVTRLTTTR- | GRSGW PADL | 548 |
| SEQ_ID_NO_227 | SSLCMASI SL | GNYVSI MLVS | MVMGI TARG- | ENPGW PNNL | 540 |
| SEQ_ID_NO_229 | SALCMMSMSL | GNYFSDI I VS | VVTSLTAGE- | KRPGW PGNL | 532 |
| SEQ_ID_NO_230 | SALCMASI SL | GNYFSDI I VS | AVTKATAVD- | GRPGW PADL | 558 |
| SEQ_ID_NO_231 | SALCMASI SL | GNYVSSLLVS | IVMKI STRD- | DLPGW PGNL | 535 |

Figure 6P

| SEQ ID | Sequence | Length |
|---|---|---|
| SEQ_ID_NO_209 | NKGHLERFYF LLAGLTAADF VVYLICAKWY K- YIKSEASF | 579 |
| SEQ_ID_NO_211 | NKGHLDRFFF LLAVLTADL VLYIICARWY K- YIKFERQQ | 591 |
| SEQ_ID_NO_212 | NKGHLDRFYF LLAALTMADF GVYIICAKWY K- SIKLEGKY | 576 |
| SEQ_ID_NO_213 | NMGHLDRFYF LLAALTAADL LVYIAMARWY K- YVKFHGNN | 577 |
| SEQ_ID_NO_214 | NSGHLDRFYF LLAALSLVDL AVYVACAVWY K- GIKLDSNE | 574 |
| SEQ_ID_NO_216 | NSGHLDRFYF LLAALSLVDL AVYVACATWY K- GIKLDGGG | 574 |
| SEQ_ID_NO_218 | NVGHLDYFFW LLAALSLLNF AVYLLIASWY T- YKKTAG- | 567 |
| SEQ_ID_NO_219 | NRGHLDYFFW MLAILSILNL IEYLVVAKFY T- YKRVHNAA | 577 |
| SEQ_ID_NO_220 | NEGHLDYYFW VLASLSVLNL LVYVSCAHRY K- YKKA---- | 593 |
| SEQ_ID_NO_221 | NEGHLDYFFW LLAGLSFLNL VIYVFCAARY K- CKKA---- | 582 |
| SEQ_ID_NO_222 | NEGHLDYFFW LLAALSFFNL VIYVFLCQMY K- SKKA---- | 579 |
| SEQ_ID_NO_223 | NGGHLDYFFS- GLAGLSFLNM FLYIVAJAKRY G- SGKVDGRS | 583 |
| SEQ_ID_NO_225 | NKGHLDKFYF LLAVLAVADF AVYLVCASRY K- SINLGDGD | 587 |
| SEQ_ID_NO_227 | NEGHLDRFFF LVAVLTALDF VLYLLCARWY K- GIKLDGGD | 579 |
| SEQ_ID_NO_229 | NVGHMDRFFF LLAALSLVDL AVYVACAMWY K- GIKLDGGD | 571 |
| SEQ_ID_NO_230 | NSGHLDRFYF LLAILSVADF AVYLVFAGRY RK CKVEGRS | 598 |
| SEQ_ID_NO_231 | NEGHLNKFYF LLAALTAADF VVYLVCAKWY K- YIKSEASF | 574 |

Figure 6Q

| SEQ_ID_NO | Sequence | Position |
|---|---|---|
| SEQ_ID_NO_209 | S----E----------------------------------S-----EV | 589 |
| SEQ_ID_NO_211 | E----------A-------------------VTEEE---RV | 606 |
| SEQ_ID_NO_212 | E----DSI--LS----------NEEADL---MV | 589 |
| SEQ_ID_NO_213 | L----D----SN--S-------KGSDDV---VV | 589 |
| SEQ_ID_NO_214 | E----E----QG--N-------N--EEN---HV | 584 |
| SEQ_ID_NO_216 | E----K--------------T-NKITV---HV | 583 |
| SEQ_ID_NO_218 | DDH--P-DA-----------RKNPA---HD | 581 |
| SEQ_ID_NO_219 | DVG--E-DG-----------AKGGA---YE | 591 |
| SEQ_ID_NO_220 | ---------------------KPSKSG-----S | 594 |
| SEQ_ID_NO_221 | -----------------------------S | 583 |
| SEQ_ID_NO_222 | -----------------------------S | 580 |
| SEQ_ID_NO_223 | -----------------------------S | 584 |
| SEQ_ID_NO_225 | S----DDEEEG---A-AGQVTSLPA---YA | 606 |
| SEQ_ID_NO_227 | M-G--S---QE-----------DEEVIS---KV | 592 |
| SEQ_ID_NO_229 | G----D---NR---V-----RKVSA---HV | 582 |
| SEQ_ID_NO_230 | DDEE-E---GS---------DDEEAC---HA | 614 |
| SEQ_ID_NO_231 | S----E---S-----------I--AE---EE | 582 |

Figure 7A

| SEQ_ID | | | | | | |
|---|---|---|---|---|---|---|
| SEQ_ID_NO_370 | MGSSGADTPS | KEQ------ | QPPATSGA | ALPPVYPDWS | 31 |
| SEQ_ID_NO_374 | MGSSGADTPS | KTTKASAPQ- | EQQPPATSGA | ATPAVYPDWS | 39 |
| SEQ_ID_NO_376 | MGSSGADAPT | KTSKASAPQ- | EQQPPASSST | ATPAVYPDWA | 39 |
| SEQ_ID_NO_377 | MGSSGADTPT | KE------- | -QQPPATSSA | ATPVVYPDWT | 31 |
| SEQ_ID_NO_378 | MGSSEAETPA | KANKASAPQ- | EQQPPATSST | ATPTVYPDWT | 39 |
| SEQ_ID_NO_384 | MGSSDMDKTA | KEKESKTPP- | TTTQEQSSAT | TTGTVNPDWT | 40 |
| SEQ_ID_NO_385 | MGSSDMDKTG | KEKEAKTPSA | ASTQEQPSTA | GAATVNPDWS | 40 |
| SEQ_ID_NO_386 | MGSSEMDKTA | KEKESKTPP- | TTTQEQSSTT | SAGTVNPDWS | 39 |
| SEQ_ID_NO_391 | MGSSEMDKAG | KEKESKTPPP | PTSQEQSSTT | GTGTINPEWP | 40 |
| SEQ_ID_NO_392 | MGSSEMDKTP | KEKESKTPP- | PTSQEQSSTT | ATGTINPDWP | 39 |
| SEQ_ID_NO_370 | SFQAYPPIPP | HGFFPSPVAS | SPQGHPFMWG | AQAMIPPYGT | 71 |
| SEQ_ID_NO_374 | SFQAYPPIPP | HGFFPSPVAS | SPQGHPYMWG | AQPMIPPYGT | 79 |
| SEQ_ID_NO_376 | NFQGYPPIPP | HGFFPSPVAS | SPQGHPYMWG | AQPMIPPYGT | 79 |
| SEQ_ID_NO_377 | NFQGYPPIPP | HGFFPSPVVS | SPQGHPYMWG | AQPMMPPYGT | 71 |
| SEQ_ID_NO_378 | SFQGYPPIPP | HGFV----- | NPQGHPYMWG | PQPMMPPYGT | 79 |
| SEQ_ID_NO_384 | GFQAYSPIPP | PGFL----- | SPQAHPYMWG | VQPIMPPYGT | 76 |
| SEQ_ID_NO_385 | GFQAYSHIPP | HGFL----- | SPQAHPYMWG | VQHIMPPYGT | 76 |
| SEQ_ID_NO_386 | GFQAYSPIPP | HGFL----- | SPQAHPYMWG | VQHLMPPYGT | 75 |
| SEQ_ID_NO_391 | GFQAYSPIPP | HGFL----- | SPQAHPYMWG | VQQFMPPYGT | 76 |
| SEQ_ID_NO_392 | GFQAYSPIPP | HGFL----- | SPQAHPYMWG | VQQFMPPYGT | 75 |
| SEQ_ID_NO_370 | PPLPYVLMYP | PLGVYAHPSM | PPGAHPFTPY | AITSPNGNAD | 108 |
| SEQ_ID_NO_374 | PPPPYVLMYP | PLGVYAHPSM | PPGAHPFTPY | AITSPNGNAD | 117 |
| SEQ_ID_NO_376 | PPPPYVLMYP | PLGVYAHPSM | PPGAHPFTPY | AMASPNGNAD | 117 |
| SEQ_ID_NO_377 | PPL-YVLMYP | PPGGIYAHPSM | PPGAHPFAPY | AMASANGNAD | 108 |
| SEQ_ID_NO_378 | PPL-YVLLYP | PGGIYAHPSM | PPGAHPFAPY | TMTSPNGNPD | 116 |
| SEQ_ID_NO_384 | PPHPYVAMYP | HSGIYAHPSI | PPGSYPFSPF | AMPSPNGIAE | 116 |
| SEQ_ID_NO_385 | PPHPYVAMYP | H-GVYAHPSI | PPGSYPFSPF | AMPSPNGIAE | 115 |
| SEQ_ID_NO_386 | PPHPYVAMYP | PGGLYAHPSI | PPGSYPFSPF | AMPSPNGIAE | 115 |
| SEQ_ID_NO_391 | PPHPYVAMYP | PGGIYAHPSM | PPGSYPFNPF | AMPSPNGIAE | 116 |
| SEQ_ID_NO_392 | PPHPYVAMYP | PGGIYAHPSM | PPGSYPFSPF | AMPSPNGIAE | 115 |

Figure 7B

| SEQ_ID | | | | | | | | |
|---|---|---|---|---|---|---|---|---|
| SEQ_ID_NO_370 | ATGTTA---- | -------- | AAGNTDGKP | SEGKDKSPTK | RSKGSLGSLN | 143 |
| SEQ_ID_NO_374 | ATGTTA---- | -------- | AAGDTDGKP | SEGKDKSPTK | RSKGSLGSLN | 152 |
| SEQ_ID_NO_376 | PTGTTTTAAA | -A------ | AAAGETDGKS | SEGKEKSPIK | RSKGSLGSLN | 157 |
| SEQ_ID_NO_377 | ATGTTATAA- | -A------ | PSAGETDGKS | SEGKEKSPIK | SSKGSLGSLN | 147 |
| SEQ_ID_NO_378 | AAGTTTTA-- | -------- | TAGGETNGKS | SEGKEKSPIK | RSKGSLGSLN | 155 |
| SEQ_ID_NO_384 | ASGYTP---- | -------- | GNTEPDGKP | SDVKEKLPIK | RSKGSLGSLN | 151 |
| SEQ_ID_NO_385 | VSGNTP---- | -------- | GSMEAEGRP | SDAKEKLPIK | RSKGSLGSLN | 150 |
| SEQ_ID_NO_386 | TSGTTP---- | -------- | GSMEADGKS | SEGKEKLPIK | RSKGSLGSLN | 150 |
| SEQ_ID_NO_391 | ASGNTP---- | -------- | GSMEADGKP | SEVKEKLPIK | RSKGSLGSLN | 151 |
| SEQ_ID_NO_392 | ASGNTP---- | -------- | GSMEADGKP | PEVKEKLPIK | RSKGSLGSLN | 150 |

| SEQ_ID | | | | | |
|---|---|---|---|---|---|
| SEQ_ID_NO_370 | MLTGKNPSEH | GKSSGASGNG | VTSQSGESGS | D--SSSEGSE | 181 |
| SEQ_ID_NO_374 | MLTGKNTGEH | GKTSGASANG | ATSQSGESGS | D--SSSEGSE | 190 |
| SEQ_ID_NO_376 | MITGKNSTEH | GKTSGASANG | AISQSGESGS | E--SSSEGSE | 195 |
| SEQ_ID_NO_377 | MITGKNCVEH | GKTSGASANG | AISQSGESGS | E--SSSEGSE | 185 |
| SEQ_ID_NO_378 | MITGKNCVEH | GKTSGASANG | AITSQSGESGS | E--SSSEGSE | 193 |
| SEQ_ID_NO_384 | MITGKN-NEL | GKTSGASANG | AYSKSAESGS | E--GTSEGSD | 188 |
| SEQ_ID_NO_385 | MITGKN-NEH | GRTSGASANG | AYSKSAESGS | E--GTSEGSD | 187 |
| SEQ_ID_NO_386 | MITGKN-NEL | GKTSGASANG | VYSKSAESAS | E--GSSEGSD | 187 |
| SEQ_ID_NO_391 | MITGKN-NEH | GKTLGTSANG | HSKSGESAS | EGEGTSEGSD | 190 |
| SEQ_ID_NO_392 | MITGKN-NEH | GKTRGTSANG | IHSKSGDSAS | EGEGTSEGSD | 189 |

| SEQ_ID | | | | | |
|---|---|---|---|---|---|
| SEQ_ID_NO_370 | GNSHNDSHHK | ESGQEHDGDV | RSSRNGVSRL | QSE------A | 214 |
| SEQ_ID_NO_374 | ENSHNDSHHK | ESGQEQDGDV | RSSQNGASRS | PSE------A | 223 |
| SEQ_ID_NO_376 | ANSQNDSHHK | ESGQEQDGEV | RSSQNGVSRS | PSQ------P | 228 |
| SEQ_ID_NO_377 | PNSQNDSHHK | ESGQEQDGEI | RSSQNGVSRS | PSQ------P | 218 |
| SEQ_ID_NO_378 | ANSQNDSQHK | ESGQEQDGDV | RSSQNGVSPS | PSQ------P | 226 |
| SEQ_ID_NO_384 | ANSQNDSQMK | SGGRQDS-E- | DASQNGGSAH | GLQNGGQ--A | 224 |
| SEQ_ID_NO_385 | ADSQSDSQMK | SGGRQDS-LE | ETSQNGGSAH | AAQNGGQ--A | 225 |
| SEQ_ID_NO_386 | ANSQSDSQLK | SGCRQDSLEA | ETSQNGSTCH | APQNGGPNTP | 227 |
| SEQ_ID_NO_391 | ANSQNDSQLK | SGGRQDSFED | EPSQNGSSAY | TPQNGGLNDP | 230 |
| SEQ_ID_NO_392 | ANSQNDSQMK | SGGRQDSFED | EPSQNGTSAY | TSQNGGISTP | 229 |

Figure 7C

| | | | | | |
|---|---|---|---|---|---|
| SEQ_ID_NO_370 | -GKLNQAMAI | LPIPSS--G | PATDPTTNLN | IGMDYWAN-T | 249 |
| SEQ_ID_NO_374 | -GKLNQAMTI | VPMPSS--G | PVTGPTTNLN | IGMDYWAN-T | 258 |
| SEQ_ID_NO_376 | -AKLNQTMAI | MPMTSS--G | PVPAPTTNLN | IGMDYWAN-T | 263 |
| SEQ_ID_NO_377 | -AKLKQTMAI | MPMPSS--G | SMPGPTTNLN | IGMDYWAN-T | 253 |
| SEQ_ID_NO_378 | -AQLKQTLAI | MQMPSS--G | PVPGPTTNLN | IGMDYWAN-T | 261 |
| SEQ_ID_NO_384 | NTVMNQTMSI | VPISATGAPG | ALPGPATNLN | IGMDYWGA-T | 263 |
| SEQ_ID_NO_385 | STIMNQTMGV | LPISAASAPG | VIPGPTTNLN | IGMDYWGAPV | 265 |
| SEQ_ID_NO_386 | HAMVNQTMAI | MPISAPGAPG | GVPGPTTNLN | IGMDYWGAPT | 267 |
| SEQ_ID_NO_391 | HTVVNQTMSI | LPISAGGAPG | AVPGPTTNLN | IGMDYWGTPG | 270 |
| SEQ_ID_NO_392 | ATVVNQNVPL | LPISAGGAPG | AVPGPTTNLN | IGMDYWGTPA | 269 |

| | | | | | |
|---|---|---|---|---|---|
| SEQ_ID_NO_370 | ASSAPAIHGK | ATSTTVPGAV | ------ | AEQWTQDEHE | 281 |
| SEQ_ID_NO_374 | ASSAPAIHGK | VTPTTVPGAV | ------VP | AEQWMQDERE | 290 |
| SEQ_ID_NO_376 | ASSTPALHGK | ATPTAAPGSM | ------VP | GEQWWQDERE | 295 |
| SEQ_ID_NO_377 | ASSPPAAHGK | ATPTAVPGTA | ------VP | TEPWMQDERE | 285 |
| SEQ_ID_NO_378 | ASSSPALHGK | VTPTAIPGAV | ------AP | TEPWMQDERE | 293 |
| SEQ_ID_NO_384 | SSAIPAIRGK | VPSTPVAGGV | VTPGSRDAVQ | SQLWLQDERE | 303 |
| SEQ_ID_NO_385 | ASSVPAIRGK | VPSTPVAGGI | ATAGSRDGVQ | SQHWLQDERE | 305 |
| SEQ_ID_NO_386 | SSTIPAMRGK | VPSAPVTGGI | VTAGSRDSVQ | SQLWLQDERE | 307 |
| SEQ_ID_NO_391 | SSNIPGLGRK | VPSTAVAGGM | VTVGSRDSAQ | SQLWLQDERE | 310 |
| SEQ_ID_NO_392 | PSNIPALGRK | VPSTAVAGS- | ----RDSVQ | SQLWLQDERE | 303 |

| | | | | | |
|---|---|---|---|---|---|
| SEQ_ID_NO_370 | LKKQRRKQSN | RESARRSRLR | KQAECEELAQ | RADVLKQENA | 321 |
| SEQ_ID_NO_374 | LKRQRRKQSN | RESARRSRLR | KQAECEELAQ | RADVLKQENA | 330 |
| SEQ_ID_NO_376 | LKRQRRKQSN | RESARRSRLR | KQAECEELAQ | RAEVLKQENT | 335 |
| SEQ_ID_NO_377 | LKRQKRKQSN | RDSARRSRLR | KQAECEELAQ | RAEVLKQENA | 325 |
| SEQ_ID_NO_378 | LKRQRRKQSN | RDSARRSRLR | KQAECEELAQ | RAEVLKQENA | 333 |
| SEQ_ID_NO_384 | SSTIPAMRGK | RESARRSRLR | KQAECDELAQ | RAEALKEENA | 343 |
| SEQ_ID_NO_385 | LKRQRRKQSN | RESARRSRLR | KQAECDELAQ | RAEVLKEENA | 345 |
| SEQ_ID_NO_386 | LKRQRRKQSN | RESARRSRLR | KQAECDELAQ | RADALKEENA | 347 |
| SEQ_ID_NO_391 | LKRQRRKQSN | RESARRSRLR | KQAECDELAQ | RAEALKEENA | 350 |
| SEQ_ID_NO_392 | IKRQRRKQSN | RESARRSRLR | KQAECDELAQ | RAEALKEENA | 343 |

Figure 7D

| SEQ_ID_NO | | | | | |
|---|---|---|---|---|---|
| SEQ_ID_NO_370 | SLRDEVNRI R | KEYEELLSRN | NSLKEKLEGK | QHKTDEA- | GL | 360
| SEQ_ID_NO_374 | SLRDEVNRI R | KEYEELLSKN | NSLKEKLEGK | QHKTDEA- | GL | 369
| SEQ_ID_NO_376 | SLRDEVNRI R | KEYEELDELLSKN | SSLKEKLEDK | QHKTDEA- | GV | 374
| SEQ_ID_NO_377 | TLRDEVNRVR | KEYDELI SKN | NSLKDKLGDK | EHKTDDA- | EL | 364
| SEQ_ID_NO_378 | SLKDEVSRI R | KEYEQLLSKN | SSLKDNVGDK | QHKTDEA- | GL | 372
| SEQ_ID_NO_384 | NLRSEVNRI K | SEYEQLLAEN | ASLKERL GEI | PGNDDL- - | RA | 381
| SEQ_ID_NO_385 | NLRSEVNRI K | SEYEQLLAEN | ASLKERL GEV | HGQEDS- - | RA | 383
| SEQ_ID_NO_386 | SLRAEVNRI R | SEYEQLLSEN | ASLKERL GEI | PGQDDHR- | TG | 386
| SEQ_ID_NO_391 | SLRSEVNRI R | SDYEQLLSEN | AALKERL GEL | PPNDDHHHR | S | 390
| SEQ_ID_NO_392 | SLRSEVSRI R | SDYEQLLSEN | TALKERL GEL | PA- - - - - | - - | 375

| SEQ_ID_NO | | | | | |
|---|---|---|---|---|---|
| SEQ_ID_NO_370 | NNKLQHSADD | SQK- - - - - | - - - - - - - - | KGN | | 376
| SEQ_ID_NO_374 | NNKLQHSGDD | SQK- - - - - | - - - - - - - - | KGN | | 385
| SEQ_ID_NO_376 | DNKLQHSGDD | SQK- - - - - | - - - - - - - - | KGN | | 390
| SEQ_ID_NO_377 | DNKPQRSGDD | SQKK- - - - | - - - - - - - - | ETN | | 381
| SEQ_ID_NO_378 | DNKLQHSGDD | SQK- - - - - | - - - - - - - - | DTN | | 388
| SEQ_ID_NO_384 | SRNDDQHLSND | TQKTEQT- | - - - - - - - - | EI VQAGH | T | 405
| SEQ_ID_NO_385 | GRNDDQHTSND | TQQTGQ- | - - - - - - - - | EHGQGGH | | 400
| SEQ_ID_NO_386 | GRNEQHSGND | TKQTGQTGQA | - - - - - - - - | EAVQGGH | | 413
| SEQ_ID_NO_391 | GRNDQHVGND | TQQSGQT- | - - - - - - - - | EAVQGGH | | 414
| SEQ_ID_NO_392 | - - NDQHVGNE | AQQNGQT- | - - - - - - - - | EGVQGGH | | 397

METHODS OF INCREASING CROP YIELD UNDER ABIOTIC STRESS

CROSS-REFERENCE TO RELATED APPLICATIONS

This application is a divisional of Ser. No. 15/326,437 filed Jan. 13, 2017 (pending) which application is a 371 National Stage application of International Application No. PCT/US2015/040614, filed Jul. 15, 2015, which claims the benefit of, and priority to, U.S. Provisional Patent Application Ser. No. 62/024,791, filed Jul. 15, 2014, the entire contents of which are hereby incorporated by reference.

STATEMENT AS TO FEDERALLY SPONSORED RESEARCH

This invention was made with government support under EDH-A-00-09-00009 awarded by the USAID. The government has certain rights in the invention.

TECHNICAL FIELD

This document relates to methods and materials involved in increasing yield in plants. For example, this document provides plants and materials and methods for making plants and plant products, where the plants have increased yield under abiotic stress conditions.

BACKGROUND

Environmental abiotic stresses diminish productivity of agricultural crops. Drought is a well-known example of an abiotic stress that periodically or chronically affects farming operations. Plants exposed to low water or drought conditions typically have low yields of plant material, seeds, fruit and other edible products. Some areas of the world consistently have low rainfall and limited irrigation opportunities, and therefore have problems growing sufficient food crops for their population.

Another type of abiotic stress relates to high salt levels in soil. If salt concentration exceeds a relatively low threshold, many plants suffer from stunted growth, necrosis, and even death, which results in reduced overall yields of plant material, seeds, fruit and other valuable products.

Yet another abiotic stress could be caused by lower than optimal soil fertilization. Nitrogen, as it could be supplied by nitrogen-containing fertilizers, is an essential, limiting nutrient required for plant growth. Fertilizer supplements are effective in increasing crop yields, yet their heavy use is detrimental to the environment, their application is costly, and their supply limited in some parts of the world. Thus, there is an ongoing need for methods and materials that allow increased harvest output for crops grown under various abiotic stress conditions.

SUMMARY

This document provides methods and materials related to plants having increased tolerance to abiotic stresses. For example, this document provides transgenic plants and plant cells having increased tolerance to drought, osmotic stress, and nitrogen deficiency, nucleic acids used to generate transgenic plants and plant cells having increased tolerance to such abiotic stresses, methods for making plants having increased tolerance to abiotic stresses, and methods for making plant cells that can be used to generate plants having increased tolerance to drought, osmotic stress, and nitrogen deficiency. Such plants and plant cells can be grown under such abiotic stress, with an increased yield.

In one aspect, this document features a method of increasing plant yield in a plant grown under drought stress, osmotic stress, or nitrogen deficiency. The method includes growing a plant comprising an exogenous nucleic acid under drought stress, osmotic stress, or nitrogen deficiency, the exogenous nucleic acid comprising a regulatory region operably linked to a nucleotide sequence encoding a polypeptide or a truncation of the polypeptide, wherein the HMM bit score of the amino acid sequence of the polypeptide is greater than about 65, the HMM based on the amino acid sequences depicted in any one of FIGS. 1-7, and wherein yield of the plant is increased as compared to the corresponding yield of a control plant that does not comprise said nucleic acid.

This document also features a method of increasing plant yield in a plant grown under drought stress, osmotic stress, or nitrogen deficiency. The method includes growing a plant comprising an exogenous nucleic acid under drought stress, osmotic stress, or nitrogen deficiency, the exogenous nucleic acid comprising a regulatory region operably linked to a nucleotide sequence encoding a polypeptide having at least 80% (e.g., at least 90%) sequence identity to an amino acid sequence set forth in SEQ ID NO: 2, 4, 6, 8, 9, 10, 11, 13, 15, 16, 17, 18, 20, 21, 22, 24, 25, 27, 29, 31, 33, 34, 35, 37, 39, 41, 42, 44, 46, 48, 49, 51, 52, 53, 54, 55, 56, 57, 58, 59, 61, 63, 64, 66, 68, 69, 70, 71, 72, 74, 75, 76, 77, 79, 81, 82, 84, 85, 86, 88, 89, 91, 93, 95, 96, 98, 99, 100, 102, 103, 104, 105, 107, 108, 109, 111, 113, 115, 116, 117, 118, 120, 122, 123, 124, 126, 128, 130, 131, 133, 135, 137, 138, 139, 140, 141, 142, 143, 144, 145, 146, 147, 149, 151, 153, 154, 155, 156, 157, 158, 159, 160, 162, 163, 165, 167, 169, 171, 172, 174, 176, 178, 179, 181, 182, 183, 184, 186, 187, 189, 190, 191, 192, 193, 194, 195, 196, 197, 198, 199, 200, 201, 202, 203, 205, 206, 207, 209, 211, 212, 213, 214, 216, 218, 219, 220, 221, 222, 223, 225, 227, 229, 230, 231, 232, 233, 235, 236, 237, 238, 239, 240, 242, 244, 246, 247, 249, 250, 251, 253, 255, 257, 259, 261, 262, 263, 265, 266, 267, 269, 271, 273, 275, 276, 278, 280, 282, 283, 284, 285, 286, 287, 289, 291, 292, 294, 296, 298, 299, 300, 301, 302, 304, 306, 308, 309, 311, 312, 314, 315, 317, 319, 320, 322, 323, 324, 326, 328, 330, 332, 333, 334, 335, 337, 338, 339, 340, 341, 342, 344, 345, 347, 348, 350, 352, 353, 354, 355, 356, 357, 358, 359, 360, 362, 364, 365, 366, 367, 368, 370, 372, 374, 375, 376, 377, 378, 379, 381, 382, 383, 384, 385, 386, 387, 388, 390, 391, 392, 394, 395, 396, 397, 399, 401, and 403, or a truncation of the polypeptide, and wherein yield of the plant is increased as compared to the corresponding yield of a control plant that does not comprise the nucleic acid.

In any of the methods, the method further can include harvesting biomass from said plant.

In another aspect, this document features a method of producing a plant with tolerance to drought stress, osmotic stress, or nitrogen deficiency. The method includes expressing in a plurality of plants an exogenous nucleic acid comprising a nucleotide sequence encoding a polypeptide or a truncation of the polypeptide, wherein the HMM bit score of the amino acid sequence of the polypeptide is greater than about 65, the HMM based on the amino acid sequences depicted in any one of FIGS. 1-7, and wherein yield of the plant is increased as compared to the corresponding yield of a control plant that does not comprise the nucleic acid, and selecting from the plurality a plant that has increased tolerance to drought stress, osmotic stress, or nitrogen deficiency.

This document also features a method of producing a plant with tolerance to drought stress, osmotic stress, or nitrogen deficiency. The method includes expressing in a plurality of plants an exogenous nucleic acid comprising a nucleotide sequence encoding a polypeptide or a truncation of the polypeptide, the exogenous nucleic acid comprising a regulatory region operably linked to a nucleotide sequence encoding a polypeptide having at least 80% (e.g., at least 90%) sequence identity to an amino acid sequence set forth in SEQ ID NO: 2, 4, 6, 8, 9, 10, 11, 13, 15, 16, 17, 18, 20, 21, 22, 24, 25, 27, 29, 31, 33, 34, 35, 37, 39, 41, 42, 44, 46, 48, 49, 51, 52, 53, 54, 55, 56, 57, 58, 59, 61, 63, 64, 66, 68, 69, 70, 71, 72, 74, 75, 76, 77, 79, 81, 82, 84, 85, 86, 88, 89, 91, 93, 95, 96, 98, 99, 100, 102, 103, 104, 105, 107, 108, 109, 111, 113, 115, 116, 117, 118, 120, 122, 123, 124, 126, 128, 130, 131, 133, 135, 137, 138, 139, 140, 141, 142, 143, 144, 145, 146, 147, 149, 151, 153, 154, 155, 156, 157, 158, 159, 160, 162, 163, 165, 167, 169, 171, 172, 174, 176, 178, 179, 181, 182, 183, 184, 186, 187, 189, 190, 191, 192, 193, 194, 195, 196, 197, 198, 199, 200, 201, 202, 203, 205, 206, 207, 209, 211, 212, 213, 214, 216, 218, 219, 220, 221, 222, 223, 225, 227, 229, 230, 231, 232, 233, 235, 236, 237, 238, 239, 240, 242, 244, 246, 247, 249, 250, 251, 253, 255, 257, 259, 261, 262, 263, 265, 266, 267, 269, 271, 273, 275, 276, 278, 280, 282, 283, 284, 285, 286, 287, 289, 291, 292, 294, 296, 298, 299, 300, 301, 302, 304, 306, 308, 309, 311, 312, 314, 315, 317, 319, 320, 322, 323, 324, 326, 328, 330, 332, 333, 334, 335, 337, 338, 339, 340, 341, 342, 344, 345, 347, 348, 350, 352, 353, 354, 355, 356, 357, 358, 359, 360, 362, 364, 365, 366, 367, 368, 370, 372, 374, 375, 376, 377, 378, 379, 381, 382, 383, 384, 385, 386, 387, 388, 390, 391, 392, 394, 395, 396, 397, 399, 401, and 403, or a truncation of said polypeptide, and wherein yield of the plant is increased as compared to the corresponding yield of a control plant that does not comprise the nucleic acid, and selecting from the plurality, a plant that has increased tolerance to drought stress, osmotic stress, or nitrogen deficiency.

In any of the methods, the plant can be grown under drought stress (e.g., pre-flowering or post-flowering drought stress).

In any of the methods, the plant can be grown under osmotic stress. For example, the osmotic stress can be selected from a soil electric conductivity between 4 and 5 dS/m, and a soil conductivity between 6 and 7 dS/m.

In any of the methods, the plant can be grown under nitrogen deficiency. The nitrogen deficiency can be selected from a 50 Kg per hectare nitrogen application, and a 75 Kg per hectare nitrogen application.

In any of the methods, the exogenous nucleic acid can have 80% or greater sequence identity to a nucleotide sequence selected from the group consisting of 1, 3, 5, 7, 12, 14, 19, 23, 26, 28, 30, 32, 36, 38, 40, 43, 45, 47, 50, 60, 62, 65, 67, 73, 78, 80, 83, 87, 90, 92, 94, 97, 101, 106, 110, 112, 114, 119, 121, 125, 127, 129, 132, 134, 136, 148, 150, 152, 161, 164, 166, 168, 170, 173, 175, 177, 180, 185, 188, 204, 208, 210, 215, 217, 224, 226, 228, 234, 241, 243, 245, 248, 252, 254, 256, 258, 260, 264, 268, 270, 272, 274, 277, 279, 281, 288, 290, 293, 295, 297, 303, 305, 307, 310, 313, 316, 318, 321, 325, 327, 329, 331, 336, 343, 346, 349, 351, 361, 363, 369, 371, 373, 380, 389, 393, 398, 400, and 402.

In any of the methods, the plant can be selected from the group consisting of *Panicum virgatum, Sorghum bicolor, Miscanthus giganteus, Saccharum* sp., *Populus balsamifera, Zea mays, Glycine max, Brassica napus, Triticum aestivum, Gossypium hirsutum, Oryza saliva, Helianthus annuus, Medicago saliva, Beta vulgaris,* or *Pennisetum glaucum.*

In any of the methods, the method can include growing the plant under osmotic stress, or nitrogen deficiency, wherein the HMM bit score of the amino acid sequence of the polypeptide is greater than about 65, the HMM based on the amino acid sequences depicted in FIG. 2 or 3.

In any of the methods, the method can include growing the plant under drought or nitrogen deficiency, wherein the HMM bit score of the amino acid sequence of the polypeptide is greater than about 65, the HMM based on the amino acid sequences depicted in FIG. 4.

This document also features a plant cell containing a modified endogenous nucleic acid. The nucleic acid comprising a nucleotide sequence encoding a polypeptide, wherein the HMM bit score of the amino acid sequence of the polypeptide is greater than about 65, the HMM based on the amino acid sequences depicted in one of FIGS. 1-7, and wherein a plant produced from the plant cell has a difference in tolerance to drought stress, osmotic stress, or nitrogen deficiency as compared to the corresponding composition of a control plant where said nucleic acid has not been modified. The plant can be selected from the group consisting of *Panicum virgatum, Sorghum bicolor, Miscanthus giganteus, Saccharum* sp., *Populus balsamifera, Zea mays, Glycine max, Brassica napus, Triticum aestivum, Gossypium hirsutum, Oryza sativa, Helianthus annuus, Medicago sativa, Beta vulgaris,* or *Pennisetum glaucum.*

The polypeptide can have 80 percent or greater sequence identity (e.g., 90 percent or greater or 95 percent or greater) to an amino acid sequence selected from the group consisting of SEQ ID NO:2, 4, 6, 8, 9, 10, 11, 13, 15, 16, 17, 18, 20, 21, 22, 24, 25, 27, 29, 31, 33, 34, 35, 37, 39, 41, 42, 44, 46, 48, 49, 51, 52, 53, 54, 55, 56, 57, 58, 59, 61, 63, 64, 66, 68, 69, 70, 71, 72, 74, 75, 76, 77, 79, 81, 82, 84, 85, 86, 88, 89, 91, 93, 95, 96, 98, 99, 100, 102, 103, 104, 105, 107, 108, 109, 111, 113, 115, 116, 117, 118, 120, 122, 123, 124, 126, 128, 130, 131, 133, 135, 137, 138, 139, 140, 141, 142, 143, 144, 145, 146, 147, 149, 151, 153, 154, 155, 156, 157, 158, 159, 160, 162, 163, 165, 167, 169, 171, 172, 174, 176, 178, 179, 181, 182, 183, 184, 186, 187, 189, 190, 191, 192, 193, 194, 195, 196, 197, 198, 199, 200, 201, 202, 203, 205, 206, 207, 209, 211, 212, 213, 214, 216, 218, 219, 220, 221, 222, 223, 225, 227, 229, 230, 231, 232, 233, 235, 236, 237, 238, 239, 240, 242, 244, 246, 247, 249, 250, 251, 253, 255, 257, 259, 261, 262, 263, 265, 266, 267, 269, 271, 273, 275, 276, 278, 280, 282, 283, 284, 285, 286, 287, 289, 291, 292, 294, 296, 298, 299, 300, 301, 302, 304, 306, 308, 309, 311, 312, 314, 315, 317, 319, 320, 322, 323, 324, 326, 328, 330, 332, 333, 334, 335, 337, 338, 339, 340, 341, 342, 344, 345, 347, 348, 350, 352, 353, 354, 355, 356, 357, 358, 359, 360, 362, 364, 365, 366, 367, 368, 370, 372, 374, 375, 376, 377, 378, 379, 381, 382, 383, 384, 385, 386, 387, 388, 390, 391, 392, 394, 395, 396, 397, 399, 401, and 403.

In another aspect, this document features a method of increasing plant yield in a plant grown under drought stress, osmotic stress, or nitrogen deficiency stress. The method includes growing a plant comprising a plant cell described herein under drought stress, osmotic stress, or nitrogen deficiency stress, and wherein yield of the plant is increased as compared to the corresponding yield of a control plant that does not comprise the modified endogenous nucleic acid.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DESCRIPTION OF DRAWINGS

FIGS. 1A-1D contain an alignment of the amino acid sequence of Clone 1805402 (SEQ ID NO: 2) with homologous and/or orthologous amino acid sequences. In all the alignment figures shown herein, a dash in an aligned sequence represents a gap, i.e., a lack of an amino acid at that position. Identical amino acids or conserved amino acid substitutions among aligned sequences are identified by boxes. FIG. 1 and the other alignment figures provided herein were generated using the program MUSCLE version 3.52.

FIGS. 2A-2F contain an alignment of the amino acid sequence of Annot 872104m (SEQ ID NO: 337) with homologous and/or orthologous amino acid sequences.

FIGS. 3A-3D contain an alignment of the amino acid sequence of Clone 26006 (SEQ ID NO: 61) with homologous and/or orthologous amino acid sequences.

FIGS. 4A-4E contain an alignment of the amino acid sequence of Clone 375578 (SEQ ID NO: 111) with homologous and/or orthologous amino acid sequences.

FIG. 5A-5E contain an alignment of the amino acid sequence of Clone 625057 (SEQ ID NO: 27) with homologous and/or orthologous amino acid sequences.

FIG. 6A-6Q contain an alignment of the amino acid sequence of Annot 878355 (SEQ ID NO: 209) with homologous and/or orthologous amino acid sequences.

FIG. 7A-7D contain an alignment of the amino acid sequence of Clone 258841 (SEQ ID NO: 370) with homologous and/or orthologous amino acid sequences.

DETAILED DESCRIPTION

Figure 6A:
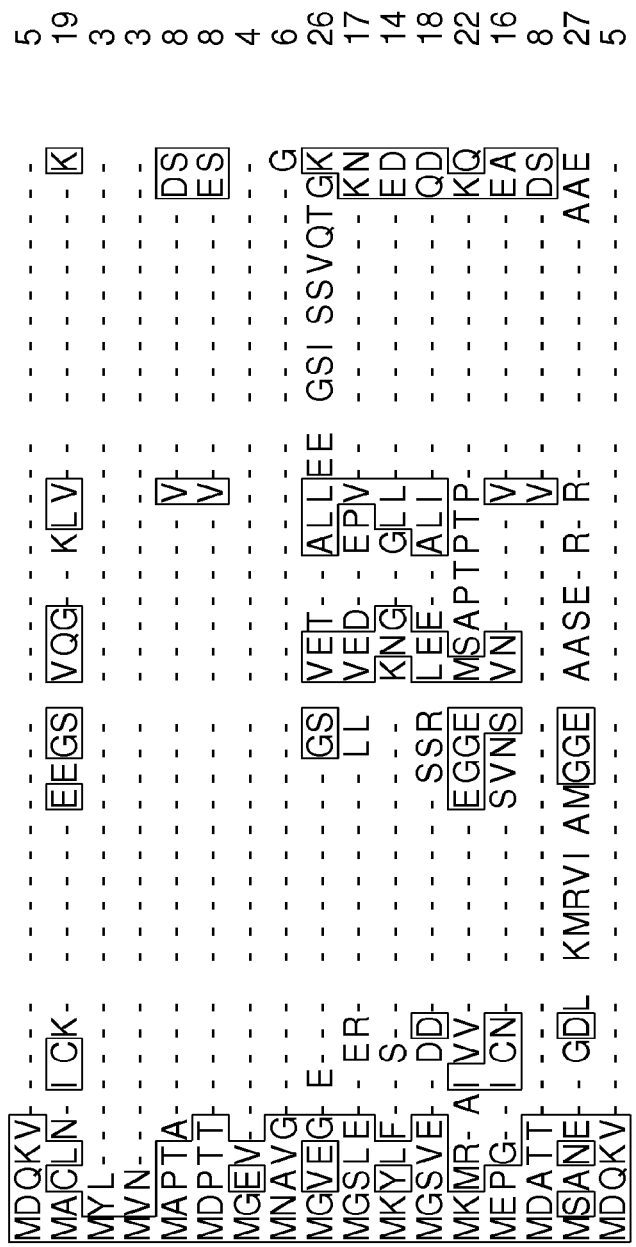

The invention features methods and materials related to increasing abiotic stress tolerance in plants. In some embodiments, the plants may have, for example, increased levels of drought tolerance, osmotic stress tolerance, or nitrogen deficiency tolerance. The methods described herein can include transforming a plant cell with a nucleic acid encoding an abiotic stress tolerance-increasing polypeptide, wherein expression of the polypeptide results in an increased level of abiotic stress tolerance. Plant cells produced using such methods can be grown to produce plants having an increased tolerance to drought, osmotic stress, and nitrogen deficiency. Such plants can have increased plant yield in under-irrigated fields or soil containing high salt or nitrogen deficiency.

I. Definitions

"Amino acid" refers to one of the twenty biologically occurring amino acids and to synthetic amino acids, including D/L optical isomers.

"Cell type-preferential promoter" or "tissue-preferential promoter" refers to a promoter that drives expression preferentially in a target cell type or tissue, respectively, but may also lead to some transcription in other cell types or tissues as well.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Down-regulation" refers to regulation that decreases production of expression products (mRNA, polypeptide, or both) relative to basal or native states.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Heterologous polypeptide" as used herein refers to a polypeptide that is not a naturally occurring polypeptide in a plant cell, e.g., a transgenic *Oryza sativa* plant transformed with and expressing the coding sequence for a nitrogen transporter polypeptide from a *Zea mays* plant.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Modulation" of the level of stress tolerance refers to the change in the level of the stress tolerance that is observed as a result of expression of, or transcription from, an exogenous or endogenous nucleic acid in a plant cell and/or plant. The change in level is measured relative to the corresponding level in control plants.

"Nucleic acid" and "polynucleotide" are used interchangeably herein, and refer to both RNA and DNA, including cDNA, genomic DNA, synthetic DNA, and DNA or RNA containing nucleic acid analogs. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell*, 1:977-984 (1989).

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

"Exemplified Polypeptides" refer to SEQ ID NOs: 2, 4, 6, 8, 9, 10, 11, 13, 15, 16, 17, 18, 20, 21, 22, 24, 25, 27, 29, 31, 33, 34, 35, 37, 39, 41, 42, 44, 46, 48, 49, 51, 52, 53, 54, 55, 56, 57, 58, 59, 61, 63, 64, 66, 68, 69, 70, 71, 72, 74, 75, 76, 77, 79, 81, 82, 84, 85, 86, 88, 89, 91, 93, 95, 96, 98, 99, 100, 102, 103, 104, 105, 107, 108, 109, 111, 113, 115, 116, 117, 118, 120, 122, 123, 124, 126, 128, 130, 131, 133, 135, 137, 138, 139, 140, 141, 142, 143, 144, 145, 146, 147, 149, 151, 153, 154, 155, 156, 157, 158, 159, 160, 162, 163, 165, 167, 169, 171, 172, 174, 176, 178, 179, 181, 182, 183, 184, 186, 187, 189, 190, 191, 192, 193, 194, 195, 196, 197, 198, 199, 200, 201, 202, 203, 205, 206, 207, 209, 211, 212, 213, 214, 216, 218, 219, 220, 221, 222, 223, 225, 227, 229, 230, 231, 232, 233, 235, 236, 237, 238, 239, 240, 242, 244, 246, 247, 249, 250, 251, 253, 255, 257, 259, 261, 262, 263, 265, 266, 267, 269, 271, 273, 275, 276, 278, 280, 282, 283, 284, 285, 286, 287, 289, 291, 292, 294, 296, 298, 299, 300, 301, 302, 304, 306, 308, 309, 311, 312, 314, 315, 317, 319, 320, 322, 323, 324, 326, 328, 330, 332, 333, 334, 335, 337, 338, 339, 340, 341, 342, 344, 345, 347, 348, 350, 352, 353, 354, 355, 356, 357, 358, 359, 360, 362, 364, 365, 366, 367, 368, 370, 372, 374, 375, 376, 377, 378, 379, 381, 382, 383, 384, 385, 386, 387, 388, 390, 391, 392, 394, 395, 396, 397, 399, 401, and 403.

II. Polypeptides

Polypeptides described herein include abiotic stress tolerance-increasing polypeptides. Abiotic stress tolerance-increasing polypeptides can be effective to modulate (e.g., increase) abiotic stress tolerance when expressed in a plant or plant cell. Such polypeptides typically contain at least one domain indicative of abiotic stress tolerance-increasing polypeptides, as described in more detail herein. Abiotic stress tolerance-increasing polypeptides typically have an HMM bit score that is greater than 65 as described in more detail herein. In some embodiments, abiotic stress tolerance-increasing polypeptides have greater than 80% identity to the Exemplified Polypeptides as described in more detail herein.

A. Domains Indicative of Abiotic Stress Tolerance-Increasing Polypeptides

An abiotic stress tolerance-increasing polypeptide can contain an AP2 domain and/or CMX-1 and CMX-2 motifs, which are predicted to be characteristic of an abiotic stress tolerance-increasing polypeptide. SEQ ID NO: 2 sets forth the amino acid sequence of a *Panicum virgatum* clone, identified herein as CeresClone: 1805402, that is predicted to encode a polypeptide containing all AP2 domain and CMX-1 and CMX-2 motifs. For example, an abiotic stress tolerance-increasing polypeptide can comprise an AP2 domain having 60 percent or greater (e.g., 65, 70, 75, 80, 85, 90, 95, 97, 98, 99, or 100 percent) sequence identity to residues 132 to 181 of SEQ ID NO: 2 and/or an CMX-1 motif and an CMX-2 motif having 60 percent or greater (e.g., 65, 70, 75, 80, 85, 90, 95, 97, 98, 99, or 100 percent) sequence identity to residues 56 to 78 and residues 88 to 99 of SEQ ID NO: 2, respectively. In some embodiments, an abiotic stress tolerance-increasing polypeptide can comprise an AP2 domain having 60 percent or greater (e.g., 65, 70, 75, 80, 85, 90, 95, 97, 98, 99, or 100 percent) sequence identity to the AP2 domain and/or an CMX-1 motif and an CMX-2 motif having 60 percent or greater (e.g., 65, 70, 75, 80, 85, 90, 95, 97, 98, 99, or 100 percent) sequence identity to the CMX-1 motif and CMX-2 motif of one or more of the polypeptides set forth in SEQ ID NOs: 4, 6, 8, 9, 10, 11, 13, 15, 16, 17, 18, 20, 21, 22, 24, or 25. The AP2, CMX-1, and CMX-2 domains of such sequences are set forth in the Sequence Listing. AP2 domain amino acid residues can bind to DNA and are typically found in transcription factor proteins. CMX-1 and CMX-2 motifs have been identified in the soybean and rice ERF transcription factors.

An abiotic stress tolerance-increasing polypeptide can contain a RPE65 domain, which is predicted to be characteristic of an abiotic stress tolerance-increasing polypeptide. SEQ ID NO: 337 sets forth the amino acid sequence of an *Arabidopsis thaliana* clone, identified herein as CeresAnnot: 872104m, that is predicted to encode a polypeptide containing a retinal pigment epithelial membrane protein (RPE65) domain. For example, an abiotic stress tolerance-increasing polypeptide can comprise a RPE65 domain having 60 percent or greater (e.g., 65, 70, 75, 80, 85, 90, 95, 97, 98, 99, or 100 percent) sequence identity to residues 124 to 589 of SEQ ID NO: 337. In some embodiments, an abiotic stress tolerance-increasing polypeptide can comprise a RPE65 domain having 60 percent or greater (e.g., 65, 70, 75, 80, 85, 90, 95, 97, 98, 99, or 100 percent) sequence identity to the RPE65 domain of one or more of the polypeptides set forth in SEQ ID NOs: 338, 339, 340, 341, 342, 344, 345, 347, 348, 350, 352, 353, 354, 355, 356, 357, 358, 359, 360, 362, 364, 365, 366, 367, or 368. The RPE65 domains of such sequences are set forth in the Sequence Listing. A polypeptide having a RPE65 domain can have 9-cis-epoxycarotenoid dioxygenase enzymatic activity, which is classified under EC 3.1.1.64.

An abiotic stress tolerance-increasing polypeptide can contain an alpha/beta hydrolase fold family domain, which is predicted to be characteristic of an abiotic stress tolerance-increasing polypeptide. SEQ ID NO: 61 sets forth the amino acid sequence of all *Arabidopsis thaliana* clone, identified herein as CeresClone:26006, that is predicted to encode a polypeptide containing an alpha/beta hydrolase fold family domain. For example, an abiotic stress tolerance-increasing polypeptide can comprise an alpha/beta hydrolase fold domain having 60 percent or greater (e.g., 65, 70, 75, 80, 85, 90, 95, 97, 98, 99, or 100 percent) sequence identity to residues 10 to 252 of SEQ ID NO: 61. In some embodiments, an abiotic stress tolerance-increasing polypeptide can comprise an alpha/beta hydrolase fold domain having 60 percent or greater (e.g., 65, 70, 75, 80, 85, 90, 95, 97, 98, 99, or 100 percent) sequence identity to the alpha/beta hydrolase fold domain of one or more of the polypeptides set forth in SEQ ID NOs: 63, 64, 66, 68, 69, 70, 71, 72, 74, 75, 76, 77, 79, 81, 82, 84, 85, 86, 88, 89, 91, 93, 95, 96, 98, 99, 100, 102, 103, 104, 105, 107, 108, or 109. The alpha/beta hydrolase fold domains of such sequences are set forth in the Sequence Listing. The alpha/beta hydrolase fold is common to a number of hydrolytic enzymes of widely differing phylogenetic origin and catalytic function. The core of each enzyme is an alpha/beta-sheet (rather than a barrel), containing 8 strands connected by helices. The enzymes are believed to have diverged from a common ancestor, preserving the arrangement of the catalytic residues. All have a catalytic triad, the elements of which are borne on loops, which are the best conserved structural features of the fold. A polypeptide having an alpha/beta hydrolase fold domain can have acetone-cyanohydrin lyase/methyl esterase (EC: 3.1.1.-) enzymatic activity.

An abiotic stress tolerance-increasing polypeptide can contain IQ calmodulin-binding motif domain and/or a DUF4005 domain, which are predicted to be characteristic of an abiotic stress tolerance-increasing polypeptide. SEQ ID NO: 111 sets forth the amino acid sequence of a *Zea mays* clone, identified herein as CeresClone:375578, that is predicted to encode a polypeptide containing an IQ calmodulin-binding motif domain and a DUF4005 domain. For example, an abiotic stress tolerance-increasing polypeptide can comprise an IQ calmodulin-binding motif domain having 60 percent or greater (e.g., 65, 70, 75, 80, 85, 90, 95, 97, 98, 99, or 100 percent) sequence identity to residues 139 to 157 of SEQ ID NO: 111 and/or a DUF4005 domain having 60 percent or greater (e.g., 65, 70, 75, 80, 85, 90, 95, 97, 98, 99, or 100 percent) sequence identity to residues 360 to 427 of SEQ ID NO: 111. In some embodiments, an abiotic stress tolerance-increasing polypeptide can comprise an IQ calmodulin binding motif and/or a DUF4005 domain having 60 percent or greater (e.g., 65, 70, 75, 80, 85, 90, 95, 97, 98, 99, or 100 percent) sequence identity to the IQ calmodulin binding motif and/or DUF4005 domain of one or more of the polypeptides set forth in SEQ ID NOs: 113, 115, 116, 117, 118, 120, 122, 123, 124, 126, 128, 130, 131, 133, 135, 137, 138, 139, 140, 141, 142, 143, 144, 145, 146, 147, 149, 151, 153, 154, 155, 156, 157, 158, 159, 160, 162, 163, 165, 167, 169, 171, 172, 174, 176, 178, 179, 181, 182, 183, 184, 186, 187, 189, 190, 191, 192, 193, 194, 195, 196, 197, 198, 199, 200, 201, 202, 203, 205, 206, or 207. The IQ calmodulin binding motif and DUF4005 domains of such sequences are set forth in the Sequence Listing. The IQ calmodulin-binding motif domain is a consensus for calcium-independent binding of calmodulin, which is a calcium sensor and helps regulate events through its interaction with a diverse group of cellular proteins. See Rhoads and Friedberg, *FASEB J.*, 11(5):331-40 (1997). The DUF4005 domain is found in the C-terminal region of plant IQ-domain containing calmodulin-binding proteins.

An abiotic stress tolerance-increasing polypeptide can contain an aminotransferase class I and II domain and/or an allinase domain, which are predicted to be characteristic of an abiotic stress tolerance-increasing polypeptide. SEQ ID NO: 27 sets forth the amino acid sequence of a *Glycine max* clone, identified herein as CeresClone:625057, that is predicted to encode a polypeptide containing an aminotransferase class I and II domain and an allinase domain. For example, an abiotic stress tolerance-increasing polypeptide can comprise an aminotransferase class I and II domain having 60 percent or greater (e.g., 65, 70, 75, 80, 85, 90, 95, 97, 98, 99, or 100 percent) sequence identity to residues 89 to 453 of SEQ ID NO: 27 and/or an allinase domain having 60 percent or greater (e.g., 65, 70, 75, 80, 85, 90, 95, 97, 98, 99, or 100 percent) sequence identity to residues 230 to 318 of SEQ ID NO: 27. In some embodiments, an abiotic stress tolerance-increasing polypeptide can comprise all aminotransferase class I and II domain and/or allinase domain having 60 percent or greater (e.g., 65, 70, 75, 80, 85, 90, 95, 97, 98, 99, or 100 percent) sequence identity to the aminotransferase class I and II and allinase domains of one or more of the polypeptides set forth in SEQ ID NOs: 29, 31, 33, 34, 35, 37, 39, 41, 42, 44, 46, 48, 49, 51, 52, 53, 54, 55, 56, 57, 58, or 59. The aminotransferase class I and II and allinase domains of such sequences are set forth in the Sequence Listing. Aminotransferases share certain mechanistic features with other pyridoxal-phosphate dependent enzymes, such as the covalent binding of the pyridoxal-phosphate group to a lysine residue. On the basis of sequence similarity, these various enzymes can be grouped into class I and class II. Examples of polypeptides comprising aminotransferase class I and II domains include LL-DAP polypeptides (EC 2.6.1.83) (Watanabe et al., Mechanism of Substrate Recognition and PLP-induced Conformational Changes in LL-Diaminopimelate aminotransferase from *Arabidopsis thaliana. J. Mol. Biol.* 384, 1314-1329 (2008)). LL-DAP catalyzes the interconversion of LL-2,6-diaminoheptanedioate and 2-oxoglutarate to (S)-2,3,4,5-tetrahydropyridine-2, 6-dicarboxylate, L-glutamate, and water. The allinase domain is an EFG like domain that is rich in disulfides that is found in allinase, a pyridoxal-5'-phosphate-dependent enzyme. See, e.g., Kuettner et al., *J. Biol. Chem.*, 277(48): 46402-46407 (2002).

An abiotic stress tolerance-increasing polypeptide can contain a PTR2 POT family domain, which is predicted to be characteristic of an abiotic stress tolerance-increasing polypeptide. SEQ ID NO: 209 sets forth the amino acid sequence of an *Arabidopsis thaliana* clone, identified herein as CeresAnnot:878355, that is predicted to encode a polypeptide containing a PTR2 POT family domain. For example, an abiotic stress tolerance-increasing polypeptide can comprise a PTR2 POT domain having 60 percent or greater (e.g., 65, 70, 75, 80, 85, 90, 95, 97, 98, 99, or 100 percent) sequence identity to residues 101 to 508 of SEQ ID NO: 209. In some embodiments, an abiotic stress tolerance-increasing polypeptide can comprise a PTR2 POT domain having 60 percent or greater (e.g., 65, 70, 75, 80, 85, 90, 95, 97, 98, 99, or 100 percent) sequence identity to the alpha/beta hydrolase fold domain of one or more of the polypeptides set forth in SEQ ID NOs: 211, 212, 213, 214, 216, 218, 219, 220, 221, 222, 223, 225, 227, 229, 230, 231, 232, 233, 235, 236, 237, 238, 239, 240, 242, 244, 246, 247, 249, 250, 251, 253, 255, 257, 259, 261, 262, 263, 265, 266, 267, 269, 271, 273, 275, 276, 278, 280, 282, 283, 284, 285, 286, 287, 289, 291, 292, 294, 296, 298, 299, 300, 301, 302, 304, 306, 308, 309, 311, 312, 314, 315, 317, 319, 320, 322, 323, 324, 326, 328, 330, 332, 333, 334, or 335. The PTR2 POT domains of such sequences are set forth in the Sequence Listing. The transport of peptides into cells is a well-documented biological phenomenon which is accomplished by specific, energy-dependent transporters found in a number of organisms as diverse as bacteria and humans. The PTR family of proteins is distinct from the ABC-type peptide transporters and was uncovered by sequence analyses of a number of recently discovered peptide transport proteins. These proteins seem to be mainly involved in the intake of small peptides with the concomitant uptake of a proton.

An abiotic stress tolerance-increasing polypeptide can contain a G-box binding protein MFMR domain and/or a bZIP transcription factor domain, which are predicted to be characteristic of an abiotic stress tolerance-increasing polypeptide. SEQ ID NO: 370 sets forth the amino acid sequence of a *Zea mays* clone, identified herein as CeresClone: 258841, that is predicted to encode a polypeptide containing a MFMR domain and a bZIP domain. For example, an abiotic stress tolerance-increasing polypeptide can comprise a MFMR domain having 60 percent or greater (e.g., 65, 70, 75, 80, 85, 90, 95, 97, 98, 99, or 100 percent) sequence identity to residues 1 to 188 of SEQ ID NO: 370 and/or a bZIP domain having 60 percent or greater (e.g., 65, 70, 75, 80, 85, 90, 95, 97, 98, 99, or 100 percent) sequence identity to residues 279 to 341 of SEQ ID NO: 370. In some embodiments, an abiotic stress tolerance-increasing polypeptide can comprise a MFMR and/or a bZIP domain having 60 percent or greater (e.g., 65, 70, 75, 80, 85, 90, 95, 97, 98, 99, or 100 percent) sequence identity to the MFMR and/or bZIP domains of one or more of the polypeptides set forth in SEQ ID NOs: 372, 374, 375, 376, 377, 378, 379, 381, 382, 383, 384, 385, 386, 387, 388, 390, 391, 392, 394, 395, 396, 397, 399, 401, and 403. The MFMR and bZIP domains of such sequences are set forth in the Sequence Listing. The MFMR region is typically found to the N-terminus of the PF00170 transcription factor domain. It is typically between 150 and 200 amino acids in length. The N-terminal half is typically rather rich in proline residues and has been termed the PRD (proline rich domain) whereas the C-terminal half is typically more polar and has been called the MFMR (multifunctional mosaic region). This family may be composed of three sub-families called A, B and C classified according to motif composition. Some of these motifs may be involved in mediating protein-protein interactions. The MFMR region can contain a nuclear localisation signal in bZIP opaque and GBF-2. The MFMR also can contain a transregulatory activity in TAF-1. The MFMR in CPRF-2 can contain cytoplasmic retention signals. The basic-leucine zipper (bZIP) transcription factors of eukaryotic cells are proteins that contain a basic region mediating sequence-specific DNA-binding followed by a leucine zipper region required for dimerization.

In some embodiments, an abiotic stress tolerance-increasing polypeptide is truncated at the amino- or carboxy-terminal end of a naturally occurring polypeptide. A truncated polypeptide may retain certain domains of the naturally occurring polypeptide while lacking others. Thus, length variants that are up to 5 amino acids shorter or longer typically exhibit the abiotic stress tolerance-increasing activity of a truncated polypeptide. In some embodiments, a truncated polypeptide is a dominant negative polypeptide. Expression in a plant of such a truncated polypeptide confers a difference in the level of abiotic stress tolerance of a plant as compared to the corresponding level of a control plant that does not comprise the truncation. The phenotype is cause by a truncation.

B. Functional Homologs Identified by Reciprocal BLAST

In some embodiments, one or more functional homologs of a reference abiotic stress tolerance-increasing polypeptide defined by one or more of the Pfam descriptions indicated above are suitable for use as abiotic stress tolerance-increasing polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for an abiotic stress tolerance-increasing polypeptide, or by combining domains from the coding sequences for different naturally-occurring abiotic stress tolerance-increasing polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of abiotic stress tolerance-increasing polypeptides. Sequence analysis can involve BLAST, Reciprocal BLAST, or PSI-BLAST analysis of nonredundant databases using an abiotic stress tolerance-increasing polypeptide amino acid sequence as the reference sequence. Amino acid sequence is, in some instances, deduced from the nucleotide sequence. Those polypeptides in the database that have greater than 40% sequence identity are candidates for further evaluation for suitability as an abiotic stress tolerance-increasing polypeptide Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in abiotic stress tolerance-increasing polypeptides, e.g., conserved functional domains.

Conserved regions can be identified by locating a region within the primary amino acid sequence of an abiotic stress tolerance-increasing polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/and pfam.janelia.org/. A description of the information included at the Pfam database is described in Sonnhammer et al., *Nucl. Acids Res.*, 26:320-322 (1998); Sonnhammer et al., *Proteins*, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Figure 1A:
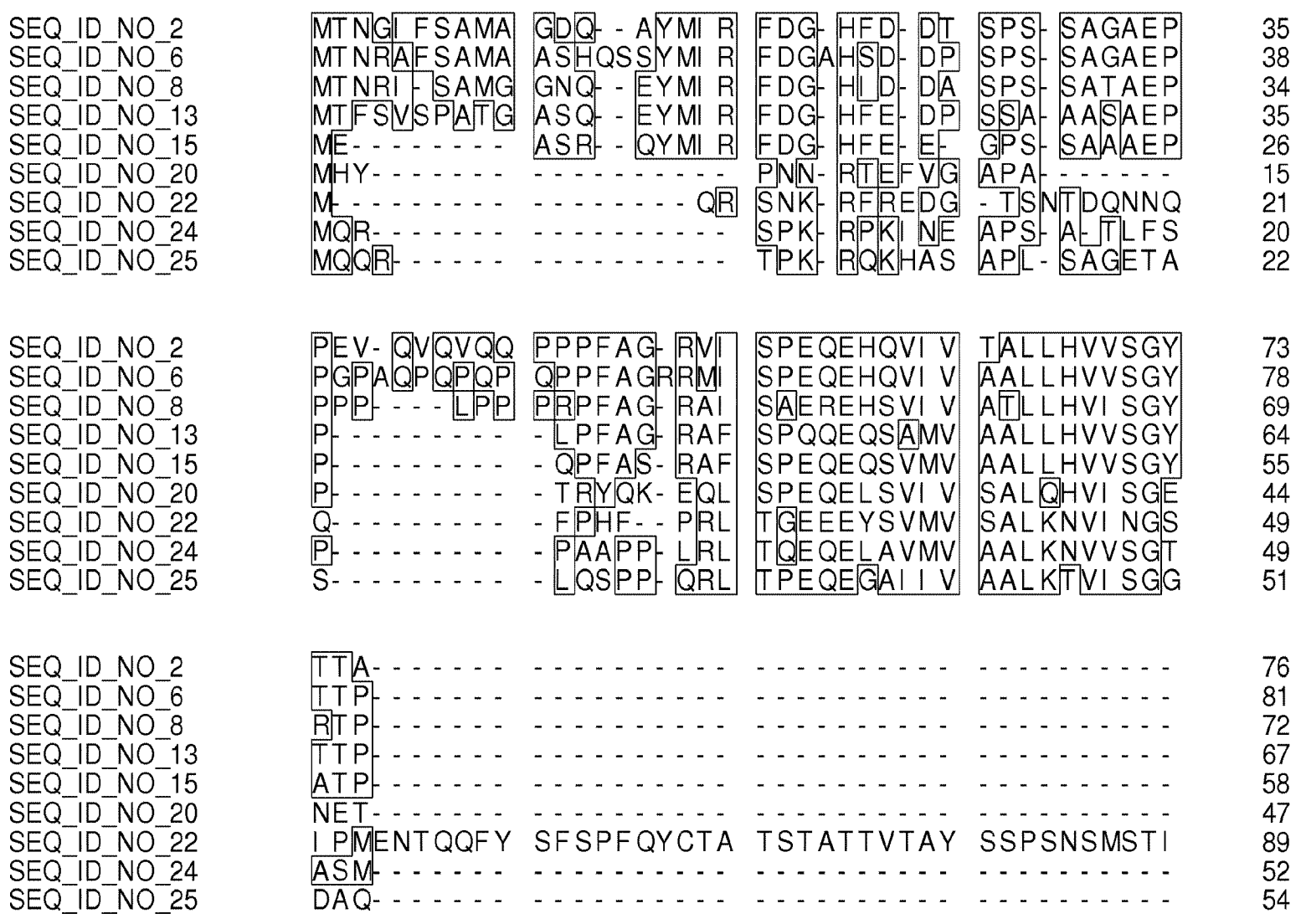

Examples of amino acid sequences of functional homologs of the polypeptide set forth in SEQ ID NO: 2 are provided in FIG. 1 and in the Sequence Listing. Such functional homologs include, for example, CeresClone: 278992 (SEQ ID NO: 4), CeresAnnot:6014857 (SEQ ID NO: 6), CeresAnnot:6318302 (SEQ ID NO: 8), GI:125603736 (SEQ ID NO: 9), GI:357148089 (SEQ ID NO: 10), GI:326518784 (SEQ ID NO: 11), CeresClone: 634402 (SEQ ID NO: 13), CeresClone:1494990 (SEQ ID NO: 15), GI:115479555 (SEQ ID NO: 16), GI:297802528 (SEQ ID NO: 17), GI:224123482 (SEQ ID NO: 18), CeresClone:123905 (SEQ ID NO: 20), GI:255555461 (SEQ ID NO: 21), GI:129560505 (SEQ ID NO: 22), CeresAnnot: 1460991 (SEQ ID NO: 24), or GI:225428806 (SEQ ID NO: 25). In some cases, a functional homolog of SEQ ID NO: 2 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2. In some cases, a functional homolog of SEQ ID NO: 2 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 2 described above or set forth in the Sequence Listing.

Examples of amino acid sequences of functional homologs of the polypeptide set forth in SEQ ID NO: 337 are provided in FIG. 2 and in the Sequence Listing. Such functional homologs include, for example, GI:112181147 (SEQ ID NO:338), GI:15810433 (SEQ ID NO:339), GI:297834326 (SEQ ID NO:340), GI:336420053 (SEQ ID NO:341), GI:345451248 (SEQ ID NO:342), CeresAnnot: 1480808 (SEQ ID NO:344), GI:355398706 (SEQ ID NO:345), CeresAnnot:1519993 (SEQ ID NO:347), GI:7209269 (SEQ ID NO:348), CeresClone:1943815 (SEQ ID NO:350), CeresAnnot:1138943 (SEQ ID NO:352), GI:38112198 (SEQ ID NO:353), GI:79155296 (SEQ ID NO:354), GI:317016344 (SEQ ID NO:355), GI:75185609 (SEQ ID NO:356), GI:22335699 (SEQ ID NO:357), GI:359806478 (SEQ ID NO:358), GI:112181145 (SEQ ID NO:359), GI:115454329 (SEQ ID NO:360), CeresClone: 1806409 (SEQ ID NO:362), CeresAnnot:8633702 (SEQ ID NO:364), GI:226529341 (SEQ ID NO:365), GI:357120366 (SEQ ID NO:366), GI:356577857 (SEQ ID NO:367), or GI:168065310 (SEQ ID NO:368). In some cases, a functional homolog of SEQ ID NO: 337 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 337. In some cases, a functional homolog of SEQ ID NO: 337 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 337 described above or set forth in the Sequence Listing.

Examples of amino acid sequences of functional homologs of the polypeptide set forth in SEQ ID NO: 61 are provided in FIG. 3 and in the Sequence Listing. Such functional homologs include, for example, CeresClone: 644331 (SEQ ID NO: 63), GI:15227859 (SEQ ID NO: 64), CeresAnnot:1504349 (SEQ ID NO: 66), CeresAnnot: 1265088 (SEQ ID NO: 68), US20070214517-97126 (SEQ ID NO: 69), GI:125527987 (SEQ ID NO: 70), GI:14279437 (SEQ ID NO: 71), ES902065 (SEQ ID NO: 72), CeresClone:1065042 (SEQ ID NO: 74), GI:157329790 (SEQ ID NO: 75), GI:15227861 (SEQ ID NO: 76), GI:146272407 (SEQ ID NO: 77), CeresClone:95094 (SEQ ID NO: 79), CeresClone:1714893 (SEQ ID NO: 81), GI:157329890 (SEQ ID NO: 82), CeresAnnot:859635 (SEQ ID NO: 84), GI:115440397 (SEQ ID NO: 85), GI:40549303 (SEQ ID NO: 86), CeresAnnot:1457048 (SEQ ID NO: 88), GI:50401192 (SEQ ID NO: 89), CeresAnnot:1451281 (SEQ ID NO: 91), CeresAnnot:1510252 (SEQ ID NO: 93), CeresClone:1822691 (SEQ ID NO: 95), GI:197312921 (SEQ ID NO: 96), CeresAnnot:8456439 (SEQ ID NO: 98), SEQ ID NO: 99, GI:15028131 (SEQ ID NO: 100), CeresClone: 270875 (SEQ ID NO: 102), GI:27754457 (SEQ ID NO: 103), GI:16648679 (SEQ ID NO: 104), GI:15227863 (SEQ ID NO: 105), CeresAnnot:1451282 (SEQ ID NO: 107), GI:53830670 (SEQ ID NO: 108), or GI:146272405 (SEQ ID NO: 109). In some cases, a functional homolog of SEQ ID NO: 61 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 61. In some cases, a functional homolog of SEQ ID NO: 61 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 61 described above or set forth in the Sequence Listing.

Examples of amino acid sequences of functional homologs of the polypeptide set forth in SEQ ID NO: 111 are provided in FIG. 4 and in the Sequence Listing. Such functional homologs include, for example, CeresAnnot: 8669409 (SEQ ID NO: 113), CeresClone:2034697 (SEQ ID NO: 115), GI:115440873 (SEQ ID NO: 116), GI:357125736 (SEQ ID NO: 117), GI:225449126 (SEQ ID NO: 118), CeresAnnot:1465047 (SEQ ID NO: 120), CeresClone: 1919901 (SEQ ID NO: 122), GI:356565733 (SEQ ID NO: 123), GI:15231175 (SEQ ID NO: 124), CeresClone:106263 (SEQ ID NO: 126), CeresAnnot:247223212 (SEQ ID NO: 128), CeresAnnot:200200100 (SEQ ID NO: 130), GI:7413581 (SEQ ID NO: 131), CeresClone:228069 (SEQ ID NO: 133), CeresClone:467508 (SEQ ID NO: 135), CeresClone:1829581 (SEQ ID NO: 137), GI:357510601 (SEQ ID NO: 138), GI:357129039 (SEQ ID NO: 139), GI:326525172 (SEQ ID NO: 140), GI:357443381 (SEQ ID NO: 141), GI:168063380 (SEQ ID NO: 142), GI:312282973 (SEQ ID NO: 143), GI:125550655 (SEQ ID NO: 144), GI:145357576 (SEQ ID NO: 145), GI:125528277 (SEQ ID NO: 146), GI:224032591 (SEQ ID NO: 147), CeresClone: 1747444 (SEQ ID NO: 149), CeresClone:1998974 (SEQ ID NO: 151), CeresClone:1883040 (SEQ ID NO: 153), GI:326520123 (SEQ ID NO: 154), GI:215701453 (SEQ ID NO: 155), GI:147809623 (SEQ ID NO: 156), GI:224109704 (SEQ ID NO: 157), GI:225439898 (SEQ ID NO: 158), GI:218196002 (SEQ ID NO: 159), GI:54306075 (SEQ ID NO: 160), CeresAnnot:1484880 (SEQ ID NO: 162), GI:224028605 (SEQ ID NO: 163), CeresAnnot:1528800 (SEQ ID NO: 165), CeresClone:1792902 (SEQ ID NO: 167), CeresClone:1806867 (SEQ ID NO: 169), CeresClone: 1727738 (SEQ ID NO: 171), GI:238007500 (SEQ ID NO: 172), CeresAnnot:8724651 (SEQ ID NO: 174), CeresClone: 1897134 (SEQ ID NO: 176), CeresClone:1859266 (SEQ ID NO: 178), GI:194696788 (SEQ ID NO: 179), CeresAnnot: 1475350 (SEQ ID NO: 181), GI:326490361 (SEQ ID NO: 182), GI:224140165 (SEQ ID NO: 183), GI:255577665 (SEQ ID NO: 184), CeresClone:1886384 (SEQ ID NO: 186), GI:255568402 (SEQ ID NO: 187), CeresClone: 1942871 (SEQ ID NO: 189), GI:326527367 (SEQ ID NO: 190), GI:297816500 (SEQ ID NO: 191), GI:297810377 (SEQ ID NO: 192), GI:302762472 (SEQ ID NO: 193), GI:302815615 (SEQ ID NO: 194), GI:116787496 (SEQ ID NO: 195), GI:224029961 (SEQ ID NO: 196), GI:15232741 (SEQ ID NO: 197), GI:302806862 (SEQ ID NO: 198), GI:302772817 (SEQ ID NO: 199), GI:240254538 (SEQ ID NO: 200), GI:297833734 (SEQ ID NO: 201), GI:2739366 (SEQ ID NO: 202), GI:297825811 (SEQ ID NO: 203), CeresClone:375578m1 (SEQ ID NO: 205), CeresClone: 375578m2 (SEQ ID NO: 206), or GI:307135879 (SEQ ID NO: 207). In some cases, a functional homolog of SEQ ID NO: 111 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 111. In some cases, a functional homolog of SEQ TD NO: 111 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 111 described above or set forth in the Sequence Listing.

The polypeptide set forth in SEQ ID NO: 111, or the functional homologs set forth above or in the Sequence Listing, can be truncated at the N- or C-terminus or both. In one embodiment, a functional homolog of SEQ ID NO:111 contains an C-terminal truncation. For example, a functional homolog of SEQ ID NO: 111 can include a sequence of amino acids with significant sequence identity to the region corresponding approximately to residues 1 to 135 of SEQ ID NO: 111, such as SEQ ID NO:205.

Examples of amino acid sequences of functional homologs of the polypeptide set forth in SEQ ID NO: 27 are provided in FIG. 5 and in the Sequence Listing. Such functional homologs include, for example, CeresClone: 1925947 (SEQ ID NO: 29), CeresAnnot:1514501 (SEQ ID NO: 31), CeresAnnot:849672 (SEQ ID NO: 33), GI:157355942 (SEQ ID NO: 34), GI:115452503 (SEQ ID NO: 35), CeresClone:1790933 (SEQ ID NO: 37), CeresAnnot:8641620 (SEQ ID NO: 39), CeresClone:281497 (SEQ ID NO: 41), GI:168013851 (SEQ ID NO: 42), CeresClone: 143214 (SEQ ID NO: 44), CeresClone:1781022 (SEQ ID NO: 46), CeresClone:618639 (SEQ ID NO: 48), GI:118483001 (SEQ ID NO: 49), CeresClone:38404 (SEQ ID NO: 51), GI:3549670 (SEQ ID NO: 52), GI:37703720 (SEQ ID NO: 53), GI:24414269 (SEQ ID NO: 54), GI:125603687 (SEQ ID NO: 55), GI:108707679 (SEQ ID NO: 56), GI:157352390 (SEQ ID NO: 57), GI:159469820 (SEQ ID NO: 58), or GI:145344081 (SEQ ID NO: 59). In some cases, a functional homolog of SEQ ID NO: 27 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 27. In some cases, a functional homolog of SEQ ID NO: 27 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 27 described above or set forth in the Sequence Listing.

Examples of amino acid sequences of functional homologs of the polypeptide set forth in SEQ ID NO: 209 are provided in FIG. 6 and in the Sequence Listing. Such functional homologs include, for example, CeresAnnot: 1472338_Pb (SEQ ID NO: 211), GI:157344683_Vv (SEQ ID NO: 212), GI:87240677_Mt (SEQ ID NO: 213), GI:115448297_Os (SEQ ID NO: 214), CeresClone: 1844568_Pv (SEQ ID NO: 216), CeresClone:797829_Tm (SEQ ID NO: 218), GI:168033816_Pp (SEQ ID NO: 219), GI:116788004_Ps (SEQ ID NO: 220), GI:149900503_Ha (SEQ ID NO: 221), GI:4102839_Sl (SEQ ID NO: 222), GI:31088360_Vf (SEQ ID NO: 223), CeresAnnot: 8681236_Sb (SEQ ID NO: 225), CeresAnnot:8519531_Gm (SEQ ID NO: 227), CeresAnnot:8631372_Zm (SEQ ID NO: 229), GI:151426449_Hv (SEQ ID NO: 230), GI:192757675_Br (SEQ ID NO: 231), GI:2655098 (SEQ ID NO: 232), GI:194690746 (SEQ ID NO: 233), CeresClone: 752925 (SEQ ID NO: 235), GI:125540898 (SEQ ID NO: 236), GI:26451333 (SEQ ID NO: 237), GI:2160144 (SEQ ID NO: 238), GI:30696666 (SEQ ID NO: 239), GI:125556922 (SEQ ID NO: 240), CeresAnnot:1529287 (SEQ ID NO: 242), CeresClone:1806748 (SEQ ID NO: 244), CeresAnnot:8755095 (SEQ ID NO: 246), GI:147827175 (SEQ ID NO: 247), CeresClone:1888865 (SEQ ID NO: 249), GI:157337163 (SEQ ID NO: 250), GI:115434472 (SEQ ID NO: 251), CeresAnnot:6252512 (SEQ ID NO: 253), CeresAnnot:1569074_Mt (SEQ ID NO: 255), CeresAnnot:1475845 (SEQ ID NO: 257), CeresAnnot: 1501483 (SEQ ID NO: 259), CeresAnnot:8755079 (SEQ ID NO: 261), GI:115470147 (SEQ ID NO: 262), GI:15240905 (SEQ ID NO: 263), CeresAnnot:8755085 (SEQ ID NO: 265), GI:147853446 (SEQ ID NO: 266), GI:157346087 (SEQ ID NO: 267), CeresAnnot:1538867 (SEQ ID NO: 269), CeresAnnot:8755091 (SEQ ID NO: 271), CeresAnnot: 1492702 (SEQ ID NO: 273), CeresClone:325604 (SEQ ID NO: 275), GI:108707040 (SEQ ID NO: 276), CeresAnnot: 1302517 At (SEQ ID NO: 278), CeresAnnot:1355964 (SEQ ID NO: 280), CeresAnnot:8755104 (SEQ ID NO: 282), GI:147802380 (SEQ ID NO: 283), GI:510238 (SEQ ID NO: 284), GI:157341962 (SEQ ID NO: 285), GI:6635838 (SEQ ID NO: 286), GI:4455276 (SEQ ID NO: 287), CeresAnnot: 8642246 (SEQ ID NO: 289), CeresAnnot:8633032 (SEQ ID NO: 291), GI:157337654 (SEQ ID NO: 292), CeresAnnot: 8642241 (SEQ ID NO: 294), CeresAnnot:1520085 (SEQ ID NO: 296), CeresAnnot:1514979 (SEQ ID NO: 298), GI:147858202 (SEQ ID NO: 299), GI:125545538 (SEQ ID NO: 300), GI:115451771 (SEQ ID NO: 301), GI:125587732 (SEQ ID NO: 302), CeresAnnot:1516968 (SEQ ID NO: 304), CeresClone:350844 (SEQ ID NO: 306), CeresAnnot: 8658700 (SEQ ID NO: 308), GI:157346088 (SEQ ID NO: 309), CeresClone:1926916 (SEQ ID NO: 311), GI:15226861 (SEQ ID NO: 312), CeresClone:816960 (SEQ ID NO: 314), GI:15232435 (SEQ ID NO: 315), CeresAnnot: 8643789 (SEQ ID NO: 317), CeresAnnot:8631367 (SEQ ID NO: 319), GI:157339093 (SEQ ID NO: 320), CeresAnnot: 8633031 (SEQ ID NO: 322), GI:125543029 (SEQ ID NO: 323), GI:115454995 (SEQ ID NO: 324), CeresAnnot: 8755090 (SEQ ID NO: 326), CeresAnnot:8755097 (SEQ ID NO: 328), CeresAnnot:8755098 (SEQ ID NO: 330), CeresAnnot:8755099 (SEQ ID NO: 332), WO2008034648-158133 (SEQ ID NO: 333), WO2008034648-158187 (SEQ ID NO: 334), or US7390893-0003 (SEQ ID NO: 335). In some cases, a functional homolog of SEQ ID NO: 209 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 209. In some cases, a functional homolog of SEQ ID NO: 209 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 209 described above or set forth in the Sequence Listing.

Examples of amino acid sequences of functional homologs of the polypeptide set forth in SEQ ID NO: 370 are provided in FIG. 7 and in the Sequence Listing. Such functional homologs include, for example, CeresClone: 645403 (SEQ ID NO: 372), CeresAnnot:8717693 (SEQ ID NO: 374), GI:212721672 (SEQ ID NO: 375), GI:115487934 (SEQ ID NO: 376), GI:357160384 (SEQ ID NO: 377), GI:208431904 (SEQ ID NO: 378), GI:326531522 (SEQ ID NO: 379), CeresClone:1910316 (SEQ ID NO: 381), GI:27469354 (SEQ ID NO: 382), GI:125536186 (SEQ ID NO: 383), GI:255555917 (SEQ ID NO: 384), GI:224074359 (SEQ ID NO: 385), GI:147845138 (SEQ ID NO: 386), GI:224139026 (SEQ ID NO: 387), GI:225427091 (SEQ ID NO: 388), CeresAnnot:1538994 (SEQ ID NO: 390), GI:356531457 (SEQ ID NO: 391), GI:13775109 (SEQ ID NO: 392), CeresAnnot:1447080 (SEQ ID NO: 394), GI:356496180 (SEQ ID NO: 395), GI:5381313 (SEQ ID NO: 396), GI:3336906 (SEQ ID NO: 397), CeresClone: 1611686 (SEQ ID NO: 399), CeresClone:1927515 (SEQ ID NO: 401), and CeresAnnot:834509 (SEQ ID NO: 403). In some cases, a functional homolog of SEQ ID NO: 370 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 370. In some cases, a functional homolog of SEQ ID NO: 370 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 370 described above or set forth in the Sequence Listing.

The identification of conserved regions in an abiotic stress tolerance-increasing polypeptide facilitates production of variants of abiotic stress tolerance-increasing polypeptides. Variants of abiotic stress tolerance-increasing polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in FIG. 1, FIG. 2, FIG. 3, or FIG. 4, FIG. 5, FIG. 6, or FIG. 7 and/or homologs identified in the Sequence Listing. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at a position marked by dashes, such a polypeptide has a length that is the sum of the amino acid residues in all conserved regions and all dashes.

C. Functional Homologs Identified by HMMER

In some embodiments, useful abiotic stress tolerance-increasing polypeptides include those that fit a Hidden Markov Model based on the polypeptides set forth in any one of FIGS. 1-7. A Hidden Markov Model (HMM) is a statistical model of a consensus sequence for a group of functional homologs. See, Durbin et al., *Biological Sequence Analysis: Probabilistic Models of Proteins and Nucleic Acids*, Cambridge University Press, Cambridge, UK (1998). An HMM is generated by the program HMMer 3.0 with default program parameters, using the sequences of the group of functional homologs as input. In some instances, the input files can be in FASTA format. HMMer is provided by the Howard Hughes Medical Institute (hmmer.janelia.org).

The multiple sequence alignment is generated by ProbCons (Do et al., *Genome Res.*, 15(2):330-40 (2005)) version 1.12 using default parameters: ProbCons is a public domain software program. ProbCons and HMMer can be found on the world wide web at fr.com/probcons/.

The HMM for a group of functional homologs can be used to determine the likelihood that a candidate abiotic stress tolerance-increasing polypeptide sequence is a better fit to that particular HMM than to a null HMM generated using a group of sequences that are not structurally or functionally related. The likelihood that a candidate polypeptide sequence is a better fit to an HMM than to a null HMM is indicated by the HMM bit score, a number generated when the candidate sequence is fitted to the HMM profile using the HMMer hmmsearch program. The following parameter is used when running hmmsearch: the E-value cutoff for reporting is set to 1 ("-E 1"). A high HMM bit score indicates a greater likelihood that the candidate sequence carries out one or more of the biochemical or physiological function(s) of the polypeptides used to generate the HMM. A high HMM bit score is at least 20, and often is higher. Slight variations in the HMM bit score of a particular sequence can occur due to factors such as the order in which sequences are processed for alignment by multiple sequence alignment algorithms such as the ProbCons program. Nevertheless, such HMM bit score variation is minor.

The abiotic stress tolerance-increasing polypeptides discussed below fit the indicated HMM with an HMM bit score greater than to 65 (e.g., greater than 70, 80, 90, 100, 120, 140, 200, 300, 400, 500, 600, 700, 800, 900, 1000, 1500, or 2000). In some embodiments, the HMM bit score of an abiotic stress tolerance-increasing polypeptide discussed below is about 50%, 60%, 70%, 80%, 90%, or 95% of the HMM bit score of a functional homolog provided in the Sequence Listing of this application. In some embodiments, an abiotic stress tolerance-increasing polypeptide discussed below fits the indicated HMM with an HMM bit score greater than 210, and has a domain indicative of an abiotic stress tolerance-increasing polypeptide. In some embodiments, an abiotic stress tolerance-increasing polypeptide discussed below fits the indicated HMM with an HMM bit score greater than 210, and has 65% or greater sequence identity (e.g., 75%, 80%, 85%, 90%, 95%, or 100% sequence identity) to an amino acid sequence shown in any one of FIGS. 1-7.

Examples of polypeptides are shown in the sequence listing that have HMM bit scores greater than 260 (e.g., greater than 265, 270, 275, 280, 285, 290, 295, 300, 305, 310, 315, 320, 325, 330, 335, 340, or 342) when fitted to an HMM generated from the amino acid sequences set forth in FIG. 1 are identified in the Sequence Listing of this application. Such polypeptides include, for example, SEQ ID NOs: 2, 4, 6, 8, 9, 10, 11, 13, 15, 16, 17, 18, 20, 21, 22, 24, or 25.

Examples of polypeptides are shown in the sequence listing that have HMM bit scores greater than 730 (e.g., greater than 750, 775, 800, 825, 850, 875, 900, 925, 950, 975, 1000, 1025, 1050, 1075, 1100, 1125, 1150, 1175, 1200, 1210, or 1215) when fitted to an HMM generated from the amino acid sequences set forth in FIG. 2 are identified in the Sequence Listing of this application. Such polypeptides include, for example, SEQ ID NOs: 337, 338, 339, 340, 341, 342, 344, 345, 347, 348, 350, 352, 353, 354, 355, 356, 357, 358, 359, 360, 362, 364, 365, 366, 367, or 368.

Examples of polypeptides are shown in the sequence listing that have HMM bit scores greater than 350 (e.g., greater than 355, 360, 365, 370, 375, 380, 385, 390, 395, 400, 405, 410, 415, 420, 425, 430, 435, 440, 445, or 450) when fitted to an HMM generated from the amino acid sequences set forth in FIG. 3 are identified in the Sequence Listing of this application. Such polypeptides include, for example, SEQ ID NOs: 61, 63, 64, 66, 68, 69, 70, 71, 72, 74, 75, 76, 77, 79, 81, 82, 84, 85, 86, 88, 89, 91, 93, 95, 96, 98, 99, 100, 102, 103, 104, 105, 107, 108, or 109.

Examples of polypeptides are shown in the sequence listing that have HMM bit scores greater than 240 (e.g., greater than 250, 275, 300, 325, 350, 375, 400, 425, 450, 475, 500, 525, 550, 575, 600, 625, 650, 675, 700, 725, 750, 775, 800, 825, 840, or 850) when fitted to an HMM generated from the amino acid sequences set forth in FIG. 4 are identified in the Sequence Listing of this application. Such polypeptides include, for example, SEQ ID NOs: 111, 113, 115, 116, 117, 118, 120, 122, 123, 124, 126, 128, 130, 131, 133, 135, 137, 138, 139, 140, 141, 142, 143, 144, 145, 146, 147, 149, 151, 153, 154, 155, 156, 157, 158, 159, 160, 162, 163, 165, 167, 169, 171, 172, 174, 176, 178, 179, 181, 182, 183, 184, 186, 187, 189, 190, 191, 192, 193, 194, 195, 196, 197, 198, 199, 200, 201, 202, 203, 205, 206, or 207.

Examples of polypeptides are shown in the sequence listing that have HMM bit scores greater than 610 (e.g., greater than 625, 650, 675, 700, 725, 750, 775, 800, 825, 850, 875, 900, 925, 950, 975, or 980) when fitted to an HMM generated from the amino acid sequences set forth in FIG. 5 are identified in the Sequence Listing of this application. Such polypeptides include, for example, SEQ ID NOs: 27, 29, 31, 33, 34, 35, 37, 39, 41, 42, 44, 46, 48, 49, 51, 52, 53, 54, 55, 56, 57, 58, or 59.

Examples of polypeptides are shown in the sequence listing that have HMM bit scores greater than 520 (e.g., greater than 550, 575, 600, 625, 650, 675, 700, 725, 750, 775, 800, 825, 850, 875, 900, 925, 950, 975, 1000, 1025, or 1040) when fitted to an HMM generated from the amino acid sequences set forth in FIG. 6 are identified in the Sequence Listing of this application. Such polypeptides include, for example, SEQ ID NOs: 209, 211, 212, 213, 214, 216, 218, 219, 220, 221, 222, 223, 225, 227, 229, 230, 231, 232, 233, 235, 236, 237, 238, 239, 240, 242, 244, 246, 247, 249, 250, 251, 253, 255, 257, 259, 261, 262, 263, 265, 266, 267, 269, 271, 273, 275, 276, 278, 280, 282, 283, 284, 285, 286, 287, 289, 291, 292, 294, 296, 298, 299, 300, 301, 302, 304, 306, 308, 309, 311, 312, 314, 315, 317, 319, 320, 322, 323, 324, 326, 328, 330, 332, 333, 334, or 335.

Examples of polypeptides are shown in the sequence listing that have HMM bit scores greater than 525 (e.g., greater than 550, 575, 600, 625, 650, 675, 700, 725, or 750) when fitted to an HMM generated from the amino acid sequences set forth in FIG. 7 are identified in the Sequence Listing of this application. Such polypeptides include, for example, SEQ ID NOs: 370, 372, 374, 375, 376, 377, 378, 379, 381, 382, 383, 384, 385, 386, 387, 388, 390, 391, 392, 394, 395, 396, 397, 399, 401, and 403.

D. Percent Identity

In some embodiments, an abiotic stress tolerance-increasing polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one of the amino acid sequences set forth in SEQ ID NOs: 2, 4, 6, 8, 9, 10, 11, 13, 15, 16, 17, 18, 20, 21, 22, 24, 25, 27, 29, 31, 33, 34, 35, 37, 39, 41, 42, 44, 46, 48, 49, 51, 52, 53, 54, 55, 56, 57, 58, 59, 61, 63, 64, 66, 68, 69, 70, 71, 72, 74, 75, 76, 77, 79, 81, 82, 84, 85, 86, 88, 89, 91, 93, 95, 96, 98, 99, 100, 102, 103, 104, 105, 107, 108, 109, 111, 113, 115, 116, 117, 118, 120, 122, 123, 124, 126, 128, 130, 131, 133, 135, 137, 138, 139, 140, 141, 142, 143, 144, 145, 146, 147, 149, 151, 153, 154, 155, 156, 157, 158, 159, 160, 162, 163, 165, 167, 169, 171, 172, 174, 176, 178, 179, 181, 182, 183, 184, 186, 187, 189, 190, 191, 192, 193, 194, 195, 196, 197, 198, 199, 200, 201, 202, 203, 205, 206, 207, 209, 211, 212, 213, 214, 216, 218, 219, 220, 221, 222, 223, 225, 227, 229, 230, 231, 232, 233, 235, 236, 237, 238, 239, 240, 242, 244, 246, 247, 249, 250, 251, 253, 255, 257, 259, 261, 262, 263, 265, 266, 267, 269, 271, 273, 275, 276, 278, 280, 282, 283, 284, 285, 286, 287, 289, 291, 292, 294, 296, 298, 299, 300, 301, 302, 304, 306, 308, 309, 311, 312, 314, 315, 317, 319, 320, 322, 323, 324, 326, 328, 330, 332, 333, 334, 335, 337, 338, 339, 340, 341, 342, 344, 345, 347, 348, 350, 352, 353, 354, 355, 356, 357, 358, 359, 360, 362, 364, 365, 366, 367, 368, 370, 372, 374, 375, 376, 377, 378, 379, 381, 382, 383, 384, 385, 386, 387, 388, 390, 391, 392, 394, 395, 396, 397, 399, 401, or 403. Polypeptides having such a percent sequence identity often have a domain indicative of an abiotic stress tolerance-increasing polypeptide and/or have an HMM bit score that is greater than 65, as discussed above. Amino acid sequences of abiotic stress tolerance-increasing polypeptides having at least 80% sequence identity to one of the amino acid sequences set forth in SEQ ID NOs: 2, 4, 6, 8, 9, 10, 11, 13, 15, 16, 17, 18, 20, 21, 22, 24, 25, 27, 29, 31, 33, 34, 35, 37, 39, 41, 42, 44, 46, 48, 49, 51, 52, 53, 54, 55, 56, 57, 58, 59, 61, 63, 64, 66, 68, 69, 70, 71, 72, 74, 75, 76, 77, 79, 81, 82, 84, 85, 86, 88, 89, 91, 93, 95, 96, 98, 99, 100, 102, 103, 104, 105, 107, 108, 109, 111, 113, 115, 116, 117, 118, 120, 122, 123, 124, 126, 128, 130, 131, 133, 135, 137, 138, 139, 140, 141, 142, 143, 144, 145, 146, 147, 149, 151, 153, 154, 155, 156, 157, 158, 159, 160, 162, 163, 165, 167, 169, 171, 172, 174, 176, 178, 179, 181, 182, 183, 184, 186, 187, 189, 190, 191, 192, 193, 194, 195, 196, 197, 198, 199, 200, 201, 202, 203, 205, 206, 207, 209, 211, 212, 213, 214, 216, 218, 219, 220, 221, 222, 223, 225, 227, 229, 230, 231, 232, 233, 235, 236, 237, 238, 239, 240, 242, 244, 246, 247, 249, 250, 251, 253, 255, 257, 259, 261, 262, 263, 265, 266, 267, 269, 271, 273, 275, 276, 278, 280, 282, 283, 284, 285, 286, 287, 289, 291, 292, 294, 296, 298, 299, 300, 301, 302, 304, 306, 308, 309, 311, 312, 314, 315, 317, 319, 320, 322, 323, 324, 326, 328, 330, 332, 333, 334, 335, 337, 338, 339, 340, 341, 342, 344, 345, 347, 348, 350, 352, 353, 354, 355, 356, 357, 358, 359, 360, 362, 364, 365, 366, 367, 368, 370, 372, 374, 375, 376, 377, 378, 379, 381, 382, 383, 384, 385, 386, 387, 388, 390, 391, 392, 394, 395, 396, 397, 399, 401, and 403 are provided in FIGS. 1-7 and in the Sequence Listing.

"Percent sequence identity" refers to the degree of sequence identity between any given reference sequence, e.g., SEQ ID NO: 2, and a candidate abiotic stress tolerance-increasing sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., *Nucleic Acids Res.*, 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, an abiotic stress tolerance-increasing polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2. Amino acid sequences of polypeptides having greater than 45% sequence identity to the polypeptide set forth in SEQ ID NO: 2 are provided in FIG. 1 and in the Sequence Listing.

In some cases, an abiotic stress tolerance-increasing polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 337 Amino acid sequences of polypeptides having greater than 45% sequence identity to the polypeptide set forth in SEQ ID NO: 337 are provided in FIG. 2 and in the Sequence Listing.

In some cases, an abiotic stress tolerance-increasing polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 61. Amino acid sequences of polypeptides having greater than 45% sequence identity to the polypeptide set forth in SEQ ID NO: 61 are provided in FIG. 3 and in the Sequence Listing.

In some cases, an abiotic stress tolerance-increasing polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:111. Amino acid sequences of polypeptides having greater than 45% sequence identity to the polypeptide set forth in SEQ ID NO: 111 are provided in FIG. 4 and in the Sequence Listing.

In some cases, an abiotic stress tolerance-increasing polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 27. Amino acid sequences of polypeptides having greater than 45% sequence identity to the polypeptide set forth in SEQ ID NO: 27 are provided in FIG. 5 and in the Sequence Listing.

In some cases, an abiotic stress tolerance-increasing polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 209 Amino acid sequences of polypeptides having greater than 45% sequence identity to the polypeptide set forth in SEQ ID NO: 209 are provided in FIG. 6 and in the Sequence Listing.

In some cases, an abiotic stress tolerance-increasing polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 370 Amino acid sequences of polypeptides having greater than 45% sequence identity to the polypeptide set forth in SEQ ID NO: 370 are provided in FIG. 7 and in the Sequence Listing.

E. Other Sequences

It should be appreciated that an abiotic stress tolerance-increasing polypeptide can include additional amino acids that are not involved in abiotic stress tolerance modulation, and thus such a polypeptide can be longer than would otherwise be the case. For example, an abiotic stress tolerance-increasing polypeptide can include a purification tag, a chloroplast transit peptide, a mitochondrial transit peptide, an amyloplast peptide, or a leader sequence added to the amino or carboxy terminus. In some embodiments, an abiotic stress tolerance-increasing polypeptide includes an amino acid sequence that functions as a reporter, e.g., a green fluorescent protein or yellow fluorescent protein.

III. Nucleic Acids

Nucleic acids described herein include nucleic acids that are effective to increase abiotic stress tolerance levels when transcribed in a plant or plant cell. Such nucleic acids include, without limitation, those that encode an abiotic stress tolerance-increasing polypeptide and those that can be used to inhibit expression of an abiotic stress tolerance-increasing polypeptide via a nucleic acid based method.

A. Nucleic Acids Encoding Abiotic Stress Tolerance-Increasing Polypeptides

Nucleic acids encoding abiotic stress tolerance-increasing polypeptides are described herein. Examples of such nucleic acids include SEQ ID NOs: 1, 3, 5, 7, 12, 14, 19, 23, 26, 28, 30, 32, 36, 38, 40, 43, 45, 47, 50, 60, 62, 65, 67, 73, 78, 80, 83, 87, 90, 92, 94, 97, 101, 106, 110, 112, 114, 119, 121, 125, 127, 129, 132, 134, 136, 148, 150, 152, 161, 164, 166, 168, 170, 173, 175, 177, 180, 185, 188, 204, 208, 210, 215, 217, 224, 226, 228, 234, 241, 243, 245, 248, 252, 254, 256, 258, 260, 264, 268, 270, 272, 274, 277, 279, 281, 288, 290, 293, 295, 297, 303, 305, 307, 310, 313, 316, 318, 321, 325, 327, 329, 331, 336, 343, 346, 349, 351, 361, 363, 369, 371, 373, 380, 389, 393, 398, 400, and 402 as described in more detail below. A nucleic acid also can be a fragment that is at least 40% (e.g., at least 45, 50, 55, 60, 65, 70, 75, 80, 85, 90, 95, or 99%) of the length of the full-length nucleic acid set forth in SEQ ID NOs: 1, 3, 5, 7, 12, 14, 19, 23, 26, 28, 30, 32, 36, 38, 40, 43, 45, 47, 50, 60, 62, 65, 67, 73, 78, 80, 83, 87, 90, 92, 94, 97, 101, 106, 110, 112, 114, 119, 121, 125, 127, 129, 132, 134, 136, 148, 150, 152, 161, 164, 166, 168, 170, 173, 175, 177, 180, 185, 188, 204, 208, 210, 215, 217, 224, 226, 228, 234, 241, 243, 245, 248, 252, 254, 256, 258, 260, 264, 268, 270, 272, 274, 277, 279, 281, 288, 290, 293, 295, 297, 303, 305, 307, 310, 313, 316, 318, 321, 325, 327, 329, 331, 336, 343, 346, 349, 351, 361, 363, 369, 371, 373, 380, 389, 393, 398, 400, and 402.

An abiotic stress tolerance-increasing nucleic acid can comprise the nucleotide sequence set forth in SEQ ID NO:1. Alternatively, an abiotic stress tolerance-increasing nucleic acid can be a variant of the nucleic acid having the nucleotide sequence set forth in SEQ ID NO: 1. For example, an abiotic stress tolerance-increasing nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1.

An abiotic stress tolerance-increasing nucleic acid can comprise the nucleotide sequence set forth in SEQ ID NO:336. Alternatively, an abiotic stress tolerance-increasing nucleic acid can be a variant of the nucleic acid having the nucleotide sequence set forth in SEQ ID NO: 336. For example, an abiotic stress tolerance-increasing nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 336.

An abiotic stress tolerance-increasing nucleic acid can comprise the nucleotide sequence set forth in SEQ ID NO:60. Alternatively, an abiotic stress tolerance-increasing nucleic acid can be a variant of the nucleic acid having the nucleotide sequence set forth in SEQ ID NO: 60. For example, an abiotic stress tolerance-increasing nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 60.

An abiotic stress tolerance-increasing nucleic acid can comprise the nucleotide sequence set forth in SEQ ID NO:110. Alternatively, an abiotic stress tolerance-increasing nucleic acid can be a variant of the nucleic acid having the nucleotide sequence set forth in SEQ ID NO: 110. For example, an abiotic stress tolerance-increasing nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 110.

An abiotic stress tolerance-increasing nucleic acid can comprise the nucleotide sequence set forth in SEQ ID NO:26. Alternatively, an abiotic stress tolerance-increasing nucleic acid can be a variant of the nucleic acid having the nucleotide sequence set forth in SEQ ID NO: 26. For example, an abiotic stress tolerance-increasing nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 26.

An abiotic stress tolerance-increasing nucleic acid can comprise the nucleotide sequence set forth in SEQ ID NO:208. Alternatively, an abiotic stress tolerance-increasing nucleic acid can be a variant of the nucleic acid having the nucleotide sequence set forth in SEQ ID NO: 208. For example, an abiotic stress tolerance-increasing nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 208.

An abiotic stress tolerance-increasing nucleic acid can comprise the nucleotide sequence set forth in SEQ ID NO:369. Alternatively, an abiotic stress tolerance-increasing nucleic acid can be a variant of the nucleic acid having the nucleotide sequence set forth in SEQ ID NO: 369. For example, an abiotic stress tolerance-increasing nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 369.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from a DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

B. Use of Nucleic Acids to Modulate Expression of Polypeptides i. Expression of an Abiotic Stress Tolerance-Increasing Polypeptide A nucleic acid encoding one of the abiotic stress tolerance-increasing polypeptides described herein can be used to express the polypeptide in a plant species of interest, typically by transforming a plant cell with a nucleic acid having the coding sequence for the polypeptide operably linked in sense orientation to one or more regulatory regions. It will be appreciated that because of the degeneracy of the genetic code, a number of nucleic acids can encode a particular abiotic stress tolerance-increasing polypeptide; i.e., for many amino acids, there is more than one nucleotide triplet that serves as the codon for the amino acid. Thus, codons in the coding sequence for a given abiotic stress tolerance-increasing polypeptide can be modified such that optimal expression in a particular plant species is obtained, using appropriate codon bias tables for that species.

In some cases, expression of an abiotic stress tolerance-increasing polypeptide inhibits one or more functions of an endogenous polypeptide. For example, a nucleic acid that encodes a dominant negative polypeptide can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation.

ii. Inhibition of Expression of an Abiotic Stress Tolerance-Increasing Polypeptide Polynucleotides and recombinant constructs described herein can be used to inhibit expression of an abiotic stress tolerance-increasing polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); and *Nature Reviews RNA interference collection*, October 2005 on the World Wide Web at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Suitable polynucleotides include full-length nucleic acids encoding abiotic stress tolerance-increasing polypeptides or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid of a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid need not be the entire sequence of the gene to be repressed, but typically will be substantially complementary to at least a portion of the sense strand of the gene to be repressed.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci.*

*USA*, 92(13):6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof of an abiotic stress tolerance-increasing polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand or a fragment thereof of the coding sequence of the abiotic stress tolerance-increasing polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of an mRNA encoding an abiotic stress tolerance-increasing polypeptide, and the other strand of the stem portion of the double stranded RNA comprises a sequence that is similar or identical to the sequence that is complementary to the 3' or 5' untranslated region, respectively, or a fragment thereof, of the mRNA encoding the abiotic stress tolerance-increasing polypeptide. In other embodiments, one strand of the stem portion of a double stranded RNA comprises a sequence that is similar or identical to the sequence of an intron, or a fragment thereof, in the pre-mRNA encoding an abiotic stress tolerance-increasing polypeptide, and the other strand of the stem portion comprises a sequence that is similar or identical to the sequence that is complementary to the sequence of the intron, or a fragment thereof, in the pre-mRNA.

The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron or a fragment thereof. A double stranded RNA can have zero, one, two, three, four, five, six, seven, eight, nine, ten, or more stem-loop structures.

A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence, or a fragment thereof, of an abiotic stress tolerance-increasing polypeptide. The transcription product also can be unpolyadenylated, lack a 5' cap structure, or contain an unspliceable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding an abiotic stress tolerance-increasing polypeptide, or a fragment of such sequences. In some embodiments, the sense or antisense sequence is identical or complementary to a sequence of the regulatory region that drives transcription of the gene encoding an abiotic stress tolerance-increasing polypeptide. In each case, the sense sequence is the sequence that is complementary to the antisense sequence.

The sense and antisense sequences can be a length greater than about 10 nucleotides (e.g., 12, 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence, or a fragment thereof, encoding an abiotic stress tolerance-increasing polypeptide described herein. The sense sequence complementary to the antisense sequence can be a sequence present within the mRNA of the abiotic stress tolerance-increasing polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have a suitable arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences or the left and right border-like sequences of the P-DNA flank, or are on either side of, the nucleic acid. See, U.S. Patent Publication No. 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, *Antisense Nucleic Acid Drug Dev.*, 7:187-195 (1997); Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

C. Constructs/Vectors

Recombinant constructs provided herein can be used to transform plants or plant cells in order to modulate abiotic stress tolerance levels. A recombinant nucleic acid construct can comprise a nucleic acid encoding an abiotic stress tolerance-increasing polypeptide as described herein, operably linked to a regulatory region suitable for expressing the abiotic stress tolerance-increasing polypeptide in the plant or cell. Thus, a nucleic acid can comprise a coding sequence that encodes an abiotic stress tolerance-increasing polypeptide as set forth in SEQ ID NOs: 2, 4, 6, 8, 9, 10, 11, 13, 15, 16, 17, 18, 20, 21, 22, 24, 25, 27, 29, 31, 33, 34, 35, 37, 39, 41, 42, 44, 46, 48, 49, 51, 52, 53, 54, 55, 56, 57, 58, 59, 61, 63, 64, 66, 68, 69, 70, 71, 72, 74, 75, 76, 77, 79, 81, 82, 84, 85, 86, 88, 89, 91, 93, 95, 96, 98, 99, 100, 102, 103, 104, 105, 107, 108, 109, 111, 113, 115, 116, 117, 118, 120, 122, 123, 124, 126, 128, 130, 131, 133, 135, 137, 138, 139, 140, 141, 142, 143, 144, 145, 146, 147, 149, 151, 153, 154, 155, 156, 157, 158, 159, 160, 162, 163, 165, 167, 169, 171, 172, 174, 176, 178, 179, 181, 182, 183, 184, 186, 187, 189, 190, 191, 192, 193, 194, 195, 196, 197, 198, 199, 200, 201, 202, 203, 205, 206, 207, 209, 211, 212, 213, 214, 216, 218, 219, 220, 221, 222, 223, 225, 227, 229, 230, 231, 232, 233, 235, 236, 237, 238, 239, 240, 242, 244, 246, 247, 249, 250, 251, 253, 255, 257, 259, 261, 262, 263, 265, 266, 267, 269, 271, 273, 275, 276, 278, 280, 282, 283, 284, 285, 286, 287, 289, 291, 292, 294, 296, 298, 299, 300, 301, 302, 304, 306, 308, 309, 311, 312, 314, 315, 317, 319, 320, 322, 323, 324, 326, 328, 330, 332, 333, 334, 335, 337, 338, 339, 340, 341, 342, 344, 345, 347, 348, 350, 352, 353, 354, 355, 356, 357, 358, 359, 360, 362, 364, 365, 366, 367, 368, 370, 372, 374, 375, 376, 377, 378, 379, 381, 382, 383, 384, 385, 386, 387, 388, 390, 391, 392, 394, 395, 396, 397, 399, 401, or 403. Examples of nucleic acids encoding abiotic stress tolerance-increasing polypeptides are set forth in SEQ ID NOs: 1, 3, 5, 7, 12, 14, 19, 23, 26, 28, 30, 32, 36, 38, 40, 43, 45, 47, 50, 60, 62, 65, 67, 73, 78, 80, 83, 87, 90, 92, 94, 97, 101, 106, 110, 112, 114, 119, 121, 125, 127, 129, 132, 134, 136, 148, 150, 152, 161, 164, 166, 168, 170, 173, 175, 177, 180, 185, 188, 204, 208, 210, 215, 217, 224, 226, 228, 234, 241, 243, 245, 248, 252, 254, 256, 258, 260, 264, 268, 270, 272, 274, 277, 279, 281, 288, 290, 293, 295, 297, 303, 305, 307, 310, 313, 316, 318, 321, 325, 327, 329, 331, 336, 343, 346, 349, 351, 361, 363, 369, 371, 373, 380, 389, 393, 398, 400, and 402, or in the Sequence Listing. The abiotic stress tolerance-increasing polypeptide encoded by a recombinant nucleic acid can be a native abiotic stress tolerance-increasing polypeptide, or can be heterologous to the cell. In some cases, the recombinant construct contains a nucleic acid that inhibits expression of an abiotic stress tolerance-increasing polypeptide, operably linked to a regulatory region. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen® (Madison, Wis.), Clontech® (Palo Alto, Calif.), Stratagene® (La Jolla, Calif.), and Invitrogen/Life Technologies® (Carlsbad, Calif.).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, β-glucuronidase (GUS), green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

D. Regulatory Regions

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable regulatory regions initiate transcription only, or predominantly, in certain cell types. Methods for identifying and characterizing regulatory regions in plant genomic DNA are known, including, for example, those described in the following references: Jordano et al., *Plant Cell*, 1:855-866 (1989); Bustos et al., *Plant Cell*, 1:839-854 (1989); Green et al., *EMBO J.*, 7:4035-4044 (1988); Meier et al., *Plant Cell*, 3:309-316 (1991); and Zhang et al., *Plant Physiology*, 110:1069-1079 (1996).

Examples of various classes of regulatory regions are described below. Some of the regulatory regions indicated below as well as additional regulatory regions are described in more detail in U.S. Patent Application Ser. Nos. 60/505,689; 60/518,075; 60/544,771; 60/558,869; 60/583,691; 60/619,181; 60/637,140; 60/757,544; 60/776,307; 10/957,569; 11/058,689; 11/172,703; 11/208,308; 11/274,890; 60/583,609; 60/612,891; 11/097,589; 11/233,726; 11/408,791; 11/414,142; 10/950,321; 11/360,017; PCT/US05/011105; PCT/US05/23639; PCT/US05/034308; PCT/US05/034343; and PCT/US06/038236; PCT/US06/040572; PCT/US07/62762; PCT/US2009/032485; and PCT/US2009/038792.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

i. Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

Another example of a broad promoter is the sequence of regulatory region PD3141 set forth in the sequence listing of PCT/US2009/032485. Therein, the expression pattern of the PD3141 regulatory region is described for T0 rice plants overexpressing a construct comprising PD3141 driving expression of EGFP. In seedlings, expression was observed in: Tiller: not-specific; Main culm: not-specific; Root: not-specific; Leaf: not-specific; and Meristem: not-specific. In mature plants, expression was observed in: Main culm: bundle sheath, endodermis, epidermis, internode, ligule, node, pericycle, phloem, sclerenchyma layer, vasculature, xylem; Root: cortex, vascular; Panicle: flag leaf, ovary, peduncle, primary branch, rachilla, rachis, spiklet; Spiklet: flag leaf, floret(palea), lemma, ovule, pedicle, pollen, seed, stigma; Leaf: epidermis, leaf blade, leaf sheath, mesophyll; and Meristem: floral meristem, shoot apical meristem, vegetative meristem.

Another example of a broad promoter is the sequence of regulatory region p326 set forth in the sequence listing of U.S. application Ser. No. 10/981,334. Therein, the expression pattern of the p326 regulatory region is described for *Arabidopsis* plants. p326 expressed throughout most mature tissues screened. Expression was somewhat higher in epidermal, vascular and photosynthetic tissue of seedling. Lines characterized went through several generations.

Another example of a broad promoter is the sequence of regulatory region PD2995 (a 600 bp version of p326) set forth in the sequence listing of PCT/US2009/32485. In T0 rice plants, PD2995 expresses very weakly throughout all tissues of the plant in both seedling and mature stages. Strongest expression detected in root tissue and embryo.

ii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA,* 86:7890-7894 (1989)), root cell specific promoters reported by Conkling et al., *Plant Physiol.,* 93:1203-1211 (1990), and the tobacco RD2 promoter.

Another example of a root promoter is the sequence of regulatory region PD3561 set forth in the sequence listing of PCT/US2009/038792. Therein, the expression pattern of the PD3561 regulatory region is described for T0 rice plants overexpressing a construct comprising PD3561 driving expression of EGFP. Expression was observed in roots of seedlings in the cortex, epidermis, and vascular tissues. In mature plants, expression was observed strongly throughout the root with the exception of the root cap and in the cortex, epidermis, and vascular tissues.

iii. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al., *Plant Cell,* 1(9):839-853 (1989)), the soybean trypsin inhibitor promoter (Riggs et al., *Plant Cell,* 1(6):609-621 (1989)), the ACP promoter (Baerson et al., *Plant Mol. Biol.,* 22(2):255-267 (1993)), the stearoyl-ACP desaturase promoter (Slocombe et al., *Plant Physiol.,* 104(4):167-176 (1994)), the soybean α' subunit of β-conglycinin promoter (Chen et al., *Proc. Natl. Acad. Sci. USA,* 83:8560-8564 (1986)), the olcosin promoter (Hong et al., *Plant Mol. Biol.,* 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell Biol.,* 13:5829-5842 (1993)), the beta-amylase promoter, and the barley hordein promoter. Other maturing endosperm promoters include the YP0092, PT0676, and PT0708 promoters.

iv. Ovary Tissue Promoters

Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

v. Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmyc1 (see, Urao, *Plant Mol. Biol.,* 32:571-57 (1996); Conceicao, *Plant,* 5:493-505 (1994)); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan, *Genetics,* 142:1009-1020 (1996)); maize Cat3 (see, GenBank No. L05934; Abler, *Plant Mol. Biol.,* 22:10131-1038 (1993)). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOsFIE2-2, pOsMEA, pOsYp102, and pOsYp285.

vi. Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* 20:647-654 (2001)), YP0097, YP0107, YP0088, YP0143, YP0156, PT0650, PT0695, PT0723, PT0838, PT0879, and PT0740.

vii. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.,* 35:773-778 (1994)), the Cab-1 promoter from wheat (Fejes et al., *Plant Mol. Biol.,* 15:921-932 (1990)), the CAB-1 promoter from spinach (Lubberstedt et al., *Plant Physiol.,* 104:997-1006 (1994)), the cab1R promoter from rice (Luan et al., *Plant Cell,* 4:971-981 (1992)), the pyruvate orthophosphate dikinase (PPDK) promoter from corn (Matsuoka et al., *Proc. Natl. Acad. Sci. USA,* 90:9586-9590 (1993)), the tobacco Lhcb1*2 promoter (Cerdan et al., *Plant Mol. Biol.,* 33:245-255 (1997)), the *Arabidopsis thaliana* SUC2 sucrose-H+ symporter promoter (Truernit et al., *Planta,* 196:564-570 (1995)), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

viii. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner, *Plant Cell,* 3(10):1051-1061 (1991)), the Commelina yellow mottle virus (CoYMV) promoter (Medberry et al., *Plant Cell,* 4(2):185-192 (1992)), and the rice tungro bacilliform virus (RTBV) promoter (Dai et al., *Proc. Natl. Acad. Sci. USA,* 101(2):687-692 (2004)).

ix. Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al. (1999) Nature Biotech 17: 287-291).

x. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

xi. Stem Promoters

A stem promoter may be specific to one or more stem tissues or specific to stem and other plant parts. Stem promoters may have high or preferential activity in, for example, epidermis and cortex, vascular cambium, procambium, or xylem. Examples of stem promoters include YP0018 which is disclosed in US20060015970 and CryIA(b) and CryIA(c) (Braga et al. 2003, Journal of New Seeds 5:209-221).

xii. Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, PT0829, YP0119, and YP0096, as described in the above-referenced patent applications, may also be useful.

xiii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding an abiotic stress tolerance-increasing polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

IV. Transgenic Plants and Plant Cells

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous abiotic stress tolerance-increasing polypeptide whose expression has not previously been confirmed in particular recipient cells.

Techniques for introducing nucleic acids into monocotyledonous and dicotyledonous plants are known in the art, and include, without limitation, Agrobacterium-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/Selection

A population of transgenic plants can be screened and/or selected for those members of the population that have a trait or phenotype conferred by expression of the transgenes. In some embodiments, a population of plants can be selected that has increased tolerance to drought or elevated saline levels, or increased nitrogen use efficiency. In some cases, selection and/or screening can be carried out over multiple transformation events. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in yield (e.g., grain, vegetative biomass, or stem sucrose yield) relative to a control plant that lacks the transgene. Selection and/or screening can be carried out to choose those transgenic plants having a statistically significant difference in an abiotic stress tolerance level relative to a control plant that lacks the transgene. Selected or screened transgenic plants have an altered phenotype as compared to a corresponding control plant, as described in the "Transgenic Plant Phenotypes" section herein.

A population of progeny of a single or distinct transformation event can be screened for those plants having a desired level of expression of an abiotic stress tolerance-increasing polypeptide or nucleic acid. Physical and biochemical methods can be used to identify expression levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Cokhicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetuin, Taxus, Theobroma, Triticosecale, Triticum, Uniola, Veratrum, Vinca, Vitis,* and *Zea.*

Suitable species include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cordgrass), *Medicago sativa* (alfalfa), *Arundo donax* (giant reed), *Secale cereale* (rye), *Salix* spp. (willow), *Eucalyptus* spp. (*eucalyptus*), Triticosecale (*triticum*—wheat×rye) and bamboo.

Suitable species also include *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), and *Brassica juncea.*

Suitable species also include *Beta vulgaris* (sugarbeet), and *Manihot esculenta* (cassava)

Suitable species also include *Lycopersicon esculentum* (tomato), *Lactuca sativa* (lettuce), *Musa paradisiaca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbila maxima* (squash), *Cucurbila moschata* (squash), *Spinacea oleracea* (spinach), *Citrullus lanatus* (watermelon), *Abelmoschus esculentus* (okra), and *Solanum melongena* (eggplant).

Suitable species also include *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum (Huperzia serrata), Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii,* and *Tanacetum parthenium.*

Suitable species also include *Parthenium argentatum* (guayule), *Hevea* spp. (rubber), *Mentha spicata* (mint), *Mentha piperita* (mint), *Bixa orellana,* and *Alstroemeria* spp.

Suitable species also include Rosa spp. (rose), *Dianthus caryophyllus* (carnation), *Petunia* spp. (*petunia*) and *Poinsettia pulcherrima* (poinsettia).

Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy).

In some embodiments, a suitable species can be a wild, weedy, or cultivated *Pennisetum* species such as, but not limited to, *Pennisetum alopecuroides, Pennisetum arnhemicum, Pennisetum caffrum, Pennisetum clandestinum, Penn-* isetum divisum, Pennisetum glaucum, Pennisetum latifolium, Pennisetum macrostachyum, Pennisetum macrourum, Pennisetum orientale, Pennisetum pedicellatum, Pennisetum polystachion, Pennisetum polystachion ssp. Setosum, Pennisetum purpureum, Pennisetum setaceum, Pennisetum subangustum, Pennisetum typhoides, Pennisetum villosum, or hybrids thereof (e.g., Pennisetum purpureum×Pennisetum typhoidum).

In some embodiments, a suitable species can be a wild, weedy, or cultivated Miscanthus species and/or variety such as, but not limited to, Miscanthus×giganteus, Miscanthus sinensis, Miscanthus×ogifbrmis, Miscanthus floridulus, Miscanthus transmorrisonensis, Miscanthus oligostachyus, Miscanthus nepalensis, Miscanthus sacchariflorus, Miscanthus×giganteus 'Amuri', Miscanthus×giganteus 'Nagara', Miscanthus×giganteus 'Illinois', Miscanthus sinensis var. 'Goliath', Miscanthus sinensis var. 'Roland', Miscanthus sinensis var. 'Africa', Miscanthus sinensis var. 'Fern Osten', Miscanthus sinensis var. gracillimus, Miscanthus sinensis var. variegates, Miscanthus sinensis var. purpurascens, Miscanthus sinensis var. 'Malepartus', Miscanthus sacchariflorus var. 'Robusta', Miscanthus sinensis var. 'Silberfedher' (aka. Silver Feather), Miscanthus transmorrisonensis, Miscanthus condensatus, Miscanthus yakushimanum, Miscanthus var. 'Alexander', Miscanthus var. 'Adagio', Miscanthus var. 'Autumn Light', Miscanthus var. 'Cabaret', Miscanthus var. 'Condensatus', Miscanthus var. 'Cosmopolitan', Miscanthus var. 'Dixieland', Miscanthus var. 'Gilded Tower' (U.S. Patent No. PP14,743), Miscanthus var. 'Gold Bar' (U.S. Patent No. PP15,193), Miscanthus var. 'Gracillimus', Miscanthus var. 'Graziella', Miscanthus var. 'Grosse Fontaine', Miscanthus var. 'Hinjo aka Little Nicky' ™, Miscanthus var. 'Juli', Miscanthus var. 'Kaskade', Miscanthus var. 'Kirk Alexander', Miscanthus var. 'Kleine Fontaine', Miscanthus var. 'Kleine Silberspinne' (aka. 'Little Silver Spider'), Miscanthus var. 'Little Kitten', Miscanthus var. 'Little Zebra' (U.S. Patent No. PP13,008), Miscanthus var. 'Lottum', Miscanthus var. 'Malepartus', Miscanthus var. 'Morning Light', Miscanthus var. 'Mysterious Maiden' (U.S. Patent No. PP16,176), Miscanthus var. 'Nippon', Miscanthus var. 'November Sunset', Miscanthus var. 'Parachute', Miscanthus var. 'Positano', Miscanthus var. 'Puenktchen'(aka 'Little Dot'), Miscanthus var. 'Rigoletto', Miscanthus var. 'Sarabande', Miscanthus var. 'Silberpfeil' (aka. Silver Arrow), Miscanthus var. 'Silverstripe', Miscanthus var. 'Super Stripe' (U.S. Patent No. PP18,161), Miscanthus var. 'Strictus', or Miscanthus var. 'Zebrinus'.

In some embodiments, a suitable species can be a wild, weedy, or cultivated sorghum species and/or variety such as, but not limited to, Sorghum almum, Sorghum amplum, Sorghum angustum, Sorghum arundinaceum, Sorghum bicolor (such as bicolor, guinea, caudatum, kafir, and durra), Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum sudanensese, Sorghum timorense, Sorghum trichocladum, Sorghum versicolor, Sorghum virgaturn, Sorghum vulgare, or hybrids such as Sorghum× almum, Sorghum×sudangrass or Sorghum×drummondii.

Thus, the methods and compositions can be used over a broad range of plant species, including species from the dicot genera Brassica, Carthamus, Glycine, Gossypium, Helianthus, Jatropha, Parthenium, Populus, and Ricinus; and the monocot genera Elaeis, Festuca, Hordeum, Lolium, Oryza, Panicum, Pennisetum, Phleum, Poa, Saccharum, Secale, Sorghum, Triticosecale, Triticum, and Zea. In some embodiments, a plant is a member of the species Panicum virgatum (switchgrass), Sorghum bicolor (sorghum, sudangrass), Miscanthus giganteus (miscanthus), Saccharum sp. (energycane), Populus balsamifera (poplar), Zea mays (corn), Glycine max (soybean), Brassica napus (canola), Triticum aestivum (wheat), Gossypium hirsutism (cotton), Oryza sativa (rice), Helianthus annuus (sunflower), Medicago sativa (alfalfa), Beta vulgaris (sugarbeet), or Pennisetum glaucum (pearl millet).

In certain embodiments, the polynucleotides and vectors described herein can be used to transform a number of monocotyledonous and dicotyledonous plants and plant cell systems, wherein such plants are hybrids of different species or varieties of a specific species (e.g., Saccharum sp.× Miscanthus sp., Sorghum sp.×Miscanthus sp., e.g., Panicum virgatum×Panicum amarum, Panicum virgatum×Panicum amarulum, and Pennisetum purpureum×Pennisetum typhoidum).

D. Transgenic Plant Phenotypes

Transgenic plants have increased tolerance to abiotic stress, such as increased tolerance to drought stress or improved water use efficiency, increased tolerance to osmotic stress or to elevated salinity levels, and/or increased tolerance to nitrogen deficiency stress or improved nitrogen use efficiency.

Plant species vary in their capacity to tolerate osmotic stress. Salinity or osmotic stress refers to a set of environmental conditions under which a plant will begin to suffer the effects of elevated salt concentration, such as ion imbalance, decreased stomatal conductance, decreased photosynthesis, decreased growth rate, increased cell death, loss of turgor (wilting), or ovule abortion. For these reasons, plants experiencing salinity stress typically exhibit a significant reduction in biomass and/or yield. Increases in growth rate in low-nitrogen conditions in plants can provide improved plant growth and initial establishment in geographic locales where plant's intake of nitrogenous fertilizers is often insufficient. Improvements in water use efficiency ensure better crop yield stability in drought years, and increased yield in regions with limited rainfall an irrigation. Increases in yield of plants can provide improved food quantity, or improved energy production. Increases in seed production in plants can provide improved nutritional availability in geographic locales where intake of plant foods is often insufficient, or for biofuel production.

In some embodiments, the abiotic stress tolerance level can be increased in a plant by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the abiotic stress tolerance level in a corresponding control plant that does not express the transgene. Abiotic stress tolerance can be assessed by described below or by other acceptable means.

Examples of modified characteristics include photosynthetic efficiency, seedling area, and biomass as it may be measured by plant height, leaf or rosette area, or dry mass. The modified characteristics may be observed and measured at different plant developmental stages, e.g. seed, seedling, bolting, senescence, etc. Often, abiotic stress tolerance can be expressed as ratios or combinations of measurements.

Biomass can include harvestable plant tissues such as leaves, stems, and reproductive structures, or all plant tissues such as leaves, stems, roots, and reproductive structures. In some embodiments, biomass encompasses only above ground plant parts. In some embodiments, biomass encompasses only stem plant parts. In some embodiments, biomass encompasses only above ground plant parts except inflorescence and seed parts of a plant. Biomass can be quantified as dry matter yield, which is the mass of biomass produced (usually reported in T/acre) if the contribution of water is subtracted from the fresh mater weight. Dry matter yield (DMY) yield is calculated using the fresh matter weight (FMW) and a measurement of weight percent moisture (M) in the following equation. DMY=((100−M)/100) *FMW. Biomass can be quantified as fresh matter yield, which is the mass of biomass produced (usually reported in T/acre) on an as-received basis, which includes the weight of moisture.

In some embodiments, a transgenic plant having exogenous nucleic acid expressing an abiotic stress tolerance increasing polypeptide can have increased levels of photosynthetic efficiency in seedlings. For example, the combinations of polypeptides described herein can be expressed in a transgenic plant, resulting in increased levels of photosynthetic efficiency in abiotic stress growth conditions. The level of photosynthetic efficiency can be increased by at least 0.25 percent, e.g., 0.25, 1, 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the level of photosynthetic efficiency in a corresponding control plant that does not express the abiotic stress tolerance-increasing polypeptide. In some cases, the increased levels of photosynthetic efficiency can be in one or more green tissues, e.g., leaves, stems, bulbs, flowers, fruits, young seeds. For example, the level of photosynthetic efficiency can be increased by at least 0.25 percent, e.g., 0.25, 1, 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the level of photosynthetic efficiency in a corresponding control plant that does not express the combination of transgenes.

In some embodiments, a transgenic plant provided herein can have increased growth rates in seedlings. For example, a combination of the polypeptides described herein can be expressed in a transgenic plant, resulting in increased growth rate in growth conditions of abiotic stress. The growth rate can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the growth rate in a corresponding control plant that does not express the combination. Growth rate can be measured in seedlings, developing, or mature plants and measured for periods of time such as about 1 hour, 3 hours, 6 hours, 12 hours, 1 day, 3 days, 5 days, 10 days, 1 month, 3 months, 6 months, 12 months, or the entire lifespan of a plant.

In some embodiments, a transgenic plant provided herein can have increased growth rates in one or more vegetative and reproductive tissues, e.g., leaves, stems, flowers, bulbs, fruits, young seeds. For example, the growth rate can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the growth rate in a corresponding control plant that does not express the transgene.

In some cases, a transgenic plant described herein and having enhanced yield stability can exhibit a height that is from about 5% to about 100% greater (e.g., about 5% to about 12%; about 5% to about 40%; about 5% to about 80%; about 7% to about 20%; about 10% to about 15%; about 10% to about 50%; about 10% to about 90%; about 20% to about 25%; about 20% to about 45%; about 20% to about 75%; about 25% to about 60%; about 25% to about 100%; about 30% to about 50%; about 30% to about 70%; about 40% to about 50%; about 45% to about 60%; about 50% to about 80%; about 55% to about 75%; about 60% to about 80%; about 60% to about 95%; about 75% to about 100%; about 80% to about 100%; about 90% to about 95%; or about 95% to about 100% greater) than a plant not expressing one or two of the polypeptides encoded by the exogenous nucleic acid when grown under abiotic stress conditions or following such conditions.

In some instances, a transgenic plant provided herein and having enhanced yield stability can exhibit greater leaf area or greater leaf length than a corresponding control plant (e.g., wild-type plant or a plant lacking at least one of the transgenes of the transgenic plant). For example, a transgenic plant can have a leaf area that is 5% to about 100% greater (e.g., about 5% to about 7%; about 5% to about 20%; about 8% to about 80%; about 10% to about 20%; about 10% to about 25%; about 10% to about 50%; about 10% to about 90%; about 15% to about 25%; about 20% to about 45%; about 20% to about 70%; about 25% to about 40%; about 25% to about 100%; about 30% to about 50%; about 30% to about 70%; about 40% to about 50%; about 45% to about 60%; about 50% to about 80%; about 55% to about 75%; about 60% to about 80%; about 60% to about 95%; about 75% to about 100%; about 80% to about 100%; about 90% to about 95%; or about 95% to about 100% greater) than a corresponding control plant when grown under abiotic stress or following such conditions.

A plant in which expression of an abiotic stress tolerance-increasing polypeptide is modulated can have increased levels of seed production. The level can be increased by at least 2 percent, e.g., 2, 3, 4, 5, 10, 15, 20, 25, 30, 35, 40, 45, 50, 55, 60, 65, 70, 75, 80, 85, 90, 95, 100, 110, 120, 130, 140, 150, 160, 170, 180, 190, or 200 percent or more, as compared to the seed production level in a corresponding control plant that does not express the transgene. Increases in seed production can provide improved nutritional availability in geographic locales where intake of plant foods is often insufficient, or for biofuel production.

In other cases, when a polypeptides described herein is expressed in a transgenic plant, the transgenic plant can exhibit enhanced yield stability and can exhibit a seed number (number of seeds per plant) from about 10% to about 95% greater (e.g., from about 10% to about 20%; from about 10% to about 50%; from about 10% to about 70%; from about 20% to about 60%; from about 20% to about 75%; from about 25% to about 85%; from about 30% to about 70%; from about 35% to about 90%; from about 40% to about 60%; from about 40% to about 85%; from about 50% to about 80%; from about 50% to about 90%; or from about 70% to about 90% greater) than a control plant not expressing the combination of polypeptides when grown under abiotic stress conditions. In certain cases, when a polypeptide described herein is expressed in a transgenic plant, the transgenic plant can exhibit enhanced yield stability and can exhibit an increase in seed weight per plant from about 5% to about 100% greater (e.g., about 5% to about 12%; about 5% to about 40%; about 5% to about 80%; about 7% to about 20%; about 10% to about 15%; about 10% to about 50%; about 10% to about 90%; about 20% to about 25%; about 20% to about 45%; about 20% to about 75%; about 25% to about 60%; about 25% to about 100%; about 30% to about 50%; about 30% to about 70%; about 40% to about 50%; about 45% to about 60%; about 50% to about 80%; about 55% to about 75%; about 60% to about 80%; about 60% to about 95%; about 75% to about 100%; about 80% to about 100%; about 90% to about 95%; or about 95% to about 100% greater) than the seed weight in a plant not expressing the polypeptide when grown under abiotic stress conditions.

Transgenic plants provided herein and having drought stress resistance can exhibit a lower transpiration rate compared to control plants of the same genetic background. Transpiration rate is a physiological parameter that is indicative of how well a plant can tolerate drought conditions. For example, plants with a low transpiration rate are expected to lose water more slowly than plants with higher transpiration rates and therefore would be expected to better withstand drought conditions (i.e., have better drought tolerance). When a polypeptide described herein is expressed in a transgenic plant, the transgenic plant can exhibit enhanced yield stability and can exhibit a transpiration rate that is reduced by about 0.25% to 100% (e.g., 0.27%, 0.3%, 0.43%, 0.55%, 0.7%, 0.99%, 1%, 2%, 4%, 6%, 8%, 10%, 12%, 15%, 18%, 22%, 28%, 35%, 37%, 42%, 45%, 47%, 50%, 55%, 64%, 68%, 71%, 75%, 77%, 80%, 83%, 86%, 89%, 90%, 92%, 95%, 98%, or 99%) as compared to the transpiration rate in a corresponding control plant when grown under drought conditions.

In some cases, a transgenic plant expressing a polypeptide described herein can exhibit enhanced yield stability and can exhibit a decreased change in photosynthetic activity ($\Delta Fv/Fm$) after exposure to abiotic stress conditions as compared to a corresponding control plant that does not express the polypeptides when grown under the same conditions. In some cases, a transgenic plant expressing a polypeptide described herein can exhibit enhanced yield stability and can exhibit an increased change in photosynthetic activity ($\Delta Fv/Fm-D_2$) post stress treatment as compared to a corresponding control plant when grown under the same conditions. For example, a transgenic plant expressing a polypeptide described herein can exhibit a $\Delta Fv/Fm$ of from about 0.1 to about 0.8 (e.g., about 0.2 to about 0.28; about 0.2 to about 0.32; about 0.22 to about 0.35; about 0.29 to about 0.4; about 0.3 to about 0.45; about 0.33 to about 0.41; about 0.35 to about 0.5; about 0.4 to about 0.8; about 0.46 to about 0.52; about 0.5 to about 0.65; about 0.5 to about 0.8; about 0.6 to about 0.7; about 0.6 to about 0.9; about 0.65 to about 0.75; about 0.7 to about 0.9; or about 0.75 to about 0.8) or a $\Delta Fv/Fm-D_2$ range of from about 0.03 to about 0.8 (e.g., about 0.03 to about 0.08; about 0.03 to about 0.032; about 0.04 to about 0.05; about 0.09 to about 0.4; about 0.05 to about 0.5; about 0.075 to about 0.1; about 0.08 to about 0.2; about 0.3 to about 0.45; about 0.33 to about 0.41; about 0.35 to about 0.5; about 0.4 to about 0.8; about 0.46 to about 0.52; about 0.5 to about 0.65; about 0.5 to about 0.8; about 0.6 to about 0.7; about 0.6 to about 0.9; about 0.65 to about 0.75; about 0.7 to about 0.9; about 0.75 to about 0.85; or about 0.8 to about 0.9). In some embodiments, photosynthetic activity can be reduced by about 0.25% to about 100% (e.g., about 0.25% to about 0.4%, about 0.25% to about 1%, about 0.25% to about 5%, about 0.5% to about 10%, about 1% to about 5%, about 1% to about 10%, about 2% to about 8%, about 3% to about 20%, about 5% to about 7%; about 5% to about 20%; about 5% to about 45%; about 8% to about 80%; about 10% to about 20%; about 10% to about 25%; about 10% to about 50%; about 10% to about 90%; about 15% to about 25%; about 20% to about 45%; about 20% to about 70%; about 25% to about 40%; about 25% to about 99%; about 30% to about 50%; about 30% to about 70%; about 40% to about 50%; about 45% to about 60%; about 50% to about 80%; about 55% to about 75%; about 60% to about 80%; about 60% to about 95%; about 75% to about 99%; about 80% to about 99%; about 90% to about 95%; or about 95% to about 100%) as compared to the photosynthetic activity in a corresponding control plant following abiotic stress conditions.

Typically, a difference in the amount of abiotic stress tolerance in a transgenic plant relative to a control plant is considered statistically significant at $p \leq 0.05$ with an appropriate parametric or non-parametric statistic, e.g., Chi-square test, Student's t-test, Mann-Whitney test, or F-test. In some embodiments, a difference in the amount of abiotic stress tolerance is statistically significant at $p<0.01$, $p<0.005$, or $p<0.001$. A statistically significant difference in, for example, the amount of abiotic stress tolerance in a transgenic plant compared to the amount of a control plant indicates that the recombinant nucleic acid present in the transgenic plant results in altered abiotic stress tolerance levels.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, S1 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

V. Modifying Endogenous Nucleic Acids Encoding Abiotic Stress Tolerance-Increasing Polypeptides This document also features plant cells and plants in which an endogenous abiotic stress tolerance-increasing nucleic acid described herein has been modified (e.g., a regulatory region, intron, or coding region of the abiotic stress tolerance-increasing nucleic acid has been modified). The abiotic stress tolerance of such plants is altered relative to the corresponding level of a control plant in which the endogenous nucleic acid is not modified. Such plants are referred to herein as modified plants and may be used to produce, for example, increased amounts of abiotic stress tolerance.

Endogenous nucleic acid can be modified by homologous recombination techniques. For example, sequence specific endonucleases (e.g., zinc finger nucleases (ZFNs)) and meganucleases can be used to stimulate homologous recombination at endogenous plant genes. See, e.g., Townsend et al., *Nature* 459:442-445 (2009); Tovkach et al., *Plant J.*, 57:747-757 (2009); and Lloyd et al., *Proc. Natl. Acad. Sci. USA*, 102:2232-2237 (2005). In particular, ZFNs engineered to create DNA double strand breaks at specific loci can be used to make targeted sequence changes in endogenous plant genes. For example, an endogenous plant gene can be replaced with a variant containing one or more mutations (e.g., produced using site-directed mutagenesis or directed evolution). In some embodiments, site directed mutagenesis is achieved via non-homologous end joining such that after breaking DNA, endogenous DNA repair mechanisms ligate the break, often introducing slight deletions or additions that can be screened at the cell or plant level for desired phenotypes. Moore and Haber, *Mol Cell Biol.*, 16(5):2164-73 (1996).

In some embodiments, endogenous nucleic acids can be modified by methylation or demethylation such that the expression of the modified endogenous nucleic acid is altered. For example, a double stranded RNA can be used to activate gene expression by targeting noncoding regulatory regions in gene promoters. See Shibuya et al., *Proc Natl Acad Sci USA*, 106(5): 1660-1665 (2009); and Li et al., *Proc Natl Acad Sci USA*, 103(46):17337-42 (2006). In some embodiments, ZFNs engineered to create DNA double strand breaks at specific loci can be used to insert a DNA fragment having at least one region that overlaps with the endogenous DNA to facilitate homologous recombination, such that the non-overlapping portion of the DNA fragment is integrated at the break site. For example, a fragment can be inserted into an endogenous promoter and/or regulatory region at a specific site where a ZFN creates a double stranded break to alter the expression of an endogenous gene. For example, a fragment that is inserted into an endogenous gene coding region at a specific site where a ZFN creates a double stranded break can result in expression of a chimeric gene. For example, a fragment that functions as a regulator region or promoter that is inserted into an endogenous DNA region immediately upstream of a gene coding sequence at a specific site where a ZFN creates a double stranded break can result in altered expression of the endogenous gene.

In some embodiments, endogenous nucleic acids can be modified using activation tagging. For example, a vector containing multiple copies of an enhancer element from the constitutively active promoter of the cauliflower mosaic virus (CaMV) 35S gene can be used to activate an endogenous gene. See, Weigel et al., *Plant Physiology*, 122:1003-1013 (2000).

In some embodiments, endogenous nucleic acids can be modified by introducing all engineered transcription activation/repression factor (e.g., zinc finger protein transcription factor, or ZFP TF. See, for example, the world wide web at sangamo.com/tech/tech_plat_over.html#whatarezfp). For example, a synthetic transcription facto sequence of a zinc finger DNA binding domain and a VP16 activation domain can be designed to bind to a specific endogenous DNA site and alter expression of an endogenous gene. An engineered transcription activation/repression factor (such as ZFP TF) can activate, repress, or switch the target endogenous abiotic stress tolerance gene expression by binding specifically to the promoter region or coding region of the endogenous gene. Engineered nucleases that cleave specific DNA sequences in vivo can also be valuable reagents for targeted mutagenesis. One such class of sequence-specific nucleases can be created by fusing transcription activator-like effectors (TALEs) to the catalytic domain of the FokI endonuclease. Both native and custom TALE-nuclease fusions direct DNA double-strand breaks to specific, targeted sites. Christian et al., *Genetics* 186: 757-761 (2010).

In some embodiments, endogenous nucleic acids can be modified by mutagenesis. Genetic mutations can be introduced within regenerable plant tissue using one or more mutagenic agents. Suitable mutagenic agents include, for example, ethyl methane sulfonate (EMS), N-nitroso-N-ethyllurea (ENU), methyl N-nitrosoguanidine (MNNG), ethidium bromide, diepoxybutane, ionizing radiation, x-rays, UV rays and other mutagens known in the art.

Suitable types of mutations include, for example, insertions or deletions of nucleotides, and transitions or transversions in the endogenous nucleic acid sequence. In one embodiment, TILLING (Targeted Induced Local Lesions In Genomes) can be used to produce plants having a modified endogenous nucleic acid. TILLING combines high-density mutagenesis with high-throughput screening methods. See, for example, McCallum et al., *Nat Biotechnol* 18: 455-457 (2000); reviewed by Stemple, *Nat Rev Genet* 5(2):145-50 (2004).

In some embodiments, an endogenous nucleic acid can be modified via a gene silencing technique. See, for example, the section herein regarding "Inhibition of Expression of an abiotic stress tolerance-Increasing Polypeptide."

A population of plants can be screened and/or selected for those members of the population that have a modified nucleic acid. A population of plants also can be screened and/or selected for those members of the population that have a trait or phenotype conferred by expression of the modified nucleic acid. As an alternative, a population of plants can be screened for those plants having a desired trait, such as a modulated level of abiotic stress tolerance. For example, a population of progeny can be screened for those plants having a desired level of expression of an abiotic stress tolerance-increasing polypeptide or nucleic acid. Physical and biochemical methods can be used to identify modified nucleic acids and/or expression levels as described with transgenic plants. Selection and/or screening can be carried out over one or more generations, and/or in more than one geographic location. In some cases, plants can be grown and selected under conditions which induce a desired phenotype or are otherwise necessary to produce a desired phenotype in a modified plant. In addition, selection and/or screening can be applied during a particular developmental stage in which the phenotype is expected to be exhibited by the plant. Selection and/or screening can be carried out to choose those modified plants having a statistically significant difference in an abiotic stress tolerance level relative to a control plant in which the nucleic acid has not been modified. Selected or screened modified plants have an altered phenotype as compared to a corresponding control plant, as described in the "Transgenic Plant Phenotypes" section herein.

Although a plant or plant cell in which an endogenous abiotic stress tolerance-increasing nucleic acid has been modified is not transgenic for that particular nucleic acid, it will be appreciated that such a plant or cell may contain transgenes. For example, a modified plant can contain a transgene for other traits, such as herbicide tolerance or insect resistance. As another example, a modified plant can contain one or more transgenes that, in conjunction with modifications of one or more endogenous nucleic acids, exhibits an increase in abiotic stress tolerance.

As with transgenic plant cells, modified plant cells can constitute part or all of a whole plant. Such plants can be grown in the same manner as described for transgenic plants and can be bred or propagated in the same manner as described for transgenic plants.

VI. Plant Breeding

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs). SSR polymorphisms can be identified, for example, by making sequence specific probes and amplifying template DNA from individuals in the population of interest by PCR. For example, PCR techniques can be used to enzymatically amplify a genetic marker associated with a nucleotide sequence conferring a specific trait (e.g., nucleotide sequences described herein). PCR can be used to amplify specific sequences from DNA as well as RNA, including sequences from total genomic DNA or total cellular RNA. When using RNA as a source of template, reverse transcriptase can be used to synthesize complementary DNA (cDNA) strands. Various PCR methods are described, for example, in *PCR Primer: A Laboratory Manual,* Dieffenbach and Dveksler, eds., Cold Spring Harbor Laboratory Press, 1995.

Generally, sequence information from polynucleotides flanking the region of interest or beyond is employed to design oligonucleotide primers that are identical or similar in sequence to opposite strands of the template to be amplified. Primers are typically 14 to 40 nucleotides in length, but can range from 10 nucleotides to hundreds of nucleotides in length. Template and amplified DNA is repeatedly denatured at a high temperature to separate the double strand, then cooled to allow annealing of primers and the extension of nucleotide sequences through the microsatellite, resulting in sufficient DNA for detection of PCR products. If the probes flank an SSR in the population, PCR products of different sizes will be produced. See, e.g., U.S. Pat. No. 5,766,847.

PCR products can be qualitative or quantitatively analyzed using several techniques. For example, PCR products can be stained with a fluorescent molecule (e.g., PicoGreen® or OliGreen®) and detected in solution using spectrophotometry or capillary electrophoresis. In some cases, PCR products can be separated in a gel matrix (e.g., agarose or polyacrylamide) by electrophoresis, and size-fractionated bands comprising PCR products can be visualized using nucleic acid stains. Suitable stains can fluoresce under UV light (e.g., Ethidium bromide, GR Safe, SYBR® Green, or SYBR® Gold). The results can be visualized via transillumination or epi-illumination, and an image of the fluorescent pattern can be acquired using a camera or scanner, for example. The image can be processed and analyzed using specialized software (e.g., ImageJ) to measure and compare the intensity of a band of interest against a standard loaded on the same gel.

Alternatively, SSR polymorphisms can be identified by using PCR product(s) as a probe against Southern blots from different individuals in the population. See, U. H. Refseth et al., (1997) *Electrophoresis* 18: 1519. Briefly, PCR products are separated by length through gel electrophoresis and transferred to a membrane. SSR-specific DNA probes, such as oligonucleotides labeled with radioactive, fluorescent, or chromogenic molecules, are applied to the membrane and hybridize to bound PCR products with a complementary nucleotide sequence. The pattern of hybridization can be visualized by autoradiography or by development of color on the membrane, for example.

In some cases, PCR products can be quantified using a real-time thermocycler detection system. For example, Quantitative real-time PCR can use a fluorescent dye that forms a DNA-dye-complex (e.g., SYBR® Green), or a fluorophore-containing DNA probe, such as single-stranded oligonucleotides covalently bound to a fluorescent reporter or fluorophore (e.g. 6-carboxyfluorescein or tetrachlorofluoresein) and quencher (e.g., tetramethylrhodamine or dihydrocyclopyrroloindole tripeptide minor groove binder). The fluorescent signal allows detection of the amplified product in real time, thereby indicating the presence of a sequence of interest, and allowing quantification of the copy number of a sequence of interest in cellular DNA or expression level of a sequence of interest from cellular mRNA.

The identification of RFLPs is discussed, for example, in Alonso-Blanco et al. (*Methods in Molecular Biology,* vol. 82, "*Arabidopsis* Protocols", pp. 137-146, J. M. Martinez-Zapater and J. Salinas, eds., c. 1998 by Humana Press, Totowa, N.J.); Burr ("Mapping Genes with Recombinant Inbreds", pp. 249-254, in Freeling, M. and V. Walbot (Ed.), *The Maize Handbook,* c. 1994 by Springer-Verlag New York, Inc.: New York, N.Y., USA; Berlin Germany; Burr et al. *Genetics* (1998) 118: 519; and Gardiner, J. et al., (1993) *Genetics* 134: 917). For example, to produce a RFLP library enriched with single- or low-copy expressed sequences, total DNA can be digested with a methylation-sensitive enzyme (e.g., Pst1). The digested DNA can be separated by size on a preparative gel. Polynucleotide fragments (500 to 2000 bp) can be excised, eluted and cloned into a plasmid vector (e.g., pUC18). Southern blots of plasmid digests can be probed with total sheared DNA to select clones that hybridize to single- and low-copy sequences. Additional restriction endonucleases can be tested to increase the number of polymorphisms detected.

The identification of AFLPs is discussed, for example, in EP 0 534 858 and U.S. Pat. No. 5,878,215. In general, total cellular DNA is digested with one or more restriction enzymes. Restriction halfsite-specific adapters are ligated to all restriction fragments and the fragments are selectively amplified with two PCR primers that have corresponding adaptor and restriction site specific sequences. The PCR products can be visualized after size-fractionation, as described above.

In some embodiments, the methods are directed to breeding a plant line. Such methods use genetic polymorphisms identified as described above in a marker assisted breeding program to facilitate the development of lines that have a desired alteration in the abiotic stress tolerance trait. Once a suitable genetic polymorphism is identified as being associated with variation for the trait, one or more individual plants are identified that possess the polymorphic allele correlated with the desired variation. Those plants are then used in a breeding program to combine the polymorphic allele with a plurality of other alleles at other loci that are correlated with the desired variation. Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plants is selfed or crossed a different plant to produce seed which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for fungal resistance or bacterial resistance. Selection for such other traits can be carried out before, during or after identification of individual plants that possess the desired polymorphic allele.

VII. Articles of Manufacture

Transgenic plants provided herein have various uses in the agricultural and energy production industries. For example, transgenic plants described herein can be used to make animal feed and food products. Such plants, however, are often particularly useful as a feedstock for energy production.

Transgenic plants described herein produce higher yields of grain and/or biomass per hectare, relative to control plants that lack the exogenous nucleic acid or lack the modified endogenous nucleic acid when grown on soils with elevated abiotic stress levels. For example, transgenic plants described herein can have a grain yield that is increased about 5% to about 20% (e.g., increased 5% to 10%, 5% to 15%, 10% to 15%, 10% to 20%, or 15% to 20%) relative to that of control plants lacking the exogenous nucleic acid or lacking the modified endogenous nucleic acid. In some embodiments, such transgenic plants provide equivalent or even increased yields of grain and/or biomass per hectare relative to control plants when grown under conditions of reduced inputs such as fertilizer and/or water. Thus, such transgenic plants can be used to provide yield stability at a lower input cost and/or under environmentally stressful conditions such as elevated abiotic stress levels.

In some embodiments, plants described herein have a composition that permits more efficient processing into free sugars, and subsequently ethanol, for energy production. In some embodiments, such plants provide higher yields of ethanol, butanol, dimethyl ether, other biofuel molecules, and/or sugar-derived co-products per kilogram of plant material, relative to control plants. Such processing efficiencies are believed to be derived from the composition of the plant material, including, but not limited to, content of glucan, cellulose, hemicellulose, and lignin. By providing higher yields at an equivalent or even decreased cost of production, the transgenic plants described herein improve profitability for farmers and processors as well as decrease costs to consumers.

Seeds from transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

The invention will be further described in the following examples, which do not limit the scope of the invention described in the claims.

EXAMPLES

Example 1

Production of Transgenic Rice Plants

Transformed Indica IR64 rice plants were made both with and without selection markers. Marker-free (MF) plants were made by co-transforming distinct binary vectors for expressing either the selection marker gene neomycin phosphotransferase (NPT II) or the trans gene of interest. The regenerated plants were then selfed, and marker-free segregants positive for the transgene of interest were selected for testing. Some plants (M+) were made by transformation with single binary vectors expressing both the marker selection gene and the transgene of interest, and thus the transformed plants retained the marker.

Immature embryos of Indica rice variety IR64 were harvested, transformed, selected, and the transgenic plants regenerated using established methods (see U.S. Pat. No. 6,329,571). Transformation was verified and followed in subsequent generations by PCR.

The plants tested are shown in Table 1. Ninety-five (95) independent transformation events were generated and tested.

TABLE 1

Transgenic Indica rice plants tested.

| Transformant designation | Promoter | Encoded polypeptide | Marker Free events | Marker + events |
| --- | --- | --- | --- | --- |
| OsIB-1805402 | PD2995 (SEQ ID NO 21 in WO2009099899) | SEQ ID NO 2 | 5 | 12 |
| OsIB-872104m | PD3317 (SEQ ID NO 404) | SEQ ID NO 337 | 7 | 5 |
| OsIB-26006 | PD3562 (SEQ ID NO 5 in WO2009146015) | SEQ ID NO 61 | 24 | 2 |
| OsIB-375578m | PD3141 (SEQ ID NO 23 in WO2009099899) | SEQ ID NO 205 | 11 | 8 |
| OsIB-625057 | PD3141 | SEQ ID NO 27 | 4 | 3 |
| OsIB-878355 | PD3141 | SEQ ID NO 209 | 3 | 3 |
| OsIB-258841 | PD3141 | SEQ ID NO 370 | 3 | 5 |

Example 2

Abiotic Stress Tests

Forty (40) day old seedlings of the transgenic events plus untransformed IR64 controls were planted in the test plot, for testing in random block design with three replicates, under each of the six abiotic stress conditions described below. Planting density was 20×15 cm.

For drought stress D1, watering ceased about 15 days before flowering. The stress was imposed for 15-18 days, and then released at the post flowering stage. For drought stress D2, watering ceased post flowering, and the stress was maintained for until maturity.

For salinity stress tests S1 and S2, the test plots were irrigated with a sodium chloride solution from the seedling to maturity stages. For the S1 test, soil electrical conductivity (EC) was maintained between 4 and 5 deciSiemens per meter (dS/m), and for the S2 test, the EC was between 6 and 7 dS/m.

For the nitrogen deficiency stress assays N1 and N2, fertilizer was applied in three doses at different growth stages from seedling to maturity at total rates of 50 and 75 kg Nitrogen per hectare respectively, i.e., at one half and three quarters the normal rate respectively.

Example 3

Results of Abiotic Stress Tests

Grain was harvested from mature plants, and grain weight per plant was recorded for five plants from each replicate in all treatments. Tables 2-7 show yield results for plants with yield performance statistically superior to the respective controls. In Tables 2-7, suffixes of transformant designations denote distinct transformation events.

TABLE 2

Results of the D1 test; Least Significant Difference at p < 0.01 for IR64 control (LSD) is 5.15

| Plant | Yield (grams per plant) | % higher than IR64 |
|---|---|---|
| IR 64 | 8.39 | n/a |
| OSIB-625057-MF-004 | 16.88 | 101.19 |
| OSIB-878355-M+004 | 15.28 | 82.12 |
| OSIB-878355-M+005 | 13.80 | 64.48 |
| OSIB-878355-MF-002 | 17.82 | 112.40 |
| OsIB-258841-M+005 | 16.96 | 102.15 |
| OSIB375578M-M+019 | 16.80 | 100.24 |
| OSIB375578M-MF-006 | 17.31 | 106.32 |
| OSIB375578M-MF-009 | 18.35 | 118.71 |
| OSIB375578M-MF-010 | 16.22 | 93.33 |
| OsIB-872104m-MF-005 | 18.74 | 123.36 |
| OSIB-26006-M+025 | 18.01 | 114.66 |
| OSIB-26006-M+026 | 20.27 | 141.60 |
| OSIB-26006-MF-004 | 17.92 | 113.59 |
| OSIB-26006-MF-006 | 18.23 | 117.28 |
| OSIB-26006-MF-009 | 18.90 | 125.27 |
| OSIB-26006-MF-010 | 14.27 | 70.08 |
| OSIB-26006-MF-016 | 15.97 | 90.35 |
| OSIB-26006-MF-019 | 13.74 | 63.77 |
| OSIB-26006-MF-023 | 18.32 | 118.36 |
| OSIB-1805402-M+012 | 15.82 | 88.56 |
| OSIB-1805402-M+017 | 14.12 | 68.30 |

TABLE 3

Results of the D2 test; LSD = 1.809

| Plant | Yield (grams per plant) | % higher than IR64 |
|---|---|---|
| IR 64 | 2.48 | n/a |
| OSIB-878355-M+004 | 6.23 | 151.21 |
| OsIB-258841-M+005 | 5.82 | 134.68 |
| OSIB375578M-M+014 | 10.49 | 322.98 |
| OSIB375578M-MF-001 | 5.15 | 107.66 |
| OSIB375578M-MF-006 | 5.26 | 112.10 |
| OSIB375578M-MF-010 | 4.56 | 83.87 |
| OSIB-872104m-M+008 | 5.39 | 117.34 |
| OSIB-872104m-MF-002 | 4.28 | 72.58 |
| OSIB-26006-MF-001 | 5.02 | 102.42 |
| OSIB-26006-MF-002 | 5.59 | 125.40 |
| OSIB-26006-MF-003 | 5.68 | 129.03 |
| OSIB-26006-MF-004 | 5.92 | 138.71 |
| OSIB-26006-MF-009 | 5.50 | 121.77 |
| OSIB-26006-MF-010 | 4.57 | 84.27 |
| OSIB-26006-MF-011 | 4.79 | 93.15 |
| OSIB-26006-MF-013 | 6.42 | 158.87 |
| OSIB-26006-MF-017 | 4.90 | 97.58 |
| OSIB-26006-MF-018 | 6.27 | 152.82 |
| OSIB-26006-MF-019 | 5.78 | 133.06 |
| OSIB-1805402-M+010 | 5.26 | 112.10 |
| OSIB-1805402-M+017 | 6.04 | 143.55 |

TABLE 4

Results of the SI test; LSD = 2.82

| Plant | Yield (grams per plant) | % higher than IR64 |
|---|---|---|
| IR 64 | 4.02 | n/a |
| OsIB-258841-M+005 | 7.57 | 88.31 |
| OsIB-258841-M+008 | 7.48 | 86.07 |
| OSIB375578M-M+014 | 9.75 | 142.54 |
| OSIB375578M-M+019 | 9.28 | 130.85 |
| OSIB375578M-MF-010 | 7.56 | 88.06 |
| OSIB-872104m-M+008 | 6.86 | 70.65 |
| OSIB-872104m-M+010 | 13.53 | 236.57 |
| OSTB-872104m-MF-002 | 6.80 | 69.15 |
| OSIB-872104m-MF-003 | 7.57 | 88.31 |
| OSIB-872104m-MF-006 | 7.19 | 78.86 |
| OSIB-26006-MF-001 | 9.31 | 131.59 |
| OSIB-26006-MF-002 | 8.80 | 118.91 |
| OSIB-26006-MF-003 | 9.04 | 124.88 |
| OSIB-26006-MF-006 | 10.02 | 149.25 |
| OSIB-26006-MF-009 | 10.23 | 154.48 |
| OSIB-26006-MF-010 | 8.41 | 109.20 |
| OSIB-26006-MF-011 | 7.28 | 81.09 |
| OSIB-26006-MF-012 | 7.38 | 83.58 |
| OSIB-26006-MF-013 | 11.16 | 177.61 |
| OSIB-26006-MF-016 | 6.91 | 71.89 |
| OSIB-26006-MF-021 | 7.13 | 77.36 |
| OSIB-1805402-M+009 | 9.00 | 123.88 |
| OSIB-1805402-M+010 | 9.23 | 129.60 |
| OSIB-1805402-M+012 | 9.07 | 125.62 |
| OSIB-1805402-M+013 | 8.63 | 114.68 |
| OSIB-1805402-M+017 | 7.71 | 91.79 |
| OSIB-1805402-MF-003 | 8.68 | 115.92 |
| OSIB-1805402-MF-004 | 7.45 | 85.32 |

TABLE 5

Results of the S2 test; LSD = 2.66

| Plant | Yield (grams per plant) | % higher than IR64 |
|---|---|---|
| IR 64 | 3.09 | n/a |
| OsIB-258841-M+008 | 5.84 | 89.00 |
| OSIB375578M-M+014 | 7.15 | 69.52 |
| OSIB375578M-M+015 | 6.11 | 42.24 |
| OSIB375578M-M+016 | 6.26 | 51.88 |
| OSIB375578M-M+018 | 6.64 | 56.71 |
| OSIB375578M-MF-006 | 6.78 | 55.57 |
| OSIB375578M-MF-010 | 11.04 | 117.26 |
| OSIB-872104m-MF-003 | 10.48 | 66.94 |
| OSIB-872104m-MF-005 | 6.02 | 27.96 |
| OSIB-872104m-MF-007 | 8.77 | 94.35 |
| OSIB-26006-M+026 | 6.15 | 34.89 |
| OSIB-26006-MF-004 | 8.10 | 81.46 |
| OSIB-26006-MF-006 | 9.00 | 72.96 |
| OSIB-26006-MF-008 | 5.74 | 29.44 |
| OSIB-26006-MF-009 | 7.47 | 76.31 |
| OSIB-26006-MF-011 | 6.80 | 49.67 |
| OSIB-26006-MF-013 | 6.82 | 54.85 |
| OSIB-26006-MF-017 | 7.98 | 71.70 |
| OSIB-1805402-M+012 | 7.40 | 54.01 |
| OSIB-1805402-M+017 | 7.33 | 57.30 |
| OSIB-1805402-MF-003 | 8.41 | 72.58 |
| OSIB-1805402-MF-004 | 5.91 | 33.53 |

TABLE 6

Results of the N1 test; LSD = 4.07

| Plant | Yield (grams per plant) | % higher than IR64 |
|---|---|---|
| IR 64 | 8.58 | n/a |
| OSIB-625057-M+005 | 13.68 | 59.44 |
| OSIB-625057-M+006 | 15.75 | 83.57 |
| OSIB-625057-M+007 | 12.81 | 49.30 |
| OSIB-625057-MF-003 | 17.96 | 109.32 |
| OSIB-878355-M+004 | 14.82 | 72.73 |

TABLE 6-continued

Results of the N1 test; LSD = 4.07

| Plant | Yield (grams per plant) | % higher than IR64 |
|---|---|---|
| OSIB-878355-M+005 | 17.01 | 98.25 |
| OSIB-878355-MF-001 | 15.11 | 76.11 |
| OSIB-878355-MF-002 | 17.15 | 99.88 |
| OsIB-258841-M+005 | 15.86 | 84.85 |
| OsIB-258841-M+006 | 19.97 | 132.75 |
| OsIB-258841-M+008 | 21.82 | 154.31 |
| OSIB375578M-M+016 | 13.89 | 61.89 |
| OSIB375578M-M+018 | 19.46 | 126.81 |
| OSIB375578M-MF-001 | 14.54 | 69.46 |
| OSIB375578M-MF-002 | 15.11 | 76.11 |
| OSIB375578M-MF-004 | 15.79 | 84.03 |
| OSIB375578M-MF-010 | 14.93 | 74.01 |
| OSIB-872104m-M+008 | 15.70 | 82.98 |
| OSIB-872104m-M+009 | 13.40 | 56.18 |
| OSIB-872104m-M+010 | 14.25 | 66.08 |
| OSIB-872104m-MF-002 | 16.96 | 97.67 |
| OSIB-872104m-MF-003 | 13.71 | 59.79 |
| OSIB-872104m-MF-004 | 15.74 | 83.45 |
| OSIB-872104m-MF-005 | 15.22 | 77.39 |
| OSIB-872104m-MF-007 | 13.19 | 53.73 |
| OSIB375578M-MF-006 | 18.06 | 110.49 |
| OSIB-26006-MF-002 | 13.84 | 61.31 |
| OSIB-26006-MF-003 | 13.68 | 59.44 |
| OSIB-26006-MF-004 | 16.80 | 95.80 |
| OSIB-26006-MF-006 | 16.01 | 86.60 |
| OSIB-26006-MF-008 | 16.11 | 87.76 |
| OSIB-26006-MF-009 | 17.22 | 100.70 |
| OSIB-26006-MF-010 | 13.82 | 61.07 |
| OSIB-26006-MF-011 | 14.93 | 74.01 |
| OSIB-26006-MF-013 | 14.26 | 66.20 |
| OSIB-26006-MF-014 | 13.48 | 57.11 |
| OSIB-26006-MF-016 | 12.77 | 48.83 |
| OSIB-26006-MF-018 | 13.18 | 53.61 |
| OSIB-26006-MF-019 | 16.51 | 92.42 |
| OSIB-26006-M+025 | 14.20 | 65.50 |
| OSIB-1805402-M+007 | 14.07 | 63.99 |
| OSIB-1805402-M+009 | 17.73 | 106.64 |
| OSIB-1805402-M+012 | 13.14 | 53.15 |
| OSIB-1805402-M+017 | 17.51 | 104.08 |
| OSIB-1805402-MF-003 | 15.89 | 85.20 |
| OSIB-1805402-MF-004 | 12.80 | 49.18 |

TABLE 7

Results of the N2 test; LSD = 3.6609

| Plant | Yield (grams per plant) | % higher than IR64 |
|---|---|---|
| IR 64 | 5.99 | n/a |
| OSIB-878355-M+005 | 10.72 | 78.96 |
| OsIB-258841-M+005 | 13.16 | 119.70 |
| OsIB-258841-M+008 | 11.07 | 84.81 |
| OSIB375578M-M+018 | 10.09 | 68.45 |
| OSIB375578M-MF-001 | 9.90 | 65.28 |
| OSIB375578M-MF-006 | 10.19 | 70.12 |
| OSIB375578M-MF-010 | 9.58 | 59.93 |
| OSIB-26006-MF-010 | 10.24 | 70.95 |
| OSIB-1805402-M+009 | 11.24 | 87.65 |
| OSIB-1805402-M+017 | 9.97 | 66.44 |

Example 4

Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al., Proc. Natl. Acad. Sci. USA, 95:6239-6244 (1998)) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Mo., USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NOs: 2, 337, 61, 111, 27, 209, and 370 are shown in FIGS. 1-7, respectively. Additional exemplary homologs are correlated to certain Figures in the Sequence Listing.

Example 5

Determination of Functional Homologs by Hidden Markov Models

Hidden Markov Models (HMMs) were generated by the program HMMER 3.0. To generate each HMM, the default HMMER 3.0 program parameters were used.

An HMM was generated using the sequences shown in FIG. 1 as input. These sequences were fitted to the model and a representative HMM bit score for each sequence is shown in the Sequence Listing. Additional sequences were fitted to the model, and representative HMM bit scores for any such additional sequences are shown in the Sequence Listing. The results indicate that these additional sequences are functional homologs of SEQ ID NO: 2.

The procedure above was repeated and an HMM was generated for each group of sequences shown in FIGS. 2-7, using the sequences shown in each Figure as input for that HMM. A representative bit score for each sequence is shown in the Sequence Listing. Additional sequences were fitted to certain HMMs, and representative HMM bit scores for such additional sequences are shown in the Sequence Listing. The results indicate that these additional sequences are functional homologs of the sequences used to generate that HMM.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11001849B2). An electronic copy of the "Sequence Listing" will also be available from the USPTO upon request and payment of the fee set forth in 37 CFR 1.19(b)(3).

What is claimed is:

1. A method of increasing plant yield in a plant grown under drought stress, osmotic stress, or nitrogen deficiency, said method comprising: (a) growing plants transformed with an exogenous nucleic acid under drought stress, osmotic stress, or nitrogen deficiency, said exogenous nucleic acid comprising a heterologous promoter operably linked to a nucleotide sequence encoding a polypeptide having at least 95% amino acid sequence identity to the amino acid sequence as set forth in SEQ ID NO: 370; and (b) selecting a transformed plant from said transformed plants that expresses said polypeptide and has increased yield when grown under drought stress, osmotic stress, or nitrogen deficiency as compared to the corresponding yield of a control plant of the same species that does not comprise said exogenous nucleic acid and grown under identical stress conditions.

2. The method according to claim 1, wherein growing said transformed plants is under drought stress, and said drought stress is selected from the group consisting of pre-flowering drought stress and post-flowering drought stress.

3. The method according to claim 1, wherein growing said transformed plants is under osmotic stress, and said osmotic stress is selected from the group consisting of a soil electric conductivity between 4 dS/m and 5 dS/m, and a soil conductivity between 6 dS/m and 7 dS/m.

4. The method according to claim 1, wherein growing said transformed plants is under nitrogen deficiency, and said nitrogen deficiency is selected from the group consisting of a 50 Kg per hectare nitrogen application, and a 75 Kg per hectare nitrogen application.

5. The method according to claim 1, further comprising harvesting biomass from said selected transformed plant.

6. The method according to claim 1, wherein said polypeptide has at least 97% amino acid sequence identity to the amino acid sequence as set forth in SEQ ID NO: 370.

7. A method of producing a plant with tolerance to drought stress, osmotic stress, or nitrogen deficiency, said method comprising:
(a) expressing in a plurality of plants transformed with an exogenous nucleic acid comprising a nucleotide sequence encoding a polypeptide, said exogenous nucleic acid comprising a heterologous promoter operably linked to the nucleotide sequence, and the polypeptide having at least 95% amino acid sequence identity to the amino acid sequence as set forth in SEQ ID NO: 370;
(b) selecting from said plurality of transformed plants a transformed plant that overexpresses said polypeptide and has increased tolerance to drought stress, osmotic stress, or nitrogen deficiency; and
(c) growing the selected transformed plant having increased tolerance to drought stress, osmotic stress, or nitrogen deficiency as compared to a control plant of the same species lacking said exogenous nucleic acid and grown under identical stress conditions.

8. The method according to claim 7, wherein said transformed plant is selected for increased tolerance to drought stress, and said drought stress is selected from the group consisting of pre-flowering drought stress and post-flowering drought stress.

9. The method according to claim 7, wherein said transformed plant is selected for increased tolerance to osmotic stress, and said osmotic stress is selected from the group consisting of a soil electric conductivity between 4 dS/m and 5 dS/m, and a soil conductivity between 6 dS/m and 7 dS/m.

10. The method according to claim 7, wherein said transformed plant is selected for increased tolerance to nitrogen deficiency stress, and said nitrogen deficiency stress is selected from the group consisting of a 50 Kg per hectare nitrogen application, and a 75 Kg per hectare nitrogen application.

11. The method according to claim 7, wherein the polypeptide has 97% or greater amino acid sequence identity to the amino acid sequence as set forth in SEQ ID NO: 370.

12. The method according to claim 1 or 7, wherein said exogenous nucleic acid has 95% or greater nucleotide sequence identity to the nucleotide sequence of SEQ ID NO: 369.

13. The method according to any one of claims 1 or 7, wherein said plant is selected from the group consisting of *Panicum virgatum, Sorghum bicolor, Miscanthus giganteus, Saccharum* sp., *Populus balsamifera, Zea mays, Glycine max, Brassica napus, Triticum aestivum, Gossypium hirsutum, Oryza sativa, Helianthus annuus, Medicago sativa, Beta vulgaris*, and *Pennisetum glaucum*.

14. The method according to claim 1, wherein the nucleotide sequence encodes a polypeptide having the amino acid sequence as set forth in SEQ ID NO: 370.

15. The method according to claim 7, wherein the nucleotide sequence encodes a polypeptide having the amino acid sequence as set forth in SEQ ID NO: 370.

* * * * *